US007959437B2

(12) United States Patent
Zakhem et al.

(10) Patent No.: US 7,959,437 B2
(45) Date of Patent: Jun. 14, 2011

(54) ORTHODONTIC APPLIANCE WITH ENCODED INFORMATION FORMED IN THE BASE

(75) Inventors: Tony Zakhem, Highlands Ranch, CO (US); Jeffrey Allen Smith, Denver, CO (US); Daphne Upchurch, Lakewood, CO (US)

(73) Assignee: RMO, Inc., Denver, CO (US)

( * ) Notice: Subject to any disclaimer, the term of this patent is extended or adjusted under 35 U.S.C. 154(b) by 744 days.

(21) Appl. No.: 11/782,569

(22) Filed: Jul. 24, 2007

(65) Prior Publication Data

US 2008/0020338 A1    Jan. 24, 2008

Related U.S. Application Data

(63) Continuation-in-part of application No. 10/848,929, filed on May 18, 2004, now Pat. No. 7,247,018, which is a continuation-in-part of application No. 10/284,016, filed on Oct. 29, 2002, now Pat. No. 6,846,178.

(51) Int. Cl.
*A61C 3/00* (2006.01)
(52) U.S. Cl. ............................................. 433/9; 433/10
(58) Field of Classification Search .................. 433/8, 9, 433/10, 11, 12, 13, 14, 15, 16; D24/180
See application file for complete search history.

(56) References Cited

U.S. PATENT DOCUMENTS

| 626,476 | A | 6/1899 | Angle |
|---|---|---|---|
| 1,890,487 | A | 12/1932 | Angle |
| 2,196,515 | A | 4/1940 | Atkinson |
| 3,028,671 | A | 4/1962 | Berger |
| 3,055,110 | A | 9/1962 | Kesling |
| 3,193,930 | A | 7/1965 | Bien |
| 3,391,461 | A | 7/1968 | Johnson |
| 3,435,527 | A | 4/1969 | Kesling |
| 3,494,034 | A | 2/1970 | Kesling |
| 3,504,438 | A | 4/1970 | Wittman et al. |
| 3,526,961 | A | 9/1970 | Kesling |
| 3,765,091 | A | 10/1973 | Northcutt |
| 3,838,514 | A | 10/1974 | Polak |
| 3,854,207 | A | 12/1974 | Wildman |

(Continued)

FOREIGN PATENT DOCUMENTS

DE        8903611        8/1990

(Continued)

OTHER PUBLICATIONS

Ricketts "Provocations and Perceptions in Cranio-Facial Orthopedics" RMO, Inc., Denver, CO, USA, 1989, cover and pp. 982-1021.

(Continued)

*Primary Examiner* — Cris L Rodriguez
*Assistant Examiner* — Eric Rosen
(74) *Attorney, Agent, or Firm* — Sheridan Ross P.C.; Dennis J. Dupray

(57) ABSTRACT

An improved orthodontic appliance is disclosed having information encoded or formed in the base of the appliance, wherein the encoded information increases the total base surface area by an amount that is effective for increasing the adhesion of the appliance to a patient's tooth. In one embodiment, the total base surface area may increase to 140% of what such surface would be without the encoded information. The encoded information may identify: a manufacturer or supplier of the appliance, a part/model number, a location and/or date of manufacturer, a composition of material, a patent number, a logo, etc.

18 Claims, 44 Drawing Sheets

U.S. PATENT DOCUMENTS

| | | |
|---|---|---|
| 3,874,080 A | 4/1975 | Wallshein |
| 3,916,526 A | 11/1975 | Schudy |
| 3,964,156 A | 6/1976 | Williams et al. |
| 3,975,824 A | 8/1976 | Lee |
| 3,985,282 A | 10/1976 | Miller et al. |
| 3,987,547 A | 10/1976 | Moss |
| 4,015,334 A | 4/1977 | Moss |
| 4,028,809 A | 6/1977 | Wallshein |
| 4,083,113 A | 4/1978 | Miller et al. |
| 4,103,423 A | 8/1978 | Kessel |
| 4,134,208 A | 1/1979 | Pearlman |
| 4,172,999 A | 10/1979 | Leidich |
| 4,183,141 A | 1/1980 | Dellinger et al. |
| 4,192,070 A | 3/1980 | Lemchen et al. |
| 4,193,195 A | 3/1980 | Merkel et al. |
| 4,197,642 A | 4/1980 | Wallshein |
| 4,212,638 A | 7/1980 | Korn |
| 4,219,617 A | 8/1980 | Wallshein |
| D256,950 S | 9/1980 | Sable |
| 4,242,085 A | 12/1980 | Wallshein |
| 4,248,587 A | 2/1981 | Kurz |
| 4,260,375 A | 4/1981 | Wallshein |
| 4,284,405 A | 8/1981 | Dellinger |
| 4,299,569 A | 11/1981 | Frantz |
| 4,302,532 A | 11/1981 | Wallshein |
| 4,322,206 A | 3/1982 | Reynolds |
| 4,350,487 A | 9/1982 | Kesling et al. |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,455,137 A | 6/1984 | Diamond |
| 4,478,577 A | 10/1984 | Warren, Jr. |
| 4,498,867 A | 2/1985 | Kesling |
| 4,511,331 A | 4/1985 | Scebold et al. |
| 4,527,975 A | 7/1985 | Ghafari et al. |
| 4,529,382 A | 7/1985 | Creekmore |
| 4,531,991 A | 7/1985 | Ziemek et al. |
| 4,545,760 A | 10/1985 | Forster |
| 4,575,337 A | 3/1986 | Fujita |
| 4,626,209 A | 12/1986 | Tsai et al. |
| 4,659,309 A | 4/1987 | Merkel |
| 4,661,059 A | 4/1987 | Kanno |
| D290,040 S | 5/1987 | Kelly |
| 4,669,979 A | 6/1987 | Snead |
| 4,669,981 A | 6/1987 | Kurz |
| D291,919 S | 9/1987 | Reynolds |
| 4,700,697 A | 10/1987 | Mundell et al. |
| 4,712,999 A | 12/1987 | Rosenberg |
| 4,752,221 A | 6/1988 | Hanson et al. |
| 4,773,853 A | 9/1988 | Kussick |
| 4,781,334 A | 11/1988 | Derichs |
| 4,781,582 A | 11/1988 | Kesling |
| 4,793,804 A | 12/1988 | Schudy |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,917,602 A | 4/1990 | Broussard |
| 4,927,360 A | 5/1990 | Pospisil |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,035,614 A | 7/1991 | Greenfield |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,120,218 A | 6/1992 | Hanson |
| 5,125,831 A | 6/1992 | Pospisil |
| 5,125,832 A | 6/1992 | Kesling |
| 5,127,828 A | 7/1992 | Suyama |
| 5,133,740 A | 7/1992 | Kussick |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,203,804 A | 4/1993 | Nikutowski et al. |
| 5,224,858 A | 7/1993 | Hanson |
| 5,226,814 A | 7/1993 | Allen |
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,252,066 A | 10/1993 | Fairhurst |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |
| 5,322,435 A | 6/1994 | Pletcher |
| 5,356,288 A | 10/1994 | Cohen |
| 5,362,232 A | 11/1994 | Franseen et al. |
| 5,362,233 A | 11/1994 | Thompson |
| 5,380,196 A | 1/1995 | Kelly et al. |
| 5,383,784 A | 1/1995 | Sernetz |
| 5,395,238 A | 3/1995 | Andreiko et al. |
| D358,649 S | 5/1995 | Moschik |
| D358,650 S | 5/1995 | Moschik |
| D359,776 S | 6/1995 | Hilgers |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,464,349 A | 11/1995 | Andreiko et al. |
| 5,470,228 A | 11/1995 | Franseen et al. |
| 5,474,445 A | 12/1995 | Voudouris |
| 5,505,616 A | 4/1996 | Harwell |
| 5,522,725 A | 6/1996 | Jordan et al. |
| 5,545,037 A | 8/1996 | Takeshi |
| 5,556,277 A | 9/1996 | Yawata et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,622,494 A | 4/1997 | Andreiko et al. |
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,720,611 A | 2/1998 | Teng |
| 5,727,941 A | 3/1998 | Kesling |
| 5,729,768 A | 3/1998 | Fields et al. |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,791,897 A | 8/1998 | Wildman |
| 5,810,583 A | 9/1998 | Doyle |
| 5,820,371 A | 10/1998 | Forster |
| 5,829,972 A | 11/1998 | Farzin-Nia |
| 5,857,849 A | 1/1999 | Kurz |
| 5,871,350 A | 2/1999 | Clark et al. |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |

| | | |
|---|---|---|
| 5,915,550 A | 6/1999 | Gartz |
| 6,036,489 A | 3/2000 | Brosius |
| 6,053,729 A | 4/2000 | Brehm et al. |
| 6,071,119 A | 6/2000 | Christoff et al. |
| 6,086,364 A | 7/2000 | Brunson |
| 6,109,916 A | 8/2000 | Wilcko et al. |
| 6,123,544 A | 9/2000 | Cleary |
| 6,126,441 A | 10/2000 | Tenti |
| 6,142,775 A | 11/2000 | Hansen et al. |
| 6,190,165 B1 | 2/2001 | Andreiko et al. |
| 6,193,508 B1 | 2/2001 | Georgakis |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,264,469 B1 | 7/2001 | Moschik |
| 6,280,185 B1 | 8/2001 | Palmer et al. |
| 6,302,688 B1 | 10/2001 | Jordan et al. |
| 6,347,939 B2 | 2/2002 | Abels |
| 6,354,834 B2 | 3/2002 | Kanomi |
| 6,361,314 B1 | 3/2002 | Garton, Jr. |
| 6,368,105 B1 | 4/2002 | Voudouris et al. |
| 6,371,760 B1 | 4/2002 | Zavilenski et al. |
| 6,394,798 B1 | 5/2002 | Huff et al. |
| 6,428,314 B1 | 8/2002 | Jones, Jr. et al. |
| 6,461,157 B1 | 10/2002 | Kussick |
| 6,478,579 B1 | 11/2002 | Brusse |
| 6,491,519 B1 | 12/2002 | Clark et al. |
| 6,506,049 B2 | 1/2003 | Hanson |
| 6,582,226 B2 | 6/2003 | Jordan et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,663,385 B2 | 12/2003 | Tepper |
| 6,668,834 B1 | 12/2003 | Zikria |
| 6,695,612 B2 | 2/2004 | Abels et al. |
| 6,705,862 B2 | 3/2004 | Schultz |
| 6,709,268 B2 | 3/2004 | Pospisil et al. |
| 6,733,286 B2 | 5/2004 | Abels et al. |
| 6,769,910 B1 | 8/2004 | Pantino |
| 6,776,613 B2 | 8/2004 | Orikasa |
| 6,846,178 B2 | 1/2005 | Freeman, Jr. et al. |
| 6,863,528 B2 | 3/2005 | Lin |
| 6,893,257 B2 | 5/2005 | Kelly |
| 6,903,262 B2 | 6/2005 | Blersch |
| 6,910,884 B2 | 6/2005 | Kelly et al. |
| 6,913,459 B2 | 7/2005 | Fukutomi |
| 7,001,179 B2 | 2/2006 | Devincenzo |
| 7,025,591 B1 | 4/2006 | Kesling |
| 7,033,170 B2 | 4/2006 | Cordato |
| 7,033,171 B2 | 4/2006 | Wilkerson |
| 7,055,908 B1 | 6/2006 | Williams |
| 7,140,875 B2 | 11/2006 | Lai et al. |
| 7,151,541 B2 | 12/2006 | Seder |
| 7,210,927 B2 | 5/2007 | Abels et al. |
| 7,234,935 B2 | 6/2007 | Abels et al. |
| 7,258,545 B2 | 8/2007 | Hotta |
| 7,267,545 B2 | 9/2007 | Oda |
| 2002/0110778 A1 | 8/2002 | Abels et al. |
| 2002/0187452 A1 | 12/2002 | Abels et al. |
| 2003/0049582 A1 | 3/2003 | Abels et al. |
| 2003/0096209 A1 | 5/2003 | Sugiyama et al. |
| 2003/0143509 A1 | 7/2003 | Kopelman et al. |
| 2004/0259048 A1 | 12/2004 | Balabanovsky |
| 2005/0003320 A1 | 1/2005 | Freeman et al. |
| 2005/0069833 A1 | 3/2005 | Chikami |
| 2005/0244777 A1 | 11/2005 | Schultz |
| 2006/0019212 A1 | 1/2006 | Macchi |
| 2006/0046224 A1 | 3/2006 | Sondhi et al. |
| 2007/0256694 A1 | 11/2007 | Kussick |
| 2008/0138759 A1 | 6/2008 | Kravitz et al. |
| 2008/0223377 A1 | 9/2008 | Kussick |

FOREIGN PATENT DOCUMENTS

| | | |
|---|---|---|
| DE | 69228472 | 10/1999 |
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| JP | 64-25847 | 1/1989 |
| JP | 1-160547 | 6/1989 |
| JP | 2-147112 | 12/1990 |
| JP | 3-21236 | 1/1991 |
| JP | 2579431 | 2/1997 |
| JP | 11-276504 | 10/1999 |
| WO | WO 91/07925 | 6/1991 |
| WO | WO 92/00041 | 1/1992 |
| WO | WO 92/20296 | 11/1992 |
| WO | WO 2004/039276 | 5/2004 |

OTHER PUBLICATIONS

U.S. Appl. No. 10/821,699, filed Apr. 9, 2004, Ricketts.
U.S. Appl. No. 11/123,470, filed May 5, 2005, Wilson.
U.S. Appl. No. 11/260,923, filed Oct. 27, 2005, Stevens.
U.S. Appl. No. 11/695,555, filed Apr. 2, 2007, Wolf.
U.S. Appl. No. 11/740,812, filed Apr. 26, 2007, Muha.
U.S. Appl. No. 11/852,057, filed Sep. 7, 2007, Smith.
3M Unitek Corporation Catalog (1990), pp. 1-1, 1-3 and 3-7.
Ortho Orgainzers, Inc. Advertisement "Journal of clinical Orthodontics"; (Sep. 1989).
"Direct Bond Tubes" American Orthodontics, date unknown, p. 76.
International Search Report for International (PCT) Patent Application No. PCT/US03/34430, mailed May 24, 2004.
"Focus on Brackets," Orthodontic Products, pp. 1-2 (Mar. 2005).
Epstein, "Bi-Dimensional Orthos Treatment: Benefits and Rationale of Differential Bracket-Slot Sizes", Copyright 2002, pp. 1-6.
Buccal Tube, Sankin, date unknown, 7 pages.
Victory Series Appliance System, Mastering the Art of Orthodontic Application, 3M Unitek Dental Products Division, 1998, 4 pages.
U.S. Appl. No. 12/724,159, filed Mar. 15, 2010, Macchi.
U.S. Appl. No. 12/758,090, filed Apr. 12, 2010, Stevens.

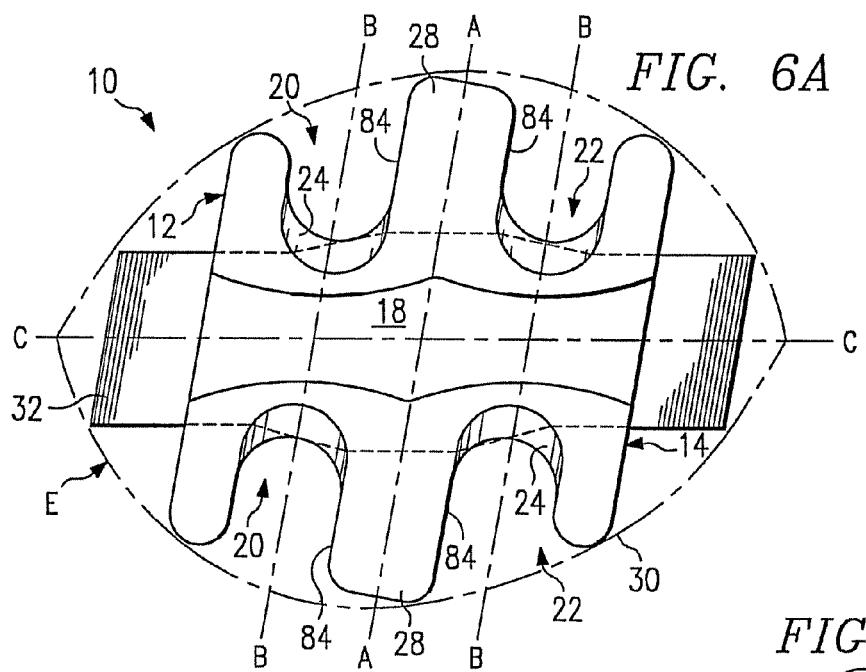
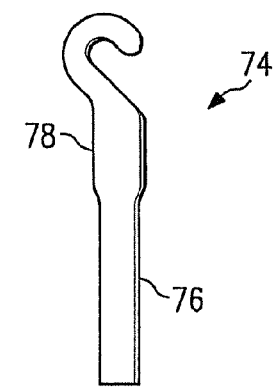
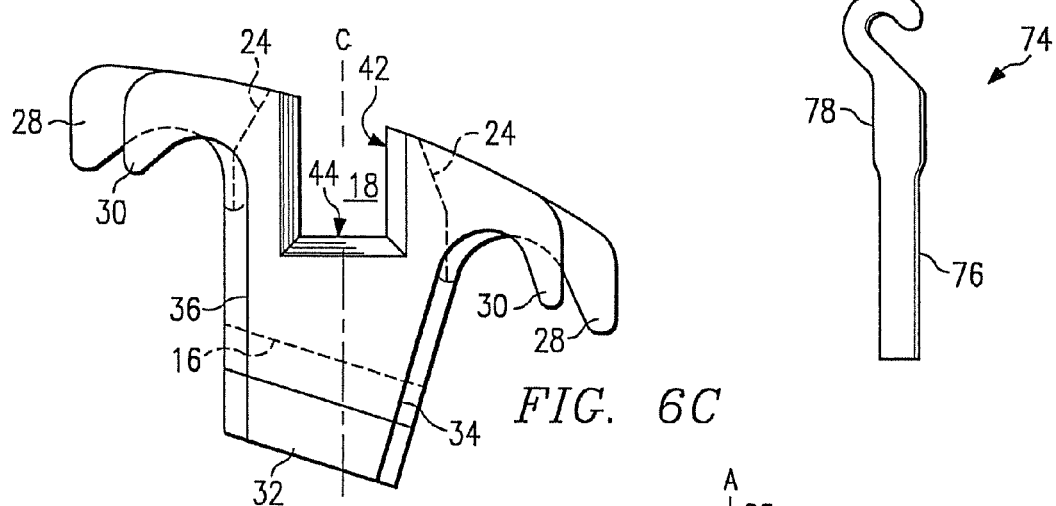
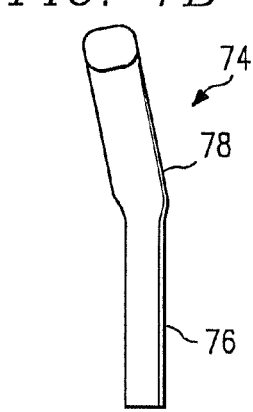
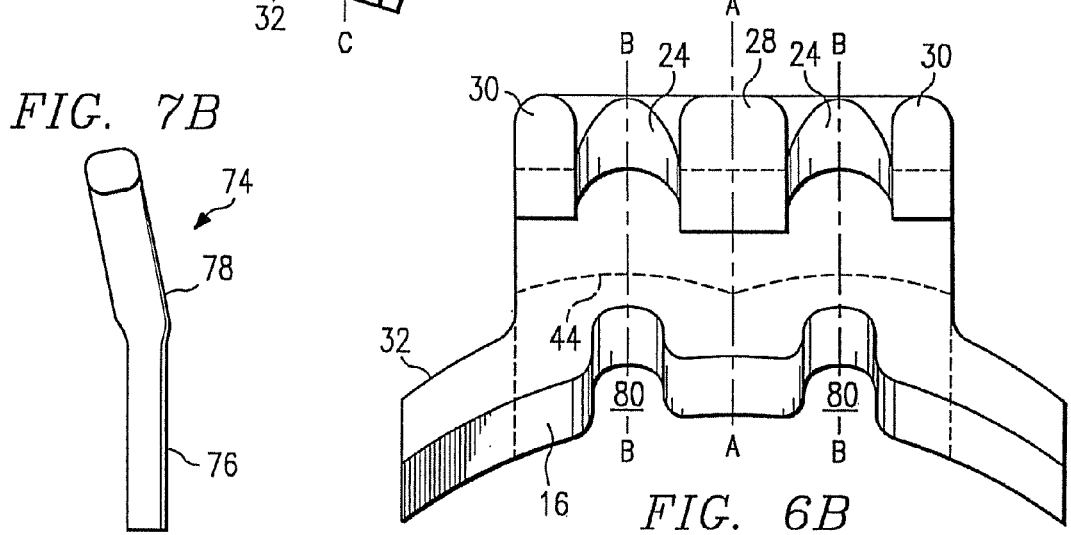

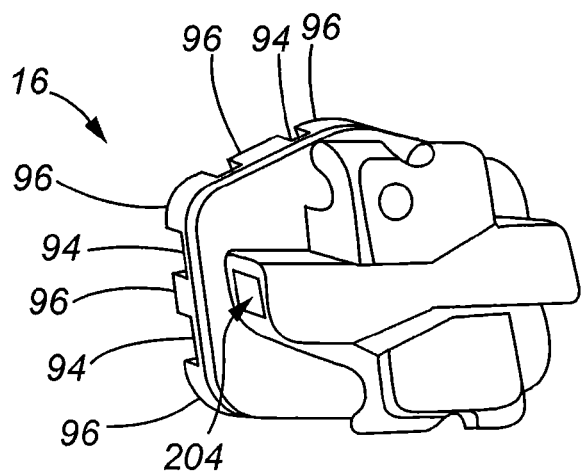
Fig. 50
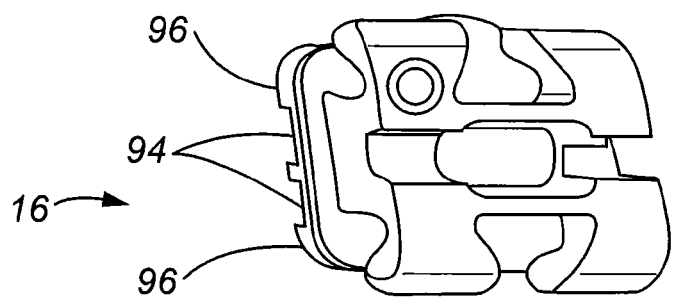
Fig. 51
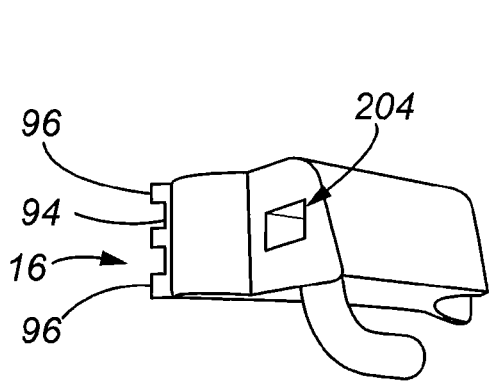
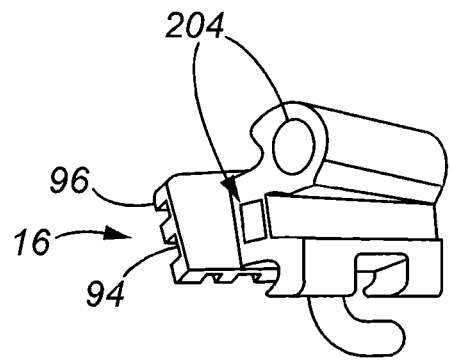
Fig. 52  Fig. 53

ORTHODONTIC APPLIANCE WITH ENCODED INFORMATION FORMED IN THE BASE

REFERENCE TO RELATED APPLICATIONS

This is a continuation-in-part application of prior U.S. patent application Ser. No. 10/848,929 filed May 18, 2004 (now U.S. Pat. No. 7,247,018), which is a continuation-in-part of U.S. patent application Ser. No. 10/284,016 filed Oct. 29, 2002, and entitled "Orthodontic Bracket Base Apparatus and Method of Manufacture," each of the above-identified patent applications is incorporated herein by reference in its entirety.

FIELD OF THE INVENTION

This invention generally relates to an orthodontic appliance such as a bracket or a tube having information embedded or formed into the underneath side of the base of the appliance.

BACKGROUND OF THE INVENTION

Orthodontic brackets are widely used to align teeth through the application of forces selectively provided by interconnected archwires and accessories. Brackets are typically of metal, ceramic or composite construction and are interconnected to either bands or bonding pads for attachment to teeth.

In edgewise brackets, an archwire passes through a labially opening, horizontal slot defined by one or more pair of opposing tie wings. The archwire is preshaped and sized to provide the desired forces. In each bracket, a tie wing pair includes a gingivally extending tie wing and occlusally extending tie wing. Once placed in the slot of one or more pair of tie wings, an archwire is typically restricted therein by a ligating device such as a steel or elastomeric ligature.

As orthodontic treatment objectives and techniques continue to evolve, numerous corresponding edgewise bracket designs and interconnecting accessories have been proposed. Recently, it has been recognized that it is desirable to reduce frictional engagement between the archwire and bracket surfaces defining the archwire slot to facilitate space closure and bodily tooth movement. Similarly, in many situations, it is now a goal to reduce frictional engagement between the archwire and ligating device employed to restrict the archwire within the slot. Such friction reduction can markedly increase the rate of tooth movement and reduce the duration of the orthodontic treatment.

At the same time, patient comfort and ease-of-use considerations have become increasingly important. Patient comfort has been largely addressed by reducing bracket size to yield smaller and more smoothly contoured brackets. Ease-of-use considerations have stimulated bracket designs which facilitate practitioner's bracket placement/use and accommodate plural modalities.

Texturing of the lingual surface of orthodontic brackets has been used to provide improved bonding between the bracket and the tooth to which the bracket is applied. For example, U.S. Pat. No. 5,522,725, incorporated herein by reference, concerns a method of improving the bond strength of a plastic bracket by temporarily heating and then permanently deforming projections located on the base of the bracket. The deformed projections interlock with adhesive when the bracket is bonded to a tooth. U.S. Pat. No. 5,595,484, incorporated herein by reference, discloses a plastic bracket having a metal reinforcement member partly embedded in the bracket body. FIG. 13 of the '484 patent discloses a bracket base having eight recessed discontinuous portions 36 that include molded identification characters 35. U.S. Pat. No. 5,622,494 (the '494 patent), incorporated herein by reference, discloses several structures, including a spiral-like ridge, concentric rectangles, and a weave pattern. Upon being deformed, each structure creates an undercut structure for forming a mechanical bond with an adhesive. However, the '494 patent and the other patents noted above fail to disclose a base structure that includes lettering, symbols, or numerals that are substantially continuous and that functionally serve as texturing to enhance the adhesive bonding surface of, e.g., an orthodontic appliance to a patient's tooth. The present disclosure, amongst other things as described below, addresses these shortcomings.

SUMMARY

In one aspect of the present disclosure, an orthodontic appliance, e.g., a bracket or tube, is described, wherein the appliance has information formed (equivalently, embedded) in the underneath side of the base of the appliance. In particular the information may be one or more symbols formed in the underneath side of the base in a manner wherein such embedded symbols are also structurally important to the adhesion of the appliance to a patient's tooth. That is, the symbols significantly increase the total surface area of the appliance base to which an adhesive can bond.

In one embodiment of the present disclosure provides a substantially continuous series of alpha-numeric characters (such as letters or numerals) or symbols (such as company logos) that are formed or embedded in the base in a manner such that the symbols or characters of the base of the bracket serve to increase the base total surface area (which includes the area of the walls separating the projected portions of the base from the recessed portions of the base) to which an adhesive can effectively adhere for effectively facilitating bonding of the orthodontic appliance with a patient's tooth when the base of the appliance is attached to the tooth. Hereafter, the term "characters" refers to either letters, and/or numbers, and/or graphics, and/or symbols (such as logos), and/or various portions of an informational encoding, and/or a combination thereof. "Substantially continuous" is meant to convey the regular matrix-like aspect of the characters configured on the appliance base so as to facilitate a more or less textured surface for bonding purposes.

In another embodiment disclosed herein, an orthodontic appliance may have an embedded base that does not include a substantially continuous series of characters, but instead may include a non-repeating encoding of information, e.g., about the appliance.

One of the heretofore unappreciated aspects provided by the present disclosure includes the ability of a manufacturer and/or supplier of orthodontic devices to have a trademark or other identifying character (i.e., a name, symbol, part number, etc.) emblazoned on the actual device. This contributes to customer confidence in purchases of "real" (vs. knock-off) products and further permits effective recalls of product in the event of later discovered difficulties.

In a separate aspect of the disclosure, a perimeter rail, and more preferably, a discontinuous perimeter rail may be used at the perimeter edges of the base. The discontinuous perimeter rail, if used, is in contact with the tooth surface, with the interior portion of the information content in the base having its characters recessed relative to the surface of the discontinuous perimeter rail. If used, the perimeter rail forms a pocket to the base interior surrounded by the perimeter rail wherein this base interior receives the adhesive for attaching the orthodontic appliance to the tooth surface. Thus, if used, a perimeter rail contacts the tooth surface, with the base embedded information content recessed relative to the surface of the perimeter rail.

Since the characters are preferably recessed, the space between and around the characters is preferably non-recessed or projected. Thus, the projected space between the characters is either in contact with the tooth, or is the next surface closest to the tooth's surface if a perimeter rail is present, as discussed below. The surface of the recessed characters is preferably further away from the tooth surface than the space between the characters. Alternatively, the opposite arrangement may be used, where the space between and around the characters is recessed, and the characters themselves are projected. In either case, the walls between the projected and recessed portions of the appliance base may increase the total surface area for adhesive contact in the range of 120% to 125% of what a two dimensional appliance base might provide, and in at least some embodiments 140% or more, wherein the two dimensional appliance base has the same exterior dimensions and general convexity as the appliance base, but without the undulating or abrupt changes in the base surface curvature that do not follow the smoothly changing contour of a patient's tooth. More preferably, the total surface area for adhesive contact may be at least 144% of what a two dimensional appliance base provides. For example, the corresponding two dimensional base is effectively a flat or convex surface that generally conforms to a surface of a tooth. Said another way, for orthodontic bases according to the present disclosure, the at least 125% value above corresponds to at least 20% of the total surface area of the base being provided by the walls of the characters that connect the most recessed surface portions of the base from the more projected portions of the base, and the at least 144% value above corresponds to at least 29% of the total surface area of the base being provided by the walls of the characters that connect the most recessed surface portions of the base from the more projected portions of the base. Note that such an increase in base total surface area is believed to substantially distinguish the embedded information of the present orthodontic appliances from those of the prior art.

The disclosure herein shows an orthodontic appliance having a pair of tie wings defining an archwire slot therebetween, and a pair of ligating support means, one defined within the mesial/distal extent of each tie wing. The ligating support means may be selectively employed to reduce frictional engagement between an archwire positioned in the slot and a ligating device positioned on the ligating support means and across the archwire slot. Each ligating support means includes a sloped, or angled, portion that extends labially toward the slot (e.g., labially from the gingival/occlusal periphery towards the slot), to reduce binding of a ligating device positioned thereupon. The ligating support means are preferably notches extending from the gingival or occlusal periphery of a tie wing, sized to readily receive a ligating device, and preferably having a curvilinear, concave configuration to further reduce binding. Typically, the opposing notches in a given pair of tie wings have a common center axis which is parallel to the gingival-occlusal center axis of the orthodontic appliance. When the archwire slot includes convex sidewall and/or floor portions to reduce frictional engagement between the archwire and the appliance, the ligating support means are preferably disposed adjacent thereto (e.g., centered upon a common gingival-occlusal plane) for enhanced treatment control.

In another aspect of the present disclosure, an edgewise bracket is disclosed having a single pair of tie wings and two pairs of opposing ligating support means defined within the mesial/distal extent of the tie wings, one pair on each of the mesial and distal sides of the bracket. The gingival/occlusal extremes of the tie wings define an elliptical configuration when viewed from the labial ("viewed labially"). More particularly, each tie wing comprises central, mesial and distal portions which extend gingivally or occlusally, with ligating support means defined between the central and mesial portions and between the central and distal portions, wherein the gingival/occlusal edges of such portions define an elliptical configuration. Such configuration accommodates size reduction, yielding patient comfort benefits, while preserving structural integrity and performance.

In this regard, and as will become apparent, a single pair of opposing T-shaped tie wings is preferred. That is, the "caps" of the T-shaped tie wings define an archwire slot therebetween, and the "center legs" of each tie wing extends gingivally or occlusally. The ligating support means are preferably notches defined on the gingival/occlusal periphery on both the mesial and distal sides of a center leg of each T-shaped tie wing. The center legs each comprise a gingivally/occlusally extending cantilevered portion that can be conveniently employed as a stanchion for ligature interconnection. The mesial/distal tie wing tip portions on the outside of each notch also comprise gingivally/occlusally extending cantilevered portions that extend a sufficient distance outward from the outer tie wing sidewalls to retain a ligating device in an arcuate seat formed under the cantilevered tie wing tip portions and center legs during conventional ligation. Relatedly, the cantilevered center leg of each T-shaped tie wing should extend at least approximately the same distance outward beyond the outer gingival/occlusal extremes of the adjacent ligating support means so as to retain a ligating device when the ligating support notches are selectively employed by a practitioner to support a ligating device.

In a further aspect of the present disclosure, an edgewise bracket is provided having a single pair of tie wings defining an archwire slot therebetween, and an integral T-shaped hook extending gingivally/occlusally (typically only gingivally) from one tie wing, and in perpendicular relation to the longitudinal center axis of the archwire slot, wherein traction devices (e.g., rubber bands, springs, etc.) can be readily attached from a plurality of directions so as to accommodate plural modalities for treatment. The T-shaped hook is centered upon the gingival-occlusal center axis of the bracket, and is preferably provided as a cantilevered extension of the center leg of a T-shaped tie wing so as to communicate external force moments created by inter-connected traction devices close to a tooth's root center of resistance. Preferably, the T-shaped hook is generally flat as viewed from the mesial and distal aspects. Further, as viewed from the labial aspect, the T-shaped hook preferably comprises a tapered portion contiguous to the center leg of the T-shaped tie wing, an arcuate neck portion contiguous thereto, and a head portion contiguous thereto the tapered portion, wherein a traction device may be reliably maintained in the neck portion. That is, the tapered portion serves to restrict movement of the traction device towards the archwire slot of the bracket, and the head portion serves to restrict disconnection of the traction device from the T-shaped hook. The integral T-shaped hook preferably comprises a malleable material so as to allow for selective pivotal movement of the T-shaped hook by the orthodontic practitioner as may be desirable for soft tissue clearance and patent comfort.

In yet another aspect of the present disclosure, an edgewise bracket is provided having at least one pair of tie wings defining an archwire slot therebetween, wherein when viewed from mesial/distal aspects, the gingivally/occlusally facing outer sidewalls of the tie wing pair define a trapezoid (although rounded and/or curved sidewalls are also contemplated). One outer sidewall is disposed at an angle relative to the longitudinal center plane of the archwire slot, wherein the sidewall extends labially away from such center plane. The other sidewall is disposed substantially parallel to the archwire slot center plane. The angled sidewall is typically disposed gingivally in both maxillary and mandibular applications. By way of example, use of the described configuration and positioning allows for enhanced, early treatment of partially erupted upper bicuspids, wherein the archwire slot will be acceptably, gingivally positioned upon full eruption of the bicuspid. This enhances treatment and reduces demands upon the practitioner time. Further, bracket systems of this design will generally reduce bracket/tooth contact between the upper and lower arches. Bracket profile and strength can also be acceptably maintained using the described configuration. The benefits associated with this trapezoidal configuration may be extended to orthodontic treatment applications requiring positive, negative, or no torque by appropriately configuring/contouring the occlusal/gingival extent of the bracket base or bottom.

In another aspect of the present disclosure, an edgewise bracket is provided having one tie wing pair defining an archwire slot therebetween and at least one auxiliary slot extending from a gingival edge to the occlusal edge, or vice versa, wherein the slot and shaft of the auxiliary device to be inserted into the slot have complimentary configurations to restrict rotational movement therebetween. By way of example, the auxiliary slot may have adjoining flat inner sidewalls (e.g., defining square corners), and the auxiliary shaft may have complimentary flat outer sidewalls (e.g., defining square corners), wherein rotational movement therebetween is desirably restricted.

In a related aspect of the present disclosure, an edgewise bracket is provided having a single tie wing pair defining an archwire slot therebetween, at least one convex portion extending labially and transversely across the floor of the archwire slot, and at least one auxiliary slot extending gingivally/occlusally and positioned under the convex slot floor portion. By positioning the auxiliary slot under the convex slot floor portion, bracket height can be advantageously conserved, and therefore reduced, so as to enhance patient comfort. When two convex slot floor portions are provided, one on each of the mesial/distal sides, twin auxiliary slots may be advantageously positioned so that one passes under each of the convex slot floor portions. In addition to the above-noted advantages, this bracket yields significant tooth rotation capabilities. For example, in early treatment stages, the twin auxiliary slots can be utilized with a steel ligature to achieve rapid gross tooth rotation. As can be appreciated, complementary auxiliary slot/auxiliary shaft configurations of the above-described nature can also be employed.

In one embodiment of the present disclosure, an edgewise bracket is provided having a single set of opposing T-shaped tie wings with ligating support notches defined on each side (i.e., mesially and distally) of the center leg of each tie wing. The sidewalls defining the archwire slot are provided to present two sets of opposing convex sidewall portions, one set on each of the mesial and distal sides of the bracket. Similarly, the floor of the archwire slot is provided to present two convex portions extending labially and transversely across the slot, one on each of the mesial and distal sides of the bracket. By virtue of this arrangement, the bracket yields desirable tooth rotation and alignment capabilities with reduced archwire/archwire slot frictional engagement and selectively reduced archwire/ligating device frictional engagement. Further, this configuration defines a dynamic archwire slot, wherein the archwire is allowed to maintain a "memory" of its slot entry angle, as is now desirable. The notches each comprise a portion that extends labially outwardly from the gingival/occlusal periphery towards the archwire slot and presents concave, curvilinear surfaces to reduce ligature binding. The gingival/occlusal edges of the center legs and wing tip portions of the opposing T-shaped tie wings define an elliptical configuration when viewed labially so as to reduce bracket size and advance patient comfort/appearance. All prominent edges exposed to soft tissue are preferably rounded for patient comfort.

An integral T-shaped hook of the above-described nature may be optionally provided as a cantilevered gingival/occlusal extension of the center leg of either T-shaped tie wing. The T-shaped hook preferably comprises a malleable material and preferably comprises flat lingually and labially facing surfaces, wherein the hook can be manually pivoted to a limited extent by a practitioner relative to the center leg of the tie wing.

An auxiliary slot may also be optionally provided and disposed within the gingival-occlusal center plane of the bracket, underlying the center leg portions of the opposing T-shaped tie wings. Alternatively, twin auxiliary slots may be provided, one on each side of the gingival-occlusal center plane of the bracket (i.e., mesially and distally positioned), such slots passing under the mesial and the distal convex slot floor portions of the archwire slot. Whether a single or twin auxiliary slot arrangement is provided, each slot preferably has an inner-configuration which will restrict rotation of complimentary auxiliaries inserted thereto, as described above.

The T-shaped tie wings of the bracket may also be optionally defined so that the outer gingival/occlusal facing sidewalls of the tie wing pair define a trapezoid when viewed from the mesial or distal aspects. More particularly, one of the outer sidewalls is disposed at an angle relative to the longitudinal center plane of the archwire slot, and may be perpendicular to the tie wing base surface or base/bottom surface of the bracket. The other outer sidewall is disposed in parallel relation to the center plane of the archwire slot.

In combination with the above-described trapezoidal configuration, the base surface of the bracket, namely its gingival/occlusal extent, may be provided for generating "positive torque," "negative torque," and "no torque." "Positive torque" is applied to a tooth having a tooth-long axis which projects the crown outwardly from a plane which is perpendicular to the occlusal plane and which coincides with the respective arch (e.g., mandibular or maxillary) (e.g., when the tooth root is tipped lingually). "Negative torque" is applied to a tooth having a tooth-long axis which projects the crown inwardly from the above-described plane (e.g., when the tooth root is tipped buccally). "No torque" is applied to a tooth having a tooth-long axis which is properly within the above-described plane.

The configuration of the base surface of the bracket, namely its occlusal/gingival extent, may be defined in relation to a reference plane which coincides with that portion of the floor or bottom of the archwire slot which engages the archwire when positioned therein (e.g., a plane which is tangent to the two convex portions on the floor of the slot). As an example of the foregoing trapezoidal configuration and base variations, with the "angled" outer sidewall being gingivally positioned in a maxillary application, the base may be configured to generally extend from its gingival edge to its occlusal edge generally toward the noted reference plane to provide for a "positive torque" on the tooth. Moreover, the base may be configured to generally extend from its gingival edge to its occlusal edge generally away from the noted reference plane to provide for "negative torque" on the tooth. Furthermore, the base may be configured to generally extend from its gingival edge to its occlusal edge generally parallel to the noted reference plane to provide for "no torque" on the tooth. With the "angled" outer sidewall being gingivally positioned in a mandibular application, the above-described non-parallel configurations of the base would provide negative and positive torque, respectively.

The center leg of each T-shaped tie wing may also be optionally disposed at an acute angle relative to the longitudinal center axis of the slot. Such angling may be desired in applications wherein the central axis of the clinical crown is positioned at an acute angle relative to the occlusal plane in normal occlusion. Such angling correspondingly facilitates the practitioner's placement of the bracket on a tooth, wherein the axes of the center legs may be disposed along a tooth long axis, and wherein the center axis of the bracket slot may be disposed parallel to the occlusal plane. Preferably, the mesial/distal facing edges of the center leg of each T-shaped tie wing are also parallel to the axes of the center legs to further facilitate accurate placement on a tooth. It is also preferable for the center axes of opposing ligating support notches to be disposed parallel to the gingival-occlusal center plane of the bracket. Relatedly, for rotational purposes, it is preferable for the apices of the opposing convex slot sidewall portions and a convex slot floor portion correspondingly positioned on the same mesial or distal side to lie within a common plane that is disposed substantially perpendicular to the longitudinal center plane of the archwire slot.

The present disclosure further includes a method for manufacturing and distributing embodiments of the novel orthodontic appliance to orthodontists and other trained personnel for the application of such an orthodontic appliance to a patient's tooth. In particular, such orthodontic appliances may be injection molded with the embedding of encoded information molded into the base of each such appliance. However, other techniques for embedding the encoded information into the base are also within the scope of the present disclosure, including: metal injection mold (MIM) techniques, plastic injection mold (PIM) techniques, ceramic injection mold (CIM) techniques, casting techniques and/or machining techniques as one of skill in the art will understand.

Various embodiments of the present disclosure are set forth in the attached figures and in the detailed description as provided herein and as embodied by the claims. It should be understood, however, that this Summary section may not contain all of the aspects and embodiments claimed herein. Additionally, the disclosure herein is not meant to be limiting or restrictive in any manner, and is directed to be understood by those of ordinary skill in the art. Moreover, the present disclosure is intended to encompass and include obvious improvements and modifications of embodiments presented herein.

Additional advantages of the present disclosure will become readily apparent from the following discussion, particularly when taken together with the accompanying drawings.

BRIEF DESCRIPTION OF THE DRAWINGS

FIGS. 6A-C illustrate labial, side and opposing end views of the modified version of the first embodiment illustrated in FIGS. 4A-C, with an angulated gingival-occlusal center axis and twin auxiliary slots.

FIGS. 7A-B illustrate two views of an exemplary auxiliary device useable with the auxiliary slots of, e.g., the embodiment of the orthodontic bracket shown in FIG. 6B.

FIGS. 28 through 63 show various orthodontic appliances with bases 16 having encoded information embedded or formed therein, wherein the characters 94 are on the recessed surface(s) 90 (e.g., as shown in FIGS. 9A and 9B), and the intermediary space 96 between the characters is provided on the projected surface(s) 92 (e.g., as shown in FIGS. 9A and 9B). Note that for a given figure number, whenever there are figures A and B for the figure number, such figures A and B are different views of the same orthodontic appliance; e.g.

Figure 1A:
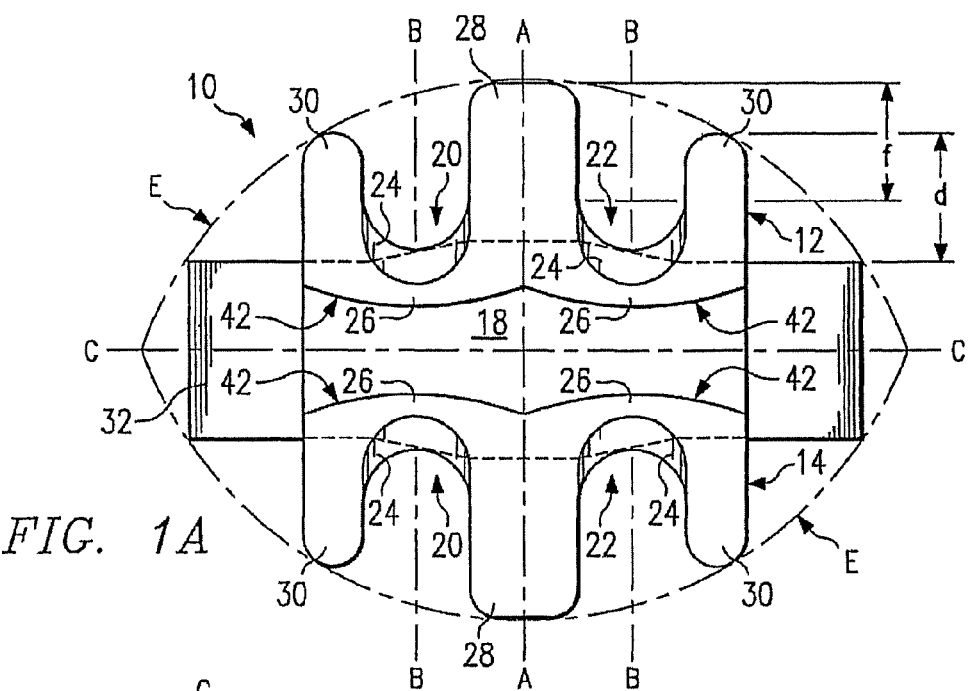
FIGS. 1A-C illustrate labial, side and end views of a first embodiment of an orthodontic bracket.

The drawings are not necessarily to scale. However, the drawings are believed to be proportionately accurate.

DETAILED DESCRIPTION

One embodiment of the body 8 of an edgewise bracket 10 of the present disclosure is illustrated in FIGS. 1A-C and 2A-D, with various modifications, modalities and an exemplary auxiliary reflected by FIGS. 3A-C, 4A-E, 5A-C, 6A-C and 7A-B, and with various base structures and as illustrated in FIGS. 8-18 and 20-59. Corresponding features are referenced by common reference numerals.

The edgewise bracket 10 comprises two integral, opposing T-shaped tie wings 12 and 14 having a common base portion and base surface 16, and defining an archwire slot 18 therebetween. By way of example only, a flange 32 may be adjoined to the bracket 10 for subsequent attachment to a band. Alternatively, the bracket may be adjoined to a bonding pad (not shown).

Two sets of opposing ligating support means 20 and 22, are provided, each set comprising a gingivally disposed notch and occlusally disposed notch on the gingival and occlusal edges of tie wings 12, 14, respectively. Each ligating support means has a sloped portion 24 and top land portion 26. The sloped portions 24 have concave, curvilinear surfaces.

Each of the T-shaped tie wings 12, 14 comprises a cantilevered central leg portion 28 centered upon the gingival-occlusal center axis (lying within plane AA) of the bracket 10 and cantilevered mesial/distal wing tip portions 30, with the above-noted top land portions 26 integral-therebetween. The gingival/occlusal extremes of the center leg 28 and mesial/distal wing tip portions 30 of the tie wings 12, 14 define, from the labial aspect, an elliptical configuration E. In this regard, cantilevered wing tip portions 30 extend a sufficient distance d outward from the outer sidewalls 34, 36 of the tie wings 12, 14, respectively, to retain a ligating device in an arcuate seat 38 formed under the cantilevered tie wing tip portions 30 and center legs 28. Relatedly, the cantilevered center leg 28 of each T-shaped tie wing 12, 14, extends a distance f beyond the outer gingival/occlusal extreme of the ligating support means 20 adjacent thereto, such distance f being at least approximately as great as the distance d.

Figure 1C:
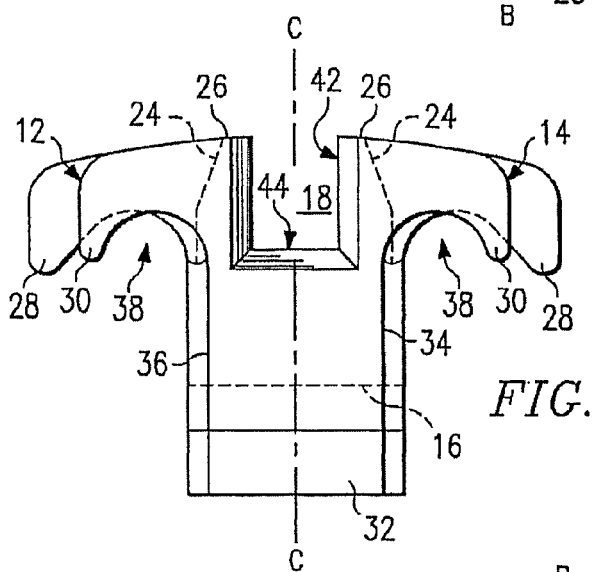
Figure 1B:
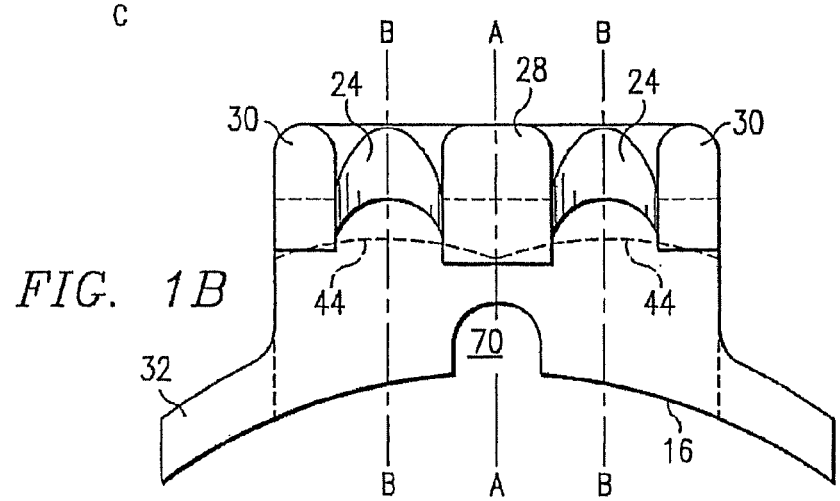

The sidewalls defining the archwire slot 18 comprise two sets of opposing convex portions 42 to reduce functional engagement with an archwire. Similarly, the floor of archwire slot 18 is provided with two convex portions 44 extending transversely across the archwire slot 18 to reduce frictional engagement with an archwire. As illustrated in FIGS. 1A-C, the ligating support means 20, convex slot sidewall portions 42, and convex slot floor portion 44 disposed on the same side of the gingival-occlusal center plane AA may have a common center axis (lying within plane BB). As such, frictional engagement between an archwire and the slot walls and base, and between an archwire and ligating device supported on ligating support means 20 occurs in a limited region about plane BB.

An optional auxiliary slot 70 may be provided to receive a complimentary auxiliary device, such as the exemplary auxiliary 74 illustrated in FIGS. 7A and 7B. The inner sidewalls of auxiliary slot 70 and interfacing shaft portion 76 of the exemplary auxiliary 74 are preferably configured to restrict rotational movement therebetween. As illustrated, a complimentary square-angled configuration may be employed. Additionally, the auxiliary 74 preferably comprises an extending portion 78 having an outer configuration which will not fit into auxiliary slot 70, thereby facilitating placement and removal.

Figure 2A:
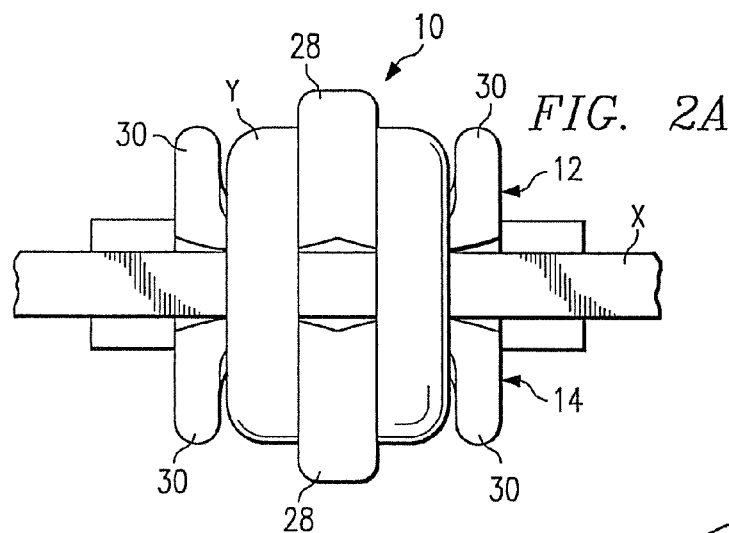
FIGS. 2A and 2B, illustrate labial and end views of the first embodiment of FIGS. 1A-C when ligating support means are employed to support an elastomeric ligature.
Figure 2B:
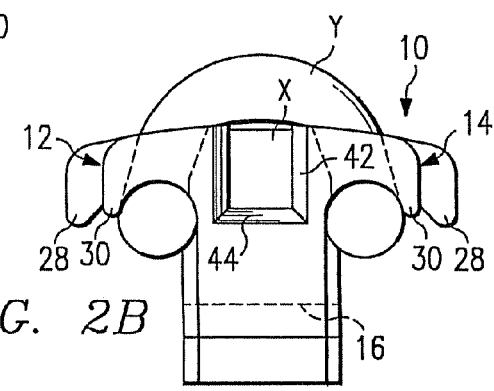
Figure 2C:
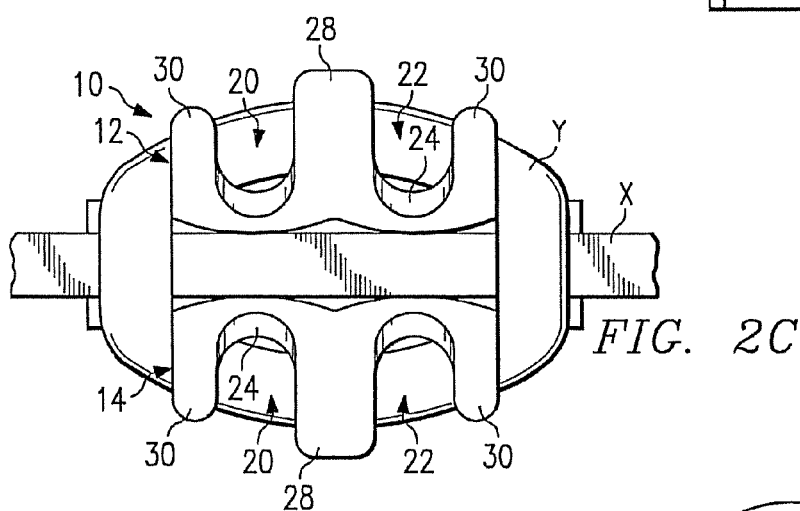
FIGS. 2C and 2D illustrate labial and end views of the first embodiment of FIGS. 1A-C when ligating support means are not employed to support an elastomeric ligature, respectively.
Figure 2D:
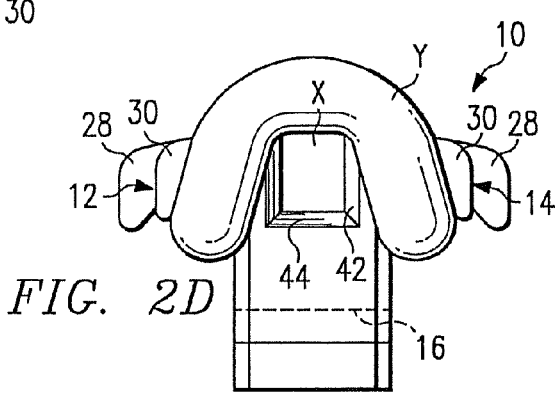

FIGS. 2A-B illustrate the interface between an archwire X and elastomeric ligating device Y when both sets of the ligating support means 20 of the embodiment illustrated in FIGS. 1A-C are utilized. FIGS. 2C-D illustrate the interface between an archwire X and elastomeric ligating device Y when neither of the ligating support means 20 of such embodiment are utilized. As will be appreciated by those in the art, there are different treatment situations where each of these modalities may be desired. Additionally, the provision of a set of ligating support means 20 on each of the mesial and distal sides of the bracket 10 allows a practitioner to utilize one set but not the other, as may be desirable.

Figure 3A:
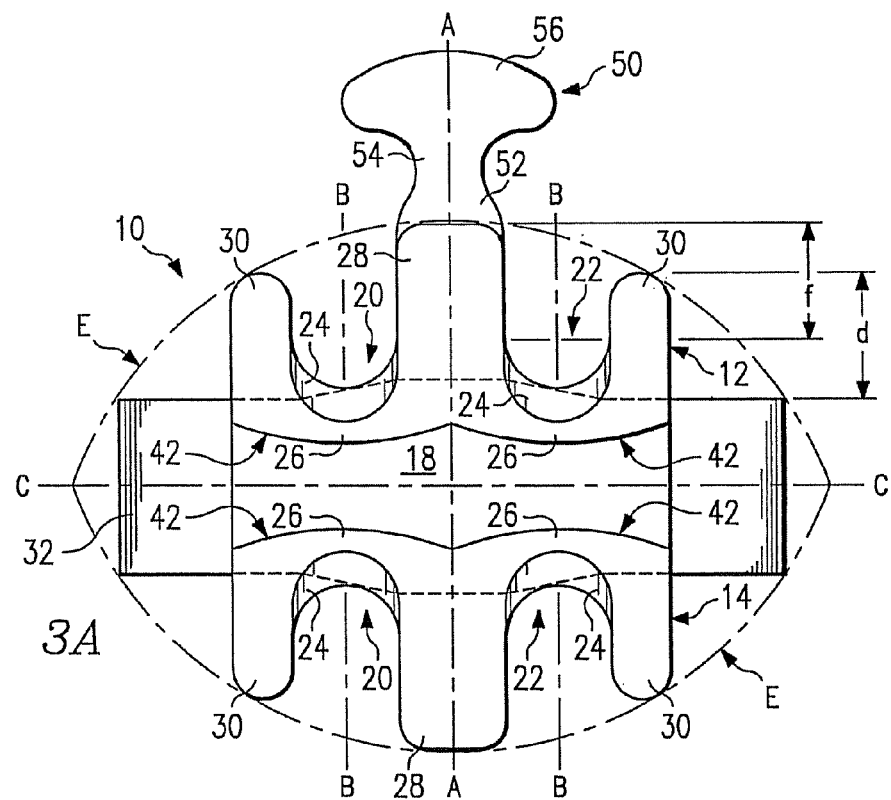
FIGS. 3A-C illustrate labial, side and end views of a modified version of said first embodiment having an integral T-shaped hook and twin auxiliary slots.
Figure 3C:
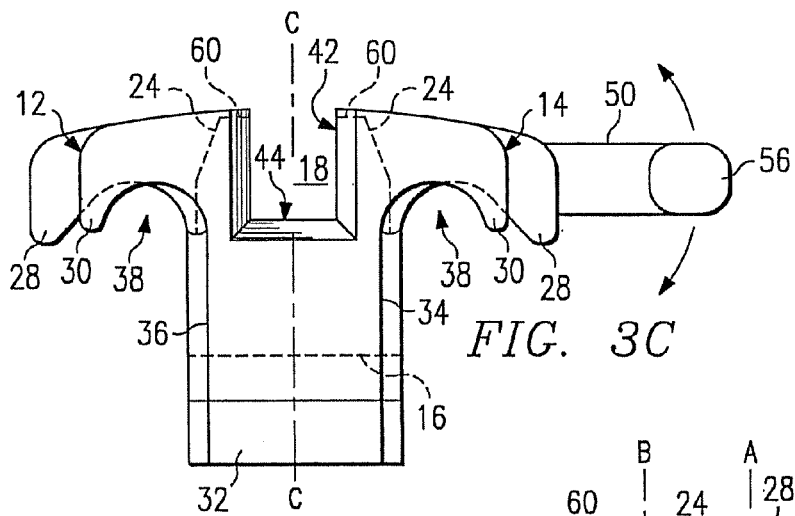
Figure 3B:
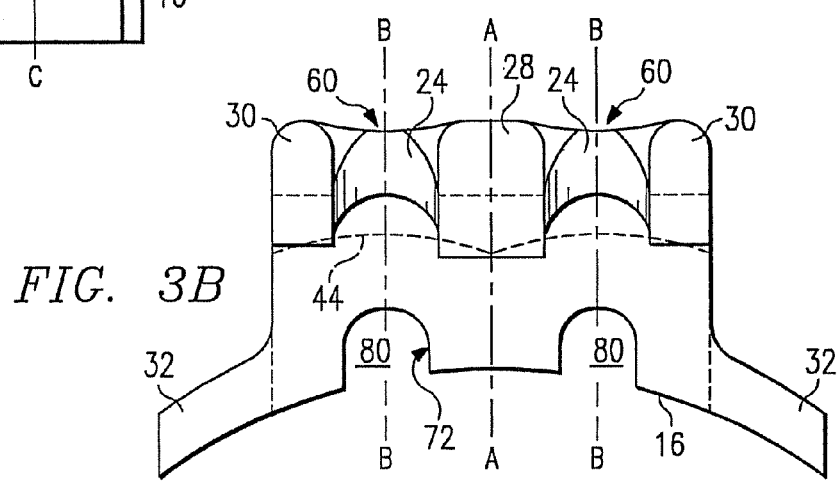

In FIGS. 3A-C an integral T-shaped hook 50 is provided as an extension to the center leg 28 of one of the T-shaped tie wings 12. The T-shaped hook 50 preferably comprises flat lingual and labial surfaces (see FIG. 3C), and is preferably malleable to allow for pivotal movement relative to center leg 20. The T-shaped hook 50 preferably comprises a tapered portion 52, arcuate neck portion 54 and head portion 56, whereby retention of a traction device in neck portion 54 is enhanced.

Twin auxiliary slots 80 may be optionally provided for receipt of an auxiliary device, such as the exemplary auxiliary 74 shown in FIGS. 7A-B. The twin auxiliary slots 80 are beneficially disposed under the convex slot floor portions 44. The configuration of slots 80 and exemplary auxiliary 74 may be as described above to restrict rotational movement therebetween and facilitate placement/removal.

FIGS. 3A-C also illustrate optional saddles 60 which can be provided in the support landing portions 26 for receiving a ligating device. It is believed that such saddles 60 may be beneficial in certain early treatment situations for purposes of retaining an undersized archwire in the desired position for rotational purposes.

In FIGS. 4A-E, the outer sidewall 34 of tie wing 12 and outer sidewall 36 of tie wing 14 define a trapezoid therebetween. Specifically outer side wall 34 is angled relative to the longitudinal center plane CC of the archwire slot 18, and the outer tie wing sidewall 36 is disposed in parallel relation to the center plane CC of the archwire slot 18. By virtue of this arrangement, the outer sidewall 34 may be, for example, advantageously disposed gingivally on partially erupted upper bicuspids. Further, bracket systems employed by this configuration will generally reduce bracket/tooth contact between upper and lower arches.

Figure 4A:
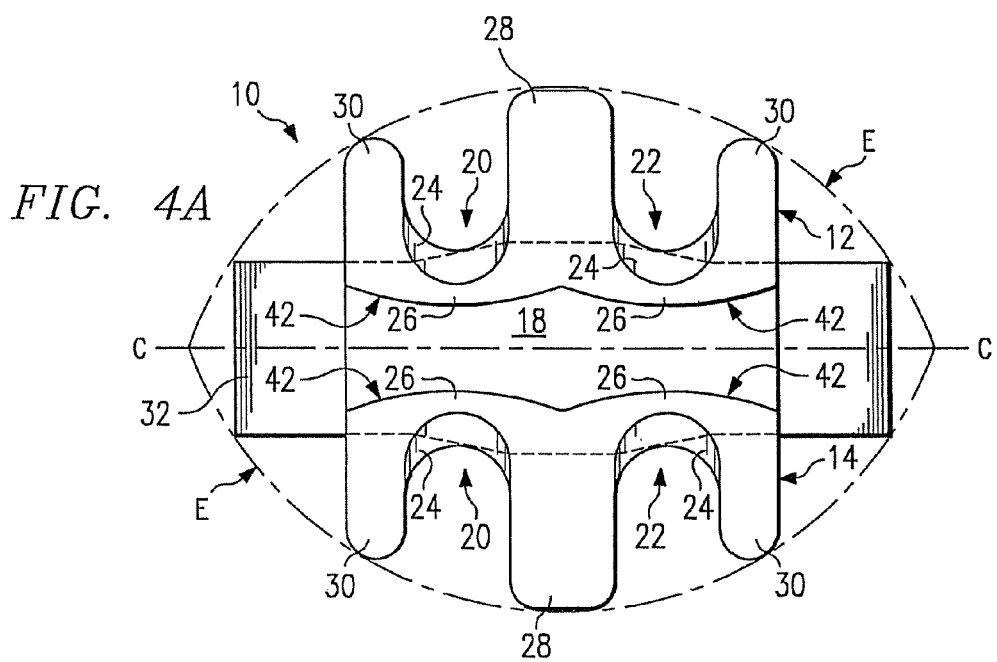
FIGS. 4A-E illustrate labial, side and end views of a modified version of said first embodiment having outer tie wing sidewalls that define a trapezoid therebetween, the end views illustrating various alternative configurations of the base to provide for positive, negative, and no torque on a tooth.
Figure 4C:
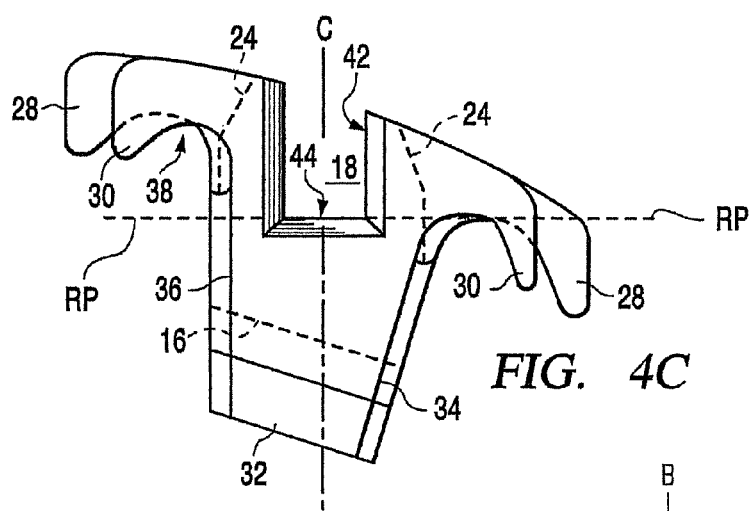
Figure 4B:
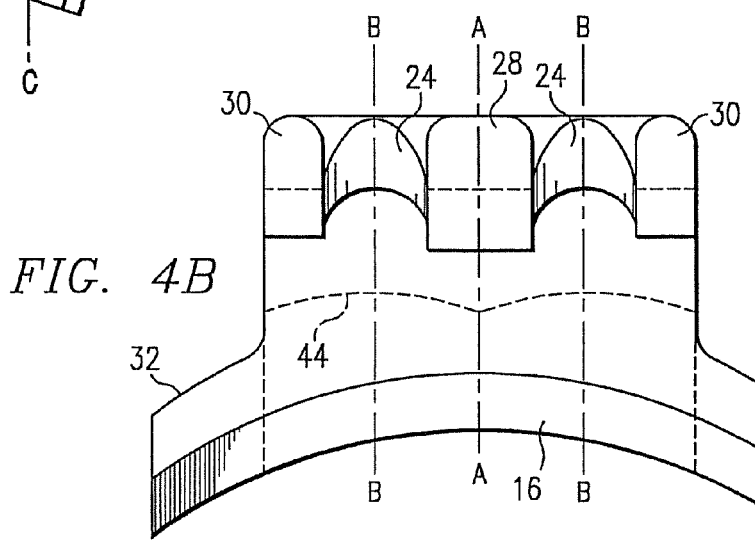
Figure 4D:
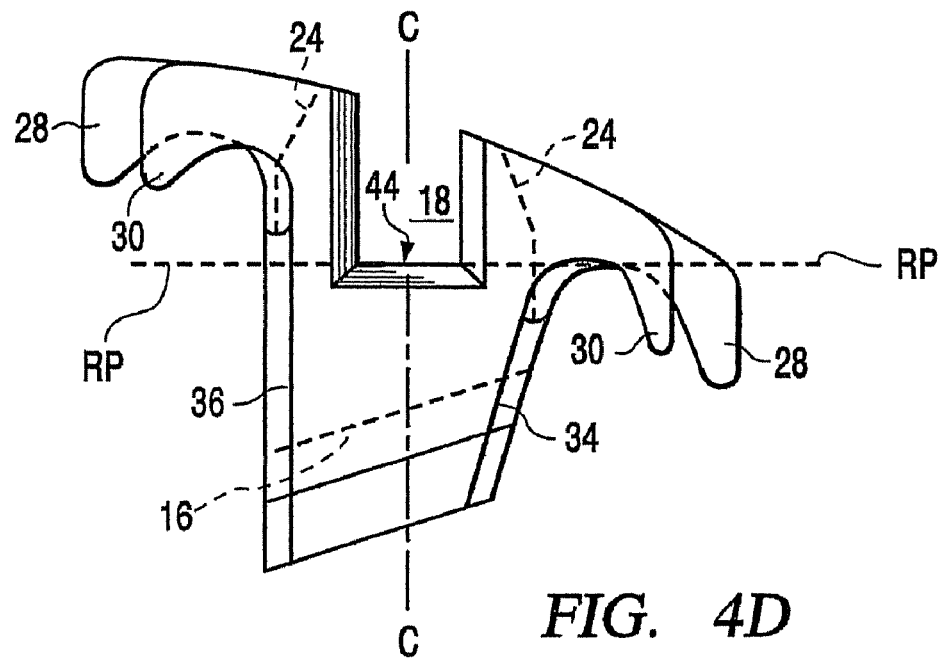
Figure 4E:
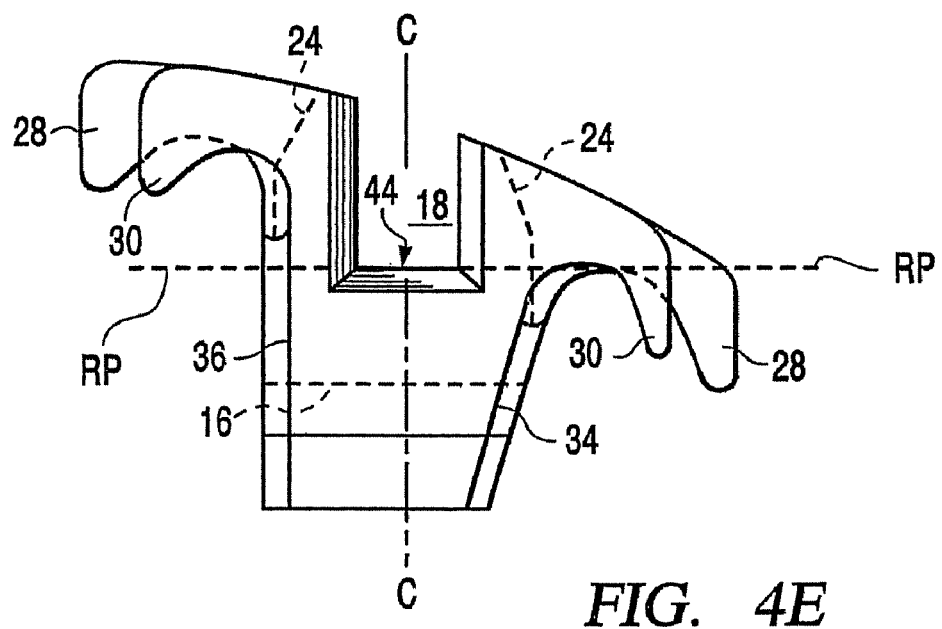

Referring in more detail to FIGS. 4C-E, the trapezoidal configuration of the bracket 10 is illustrated with three alternate configurations for the base portion 16. Generally, the configuration of the base portion 16, namely its occlusal/gingival extent, may be defined in relation to the reference plane RP. As can be seen in FIGS. 4B-E, the reference plane RP coincides with that portion of the bottom or floor of the archwire slot 18 which engages the archwire when positioned therein (e.g., a plane which is tangent to the two convex slot floor portions 44.

The configurations of base portion 16 in FIGS. 4C-E allow a practitioner to provide positive, negative, and no torque on a tooth of a particular orientation. Initially, with the tie wing 34 being gingivally positioned in a maxillary application, the base portion 16 of FIG. 4C would be used to provide for "positive torque" on a tooth, the base portion 16 of FIG. 4D would be used to provide for "negative torque" on a tooth, and the base portion 16 of FIG. 4E would be used to provide for "no torque" on a tooth. More particularly, in the case of the bracket 10 of FIG. 4C the base portion 16 would thereby extend from its gingival edge to its occlusal edge generally toward the reference plane RP in order to properly orient the archwire slot 18 on the orthodontic patient. Moreover, in the case of the bracket 10 of FIG. 4D the base portion 16 would thereby extend from its gingival edge to its occlusal edge generally away from the reference plane RP in order to properly orient the archwire slot 18 on the orthodontic patient. Furthermore, in the case of the bracket 10 of FIG. 4E the base portion 16 would thereby extend from its gingival edge to its occlusal edge generally parallel with the reference plane RP in order to properly orient the archwire slot 18 on the orthodontic patient.

In the event that the tie wing 36 is gingivally positioned in a mandibular application, the base portion 16 of FIG. 4C would provide for "negative torque" on the tooth, the base portion 16 of FIG. 4D would provide for "positive torque" on the tooth, and the base portion 16 of FIG. 4E would provide "no torque" on the tooth.

Figure 5A:
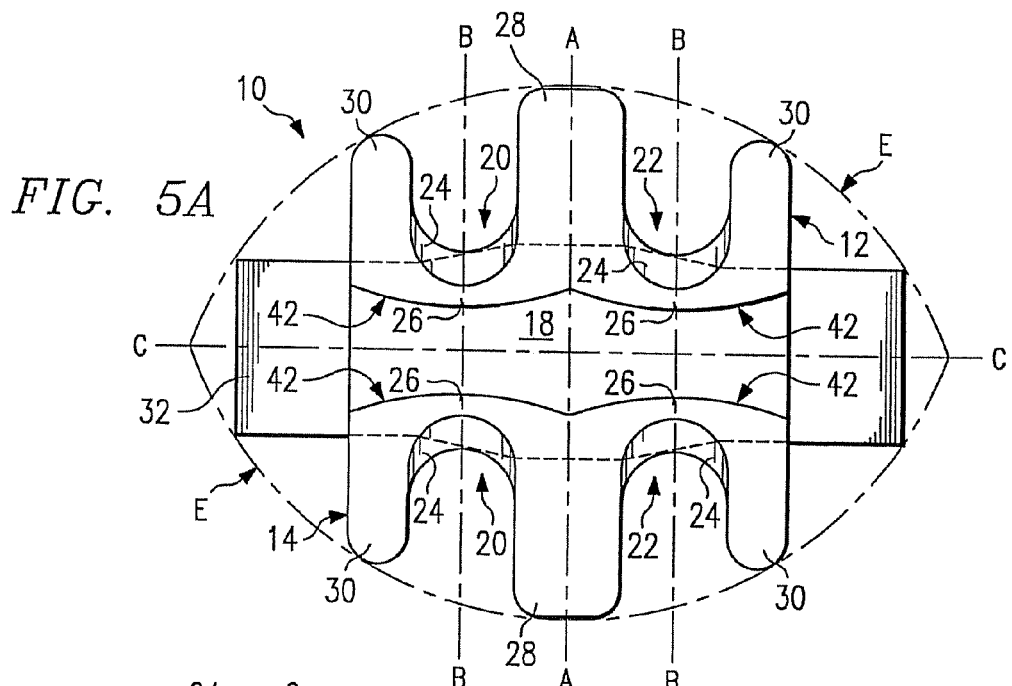
FIGS. 5A-C illustrate labial, side and end views of the modified version of the first embodiment illustrated in FIGS. 4A-C, with a central auxiliary slot.
Figure 5C:
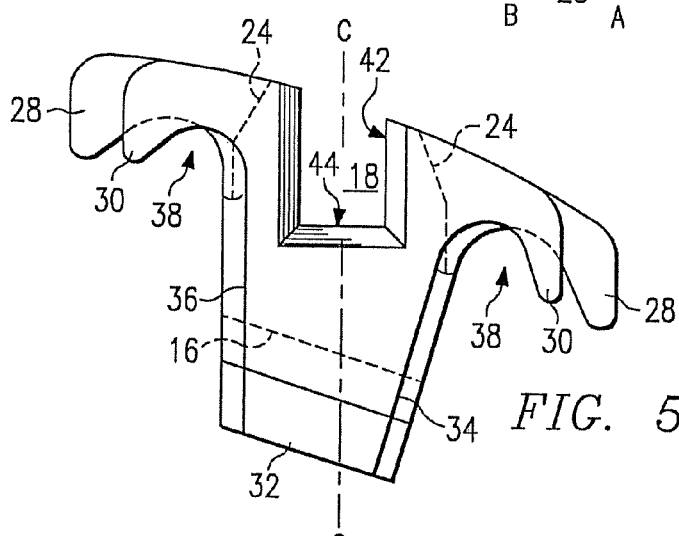
Figure 5B:
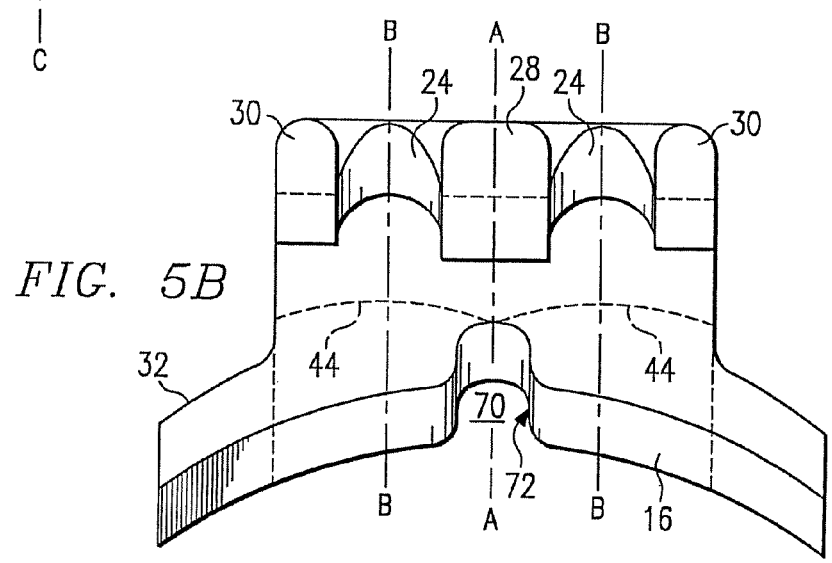

The modified embodiment illustrated in FIGS. 4A-C is shown with additional features in FIGS. 5A-C and 6A-C, although the bracket 10 of FIGS. 4D-E could be similarly modified as well. In FIGS. 5A-C, a central auxiliary slot 70 is provided. However, such an auxiliary slot 70 need not be centrally located along the mesial-distal extent of the bracket. Instead, the auxiliary slot 70 more to the mesial side of the bracket, or more to the distal side of the bracket.

FIGS. 6A-C illustrate the inclusion of twin auxiliary slots 80 for receiving of auxiliary devices. The twin vertical slots 80 are disposed so that each passes under one of the convex slot floor portions 44.

In the version shown in FIGS. 6A-C, it should also be appreciated that the gingival-occlusal center axis of the bracket (lying within plane AA) can be disposed at an acute angle relative to center axis of archwire slot 18 (lying within plane CC). More particularly, center legs 28 may be centered upon the gingival-occlusal center axis and may be provided with distal/mesial surfaces 84 which are parallel to the gingival-occlusal center axis thereby facilitating placement of the bracket. In this modified version, it should be recognized that while the center plane BB of the ligating support means 20 is also disposed parallel to the gingival-occlusal center axis, the apices of the convex slot sidewall portions 42 and convex slot floor portion on each of mesial and distal sides lie in a plane which is perpendicular to the archwire slot center plane CC. Relatedly, it should be appreciated that, when a T-shaped hook is utilized (such as the T-shaped hook 50 illustrated in FIGS. 3A-C above), the center axis thereof will be disposed perpendicularly to the center axis of the archwire slot 18 and at an angle relative to the gingival-occlusal center axis of the bracket 10.

Figure 8:
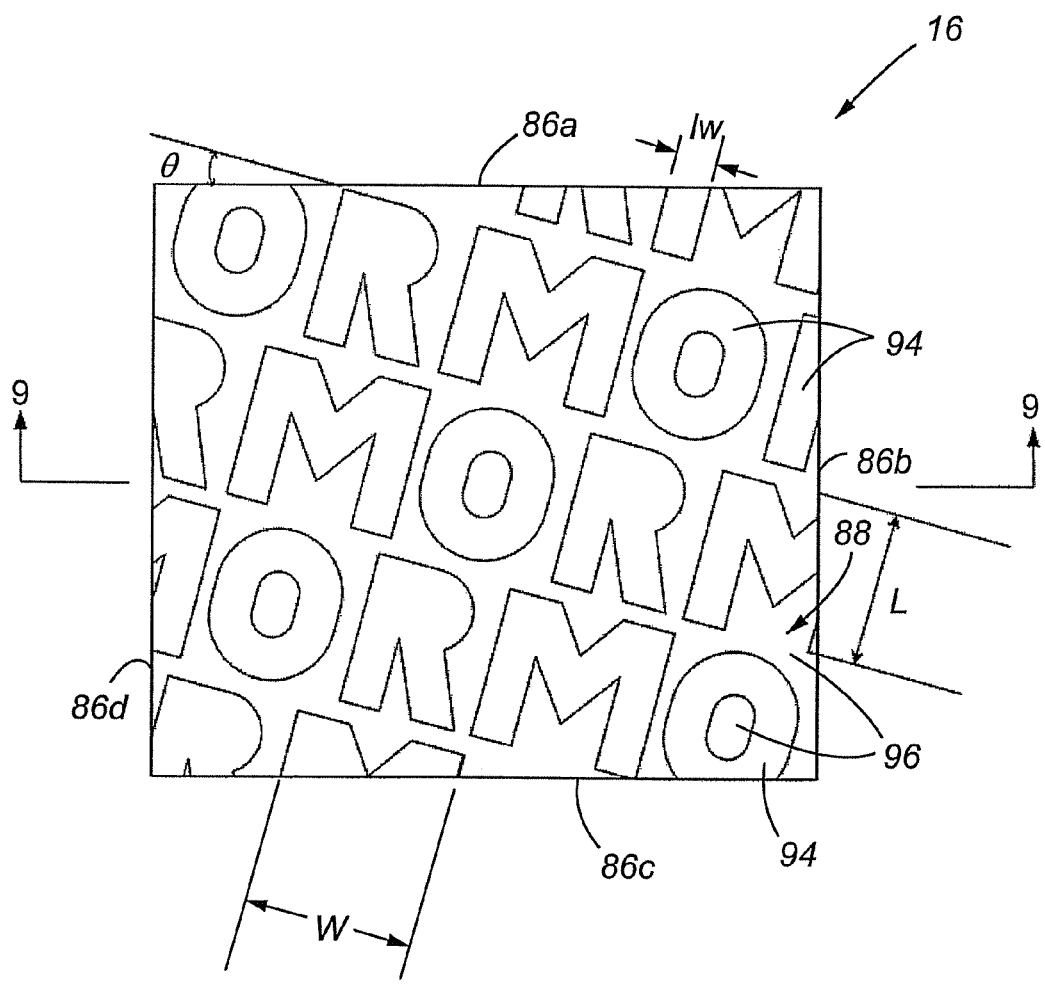
FIG. 8 is a rear view of the base of the orthodontic appliance, e.g., as shown in FIG. 4B without the flanges, and including a character base pattern embedded into the base 16 of the bracket.
Figure 9A:
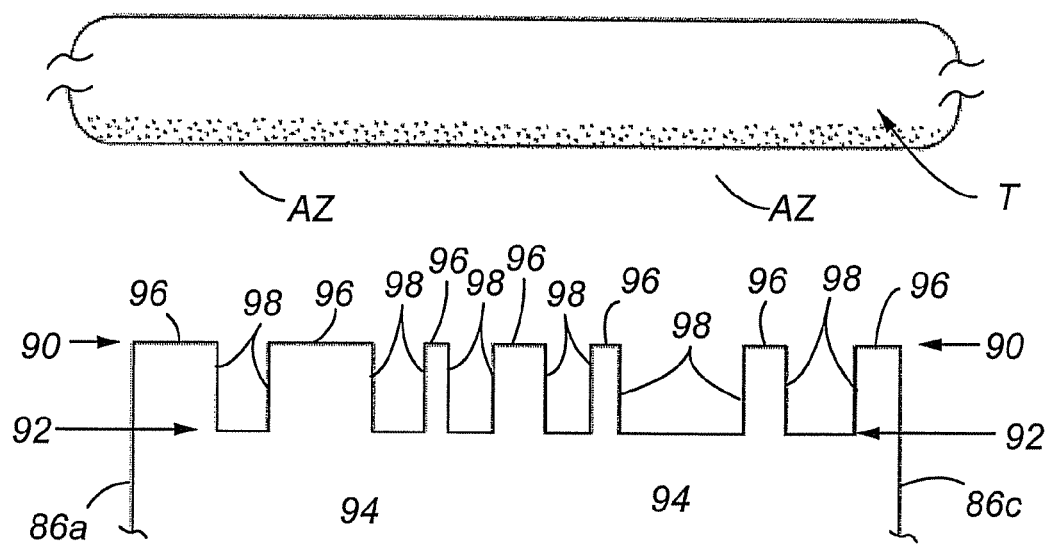
FIG. 9A-B are cross-sections taken along line 9-9 of FIG. 8.
Figure 9B:
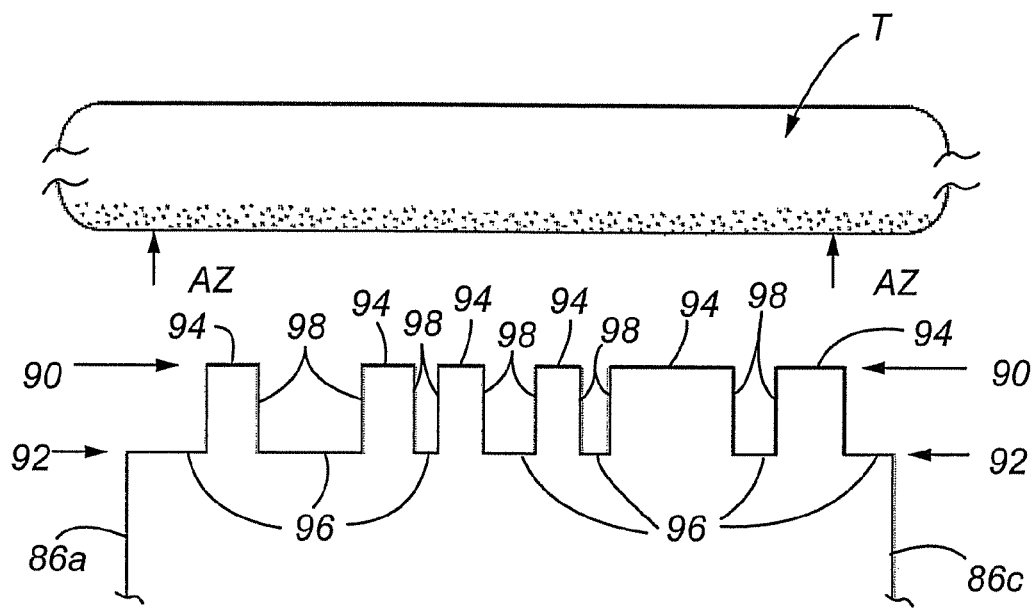

Referring now to FIG. 8, another aspect of the present disclosure is shown. FIG. 8 depicts an enlarged rear elevation view of the rear surface or base 16 of an orthodontic appliance, e.g., the bracket 10, as shown in FIG. 4B, but without flanges 32. Base 16 includes gingival edge 86a, distal edge 86b, occlusal edge 86c, and mesial edge 86d. Within the interior of edges 86a, 86b, 86c, and 86d is interior region 88. As depicted in FIGS. 9A and 9B, interior region 88 includes at least one projected surface 90 and at least one recessed surface 92. The projected surface 90 of the interior region 88 is a surface that is both substantially parallel to the tooth's surface and closest to the tooth's surface upon attachment of the orthodontic appliance, e.g., the bracket 10 to the tooth. The recessed surface 92 is a surface of the interior region 88 that is also substantially parallel to the tooth's surface, but is further away from the tooth's surface than the projected surface 90 upon attachment of the orthodontic appliance, e.g., the bracket 10 to the tooth. The recessed surface 92 is preferably recessed between about 0.009 to 0.012 inches relative to the projected surface 90, and more preferably, the recessed surface is recessed about 0.010 inches relative to the projected surface 90.

Characters 94 (e.g., FIG. 8) and intermediate space 96 extend substantially continuously within interior region 88, between edges 86a, 86b, 86c, and 86d. The pattern of characters 94 may be repeating, such as the letters "RMO" ® shown in FIG. 8, or they may be a non-repeating series of characters 94. Alternately, the characters may be a set of information regarding the orthodontic appliance, such as:

(i) its intended installation location such as characters representing tooth location, e.g., the characters "CENT" for identifying the installation location as a central tooth, "BIC" for identifying the installation location as a cuspid tooth, "MOL" for identifying the installation location as a molar; alternatively/optionally, such tooth locations may be identified by tooth number such as the number "8" identifies the maxillary right central tooth; alternatively/optionally, such tooth locations may be identified by Palmer Location, e.g., the symbols ⌐ identify the maxillary left cuspid, (ii) its manufacturer, (iii) its date of manufacturer, (iv) its model number, (v) its location of manufacture, (vi) instructions or suggestions regarding use of the orthodontic appliance, (vii) a patent number for the orthodontic appliance, (viii) a logo, a trademark for the orthodontic appliance, (ix) a pattern that may be optically scanned for obtaining information on the orthodontic appliance (e.g., any of the informational items (i) through (viii) hereinabove), etc.

Figure 21:
FIG. 21 shows the base 16 of an orthodontic application having a body 8, wherein information is encoded into the base by, e.g., molding, and in particular, providing the characters 94 as raised or projected portions of the base 16.
Figure 22:
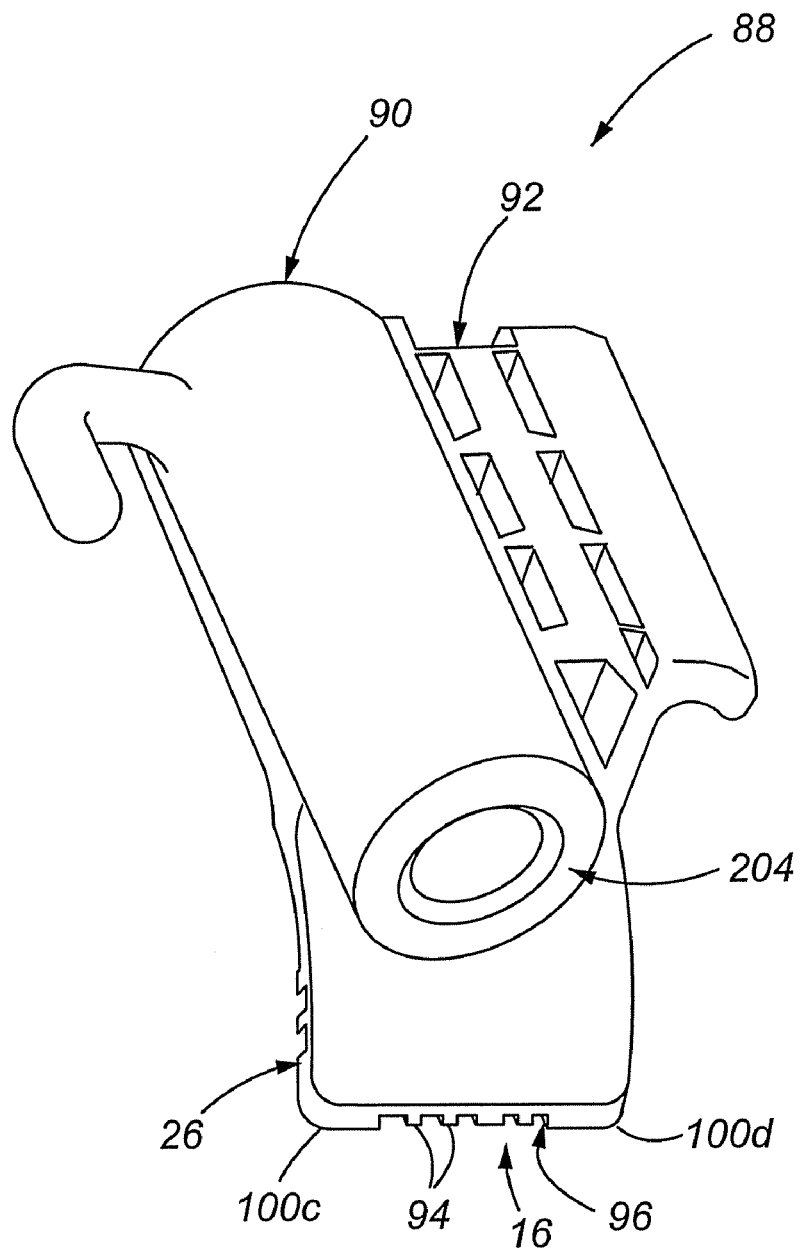
FIGS. 22 through 27 show various orthodontic appliances with bases 16 having encoded information embedded or formed in the bases, wherein the characters 94 are on the projected surface(s) 90 (e.g., as shown in FIGS. 9A and 9B), and the intermediary space 96 between the characters is provided on the recessed surface(s) 92 (e.g., as shown in FIGS. 9A and 9B).
Figure 23:
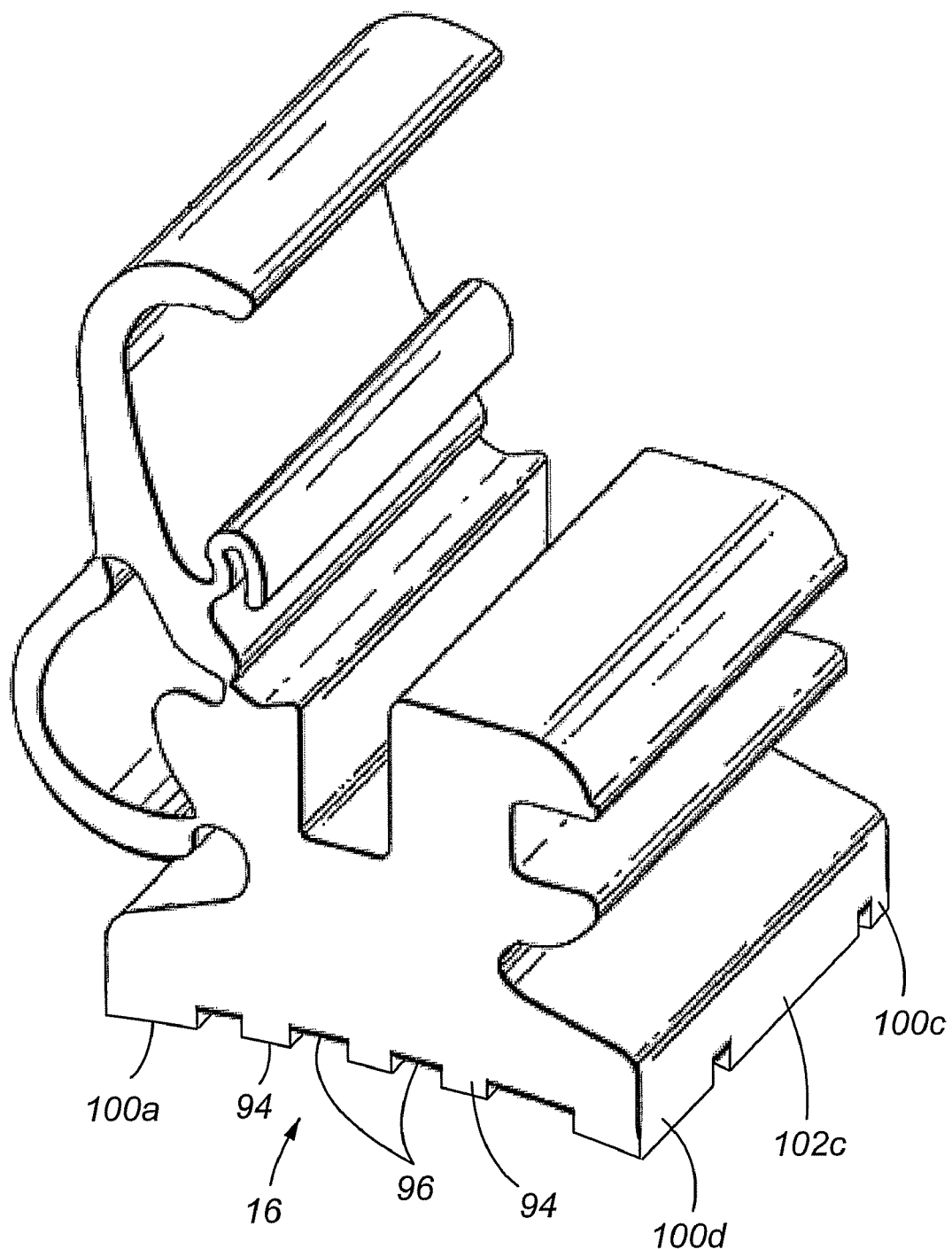
Figure 24:
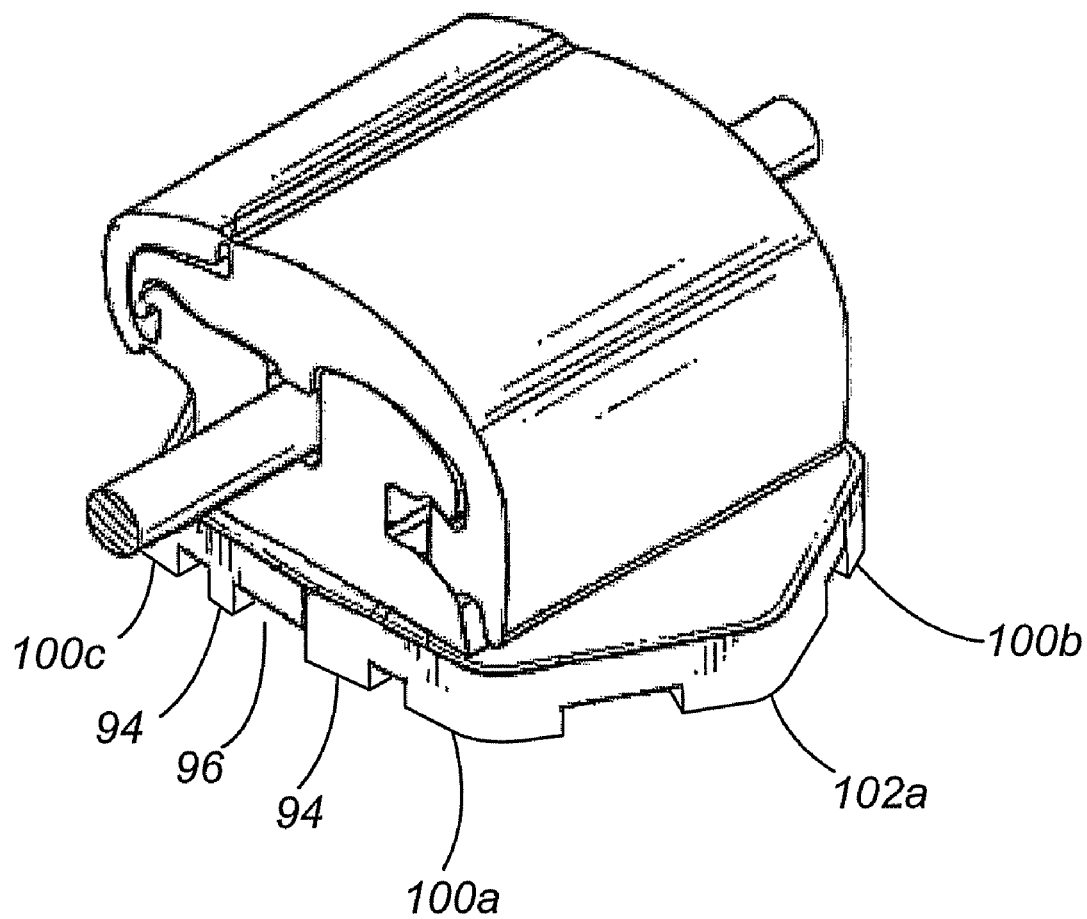
Figure 25:
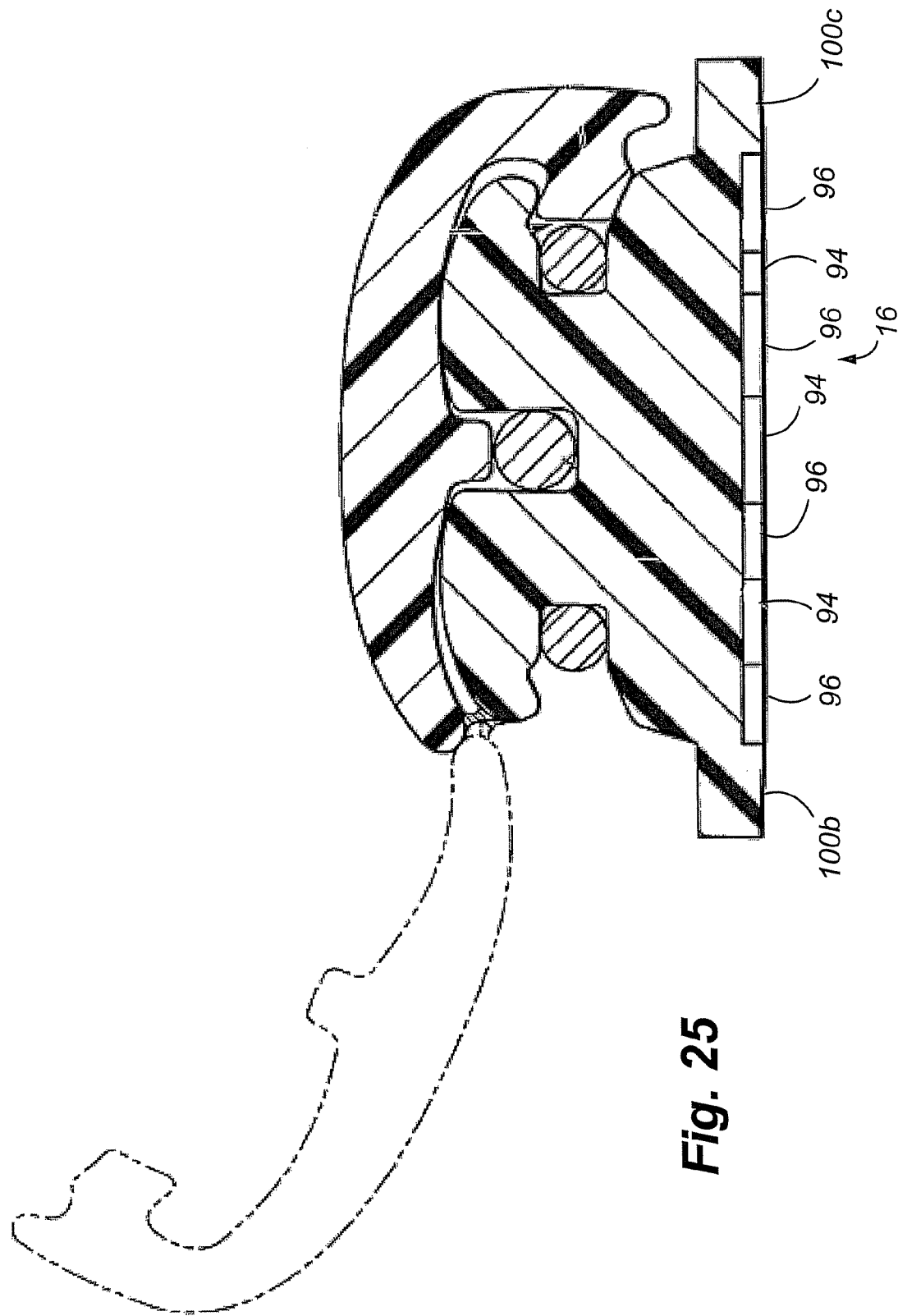
Figure 26:
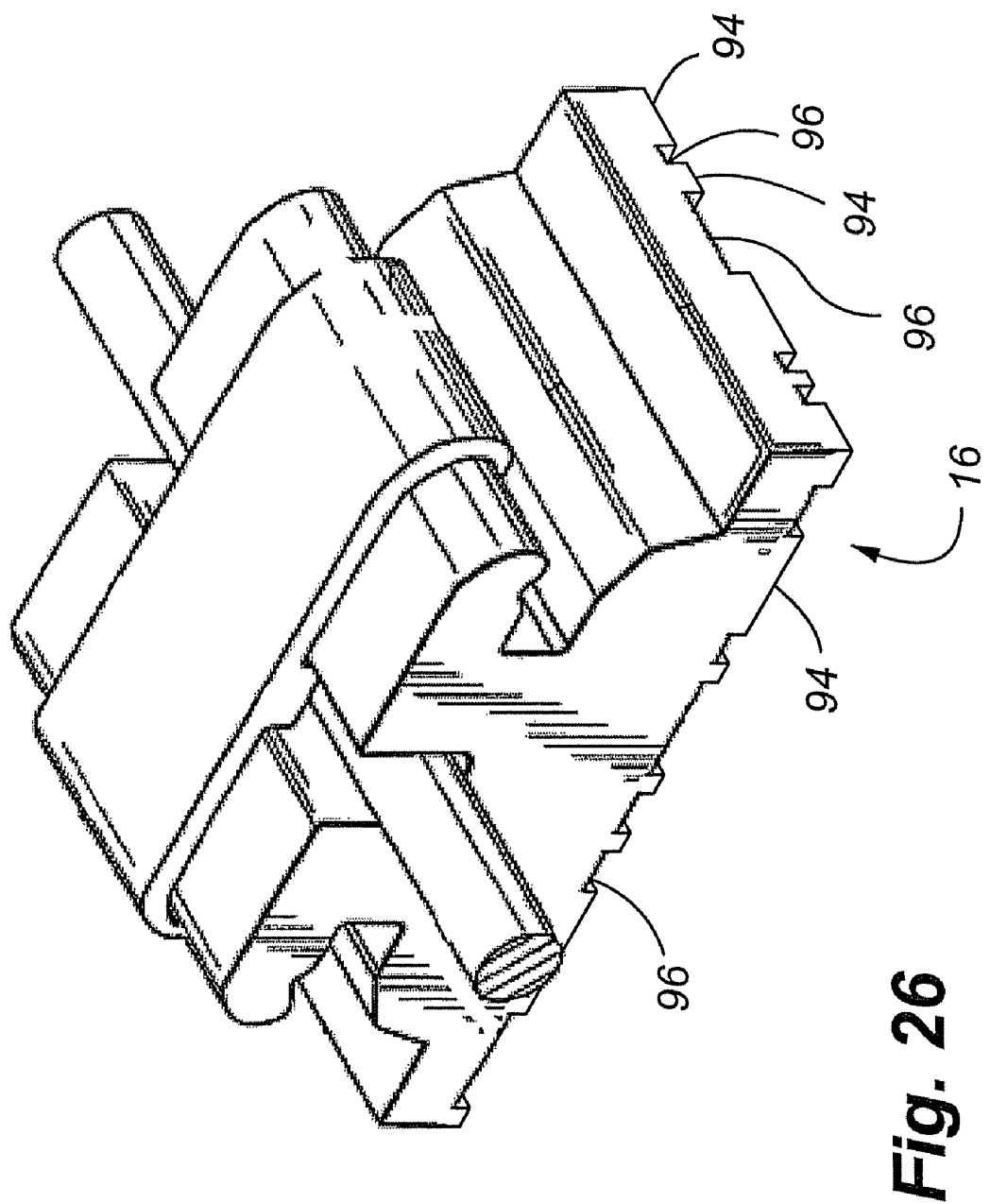
Figure 27:
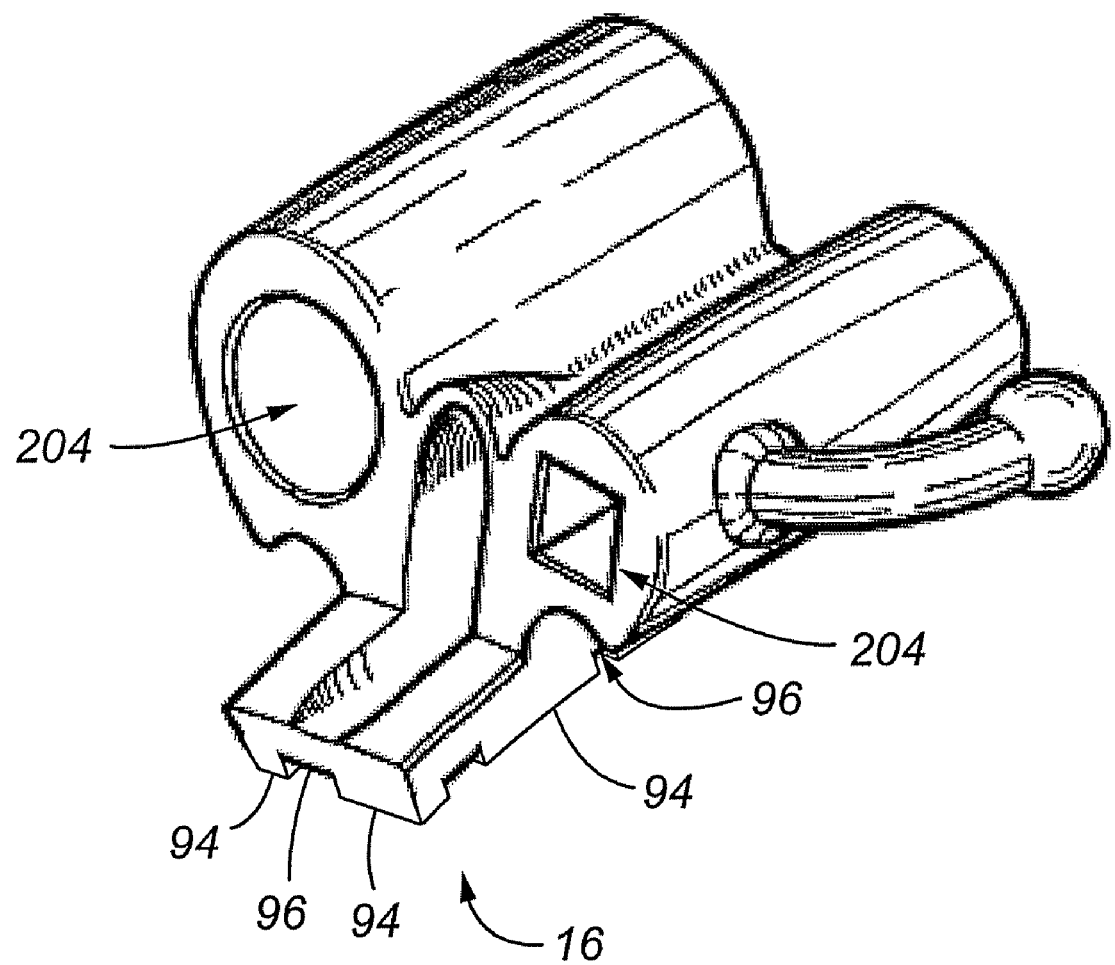

An example, of such a set of information is illustrated in FIG. 21, wherein the base 16 of the orthodontic appliance shown in this figure includes a series of projected characters 94 providing the following information encodings (from left to right and top to bottom):

the characters "RMO" identify the supplier of the orthodontic appliance as RMO, Inc., the "X" is a separation character, the characters "TS54" identify model of an orthodontic tube, the characters "072407" identify the date of manufacture, the characters "CUS" identify the location of manufacture as Colorado in the U.S., the characters "B46" identify the batch of material(s) from which the orthodontic appliance was created, and the "X" is a separation character, and the characters "IV6" identifies the version of the documentation that is to be supplied to an orthodontist with the appliance.

As one of skill in the art will appreciate, the provision of such information on the base of an orthodontic appliance performs a useful function with respect to the use of the device, and tracing the source and time of manufacturer in the event of a defective appliance, and/or a recall may be necessary.

Note that the separation character (e.g., "X" hereinabove) may be optionally used or not used depending the amount of information to be embedded in the base 16. If, e.g., only the first row of information in FIG. 21 were to be embedded in a base 16 of an orthodontic appliance, then the separation character may be used to fill up any additional space remaining on the base 16. That is, an important aspect of such embedding of information is to not only provide information on the appliance, but also substantially increase the base area (such area including the areas of the walls 98 (e.g., FIG. 15A described hereinbelow) separating the projected portions of the base 16 from the recessed portions of the base) to which an adhesive can adhere. Accordingly, it can be important that such characters be chosen so that the base area increases, e.g., at least 30% and preferably 40% or more over a substantially two dimensional, e.g., flat or convex, base 16. Thus, a character such as "X" provides more wall 98 surface area for adhesive adherence than, e.g., the hyphen symbol "-", and accordingly "X" is generally preferable.

Figure 28:
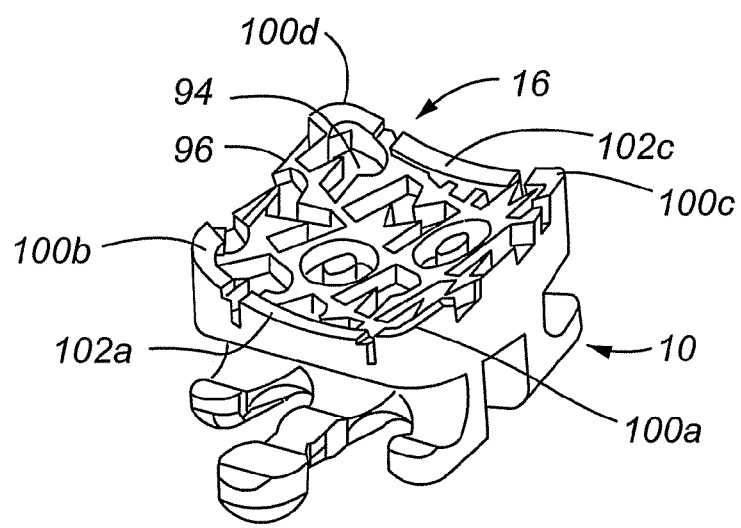
Figure 29:
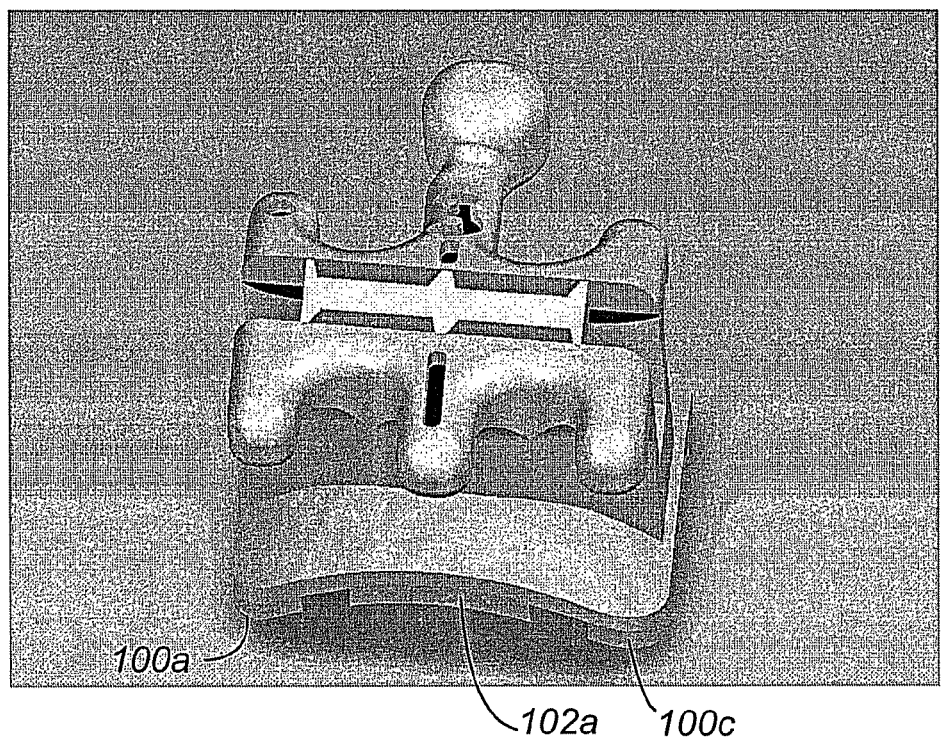
Figure 30:
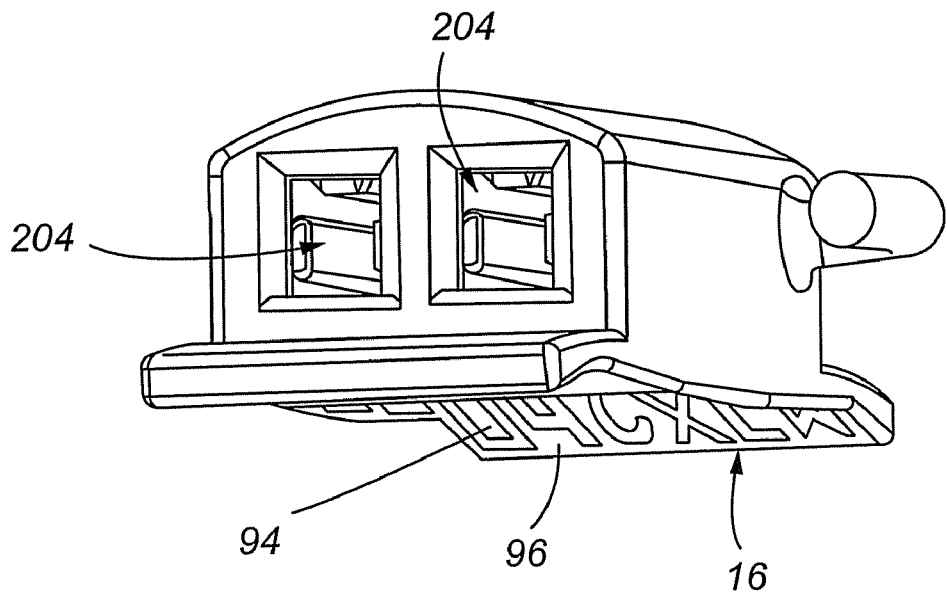
Figure 31:
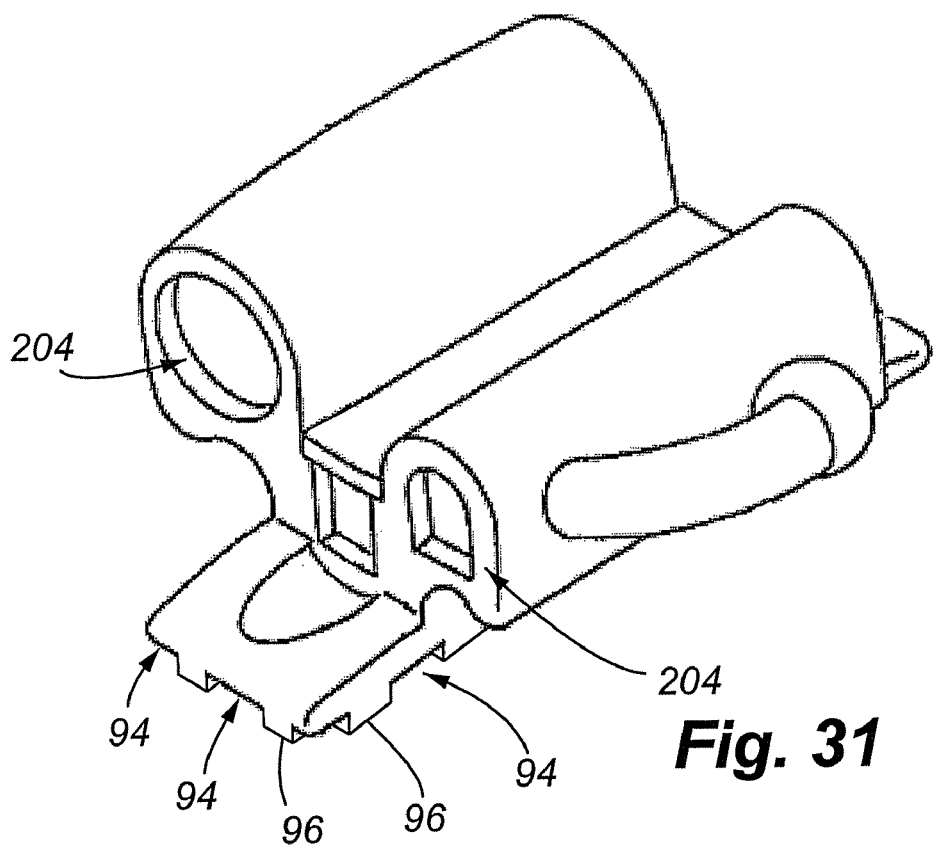
Figure 32:
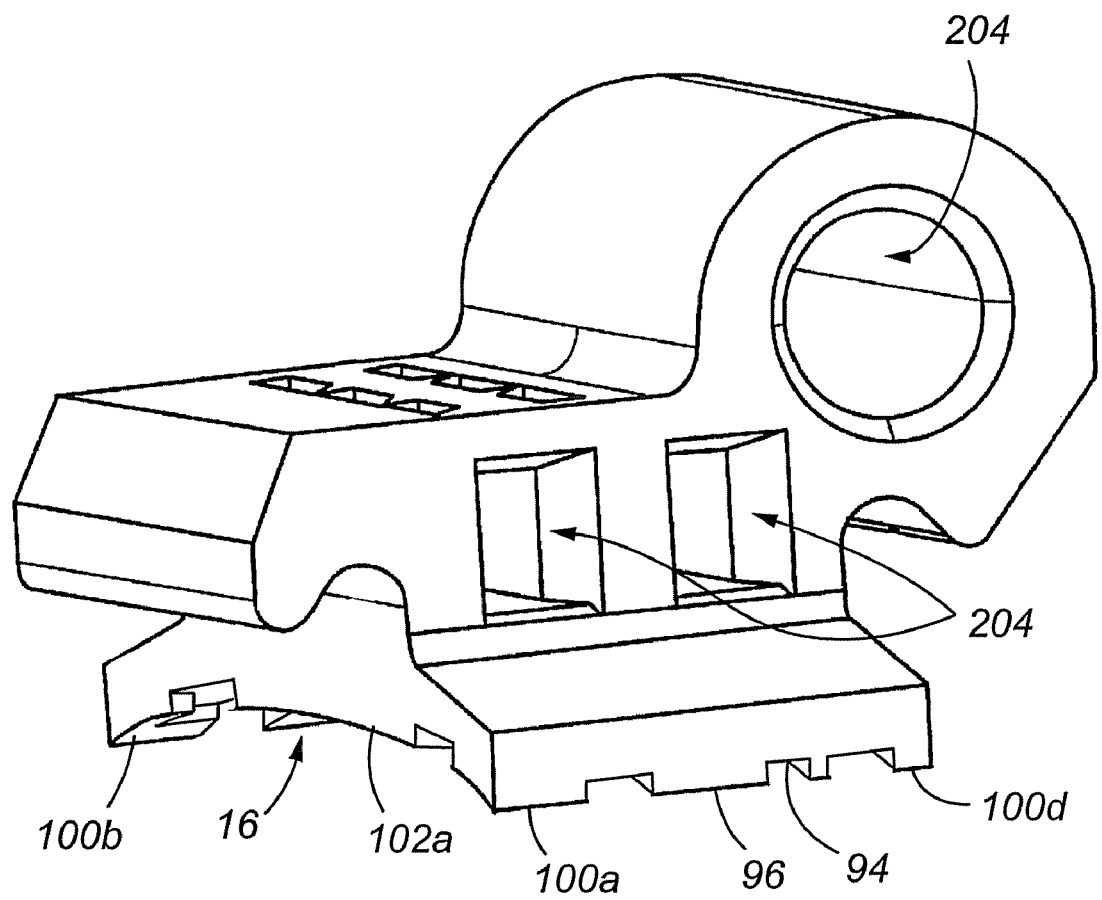
Figure 33:
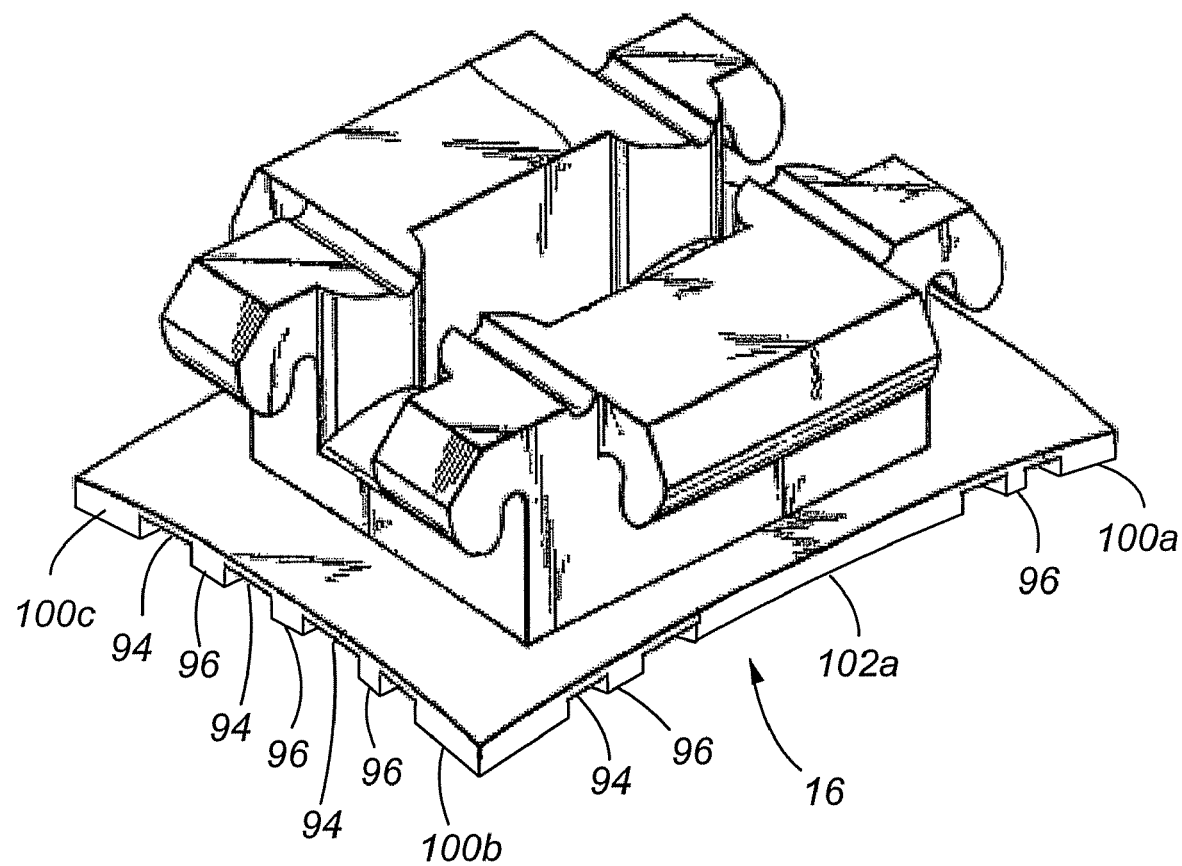
Figure 34:
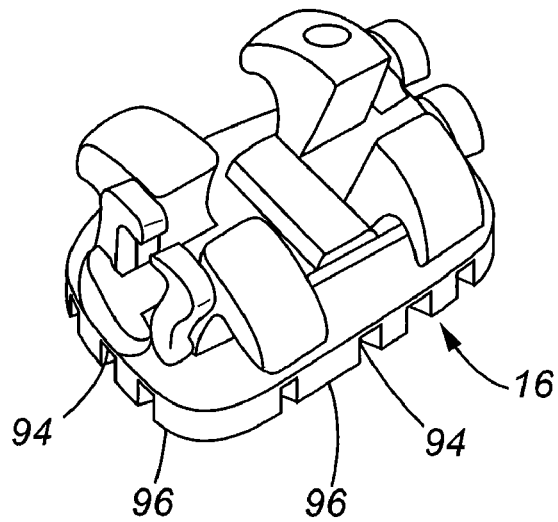
Figure 35B:
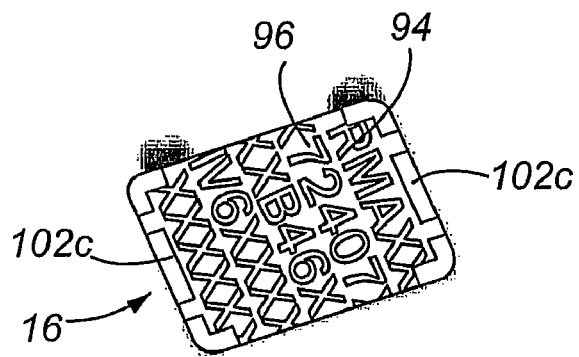
Figure 35A:
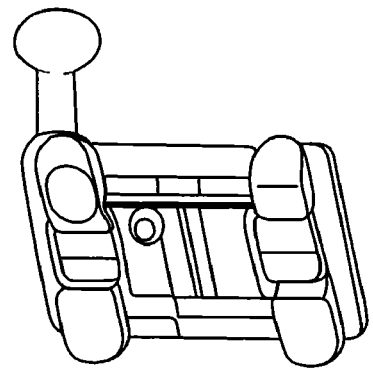
Figure 36:
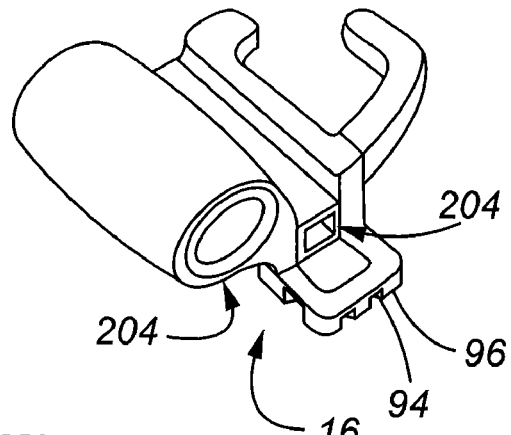
Figure 37:
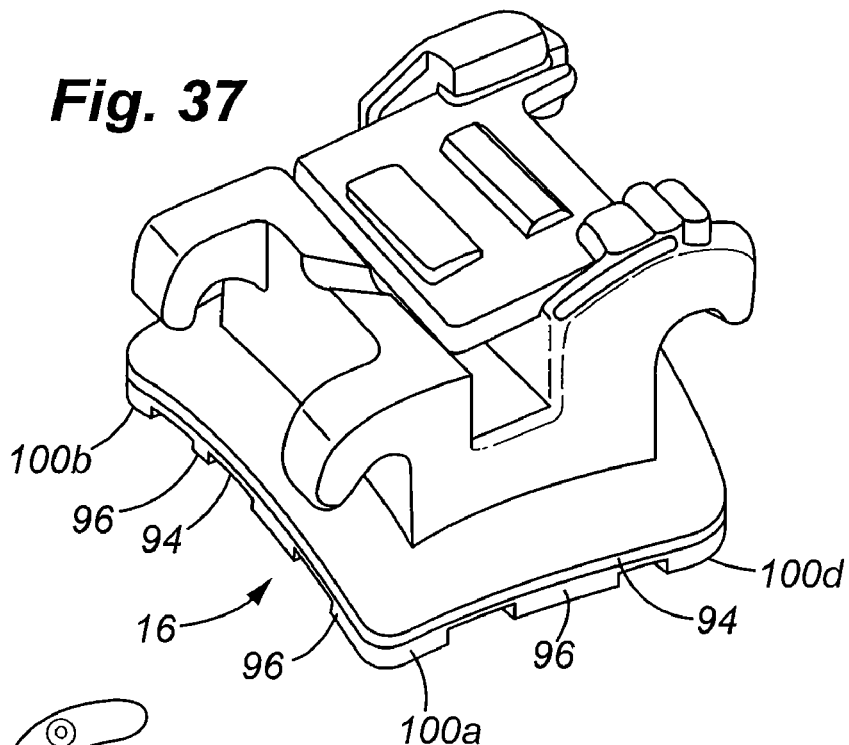
Figure 38:
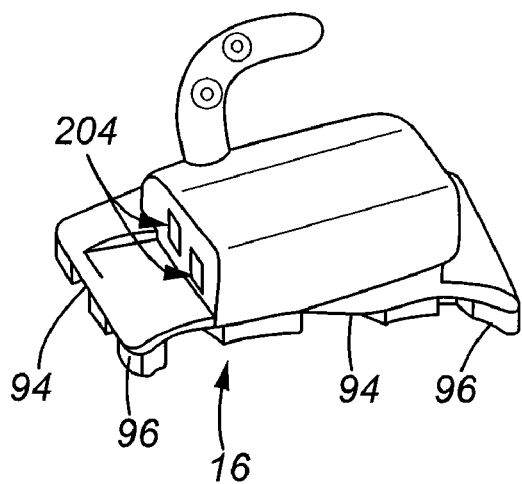
Figure 39:
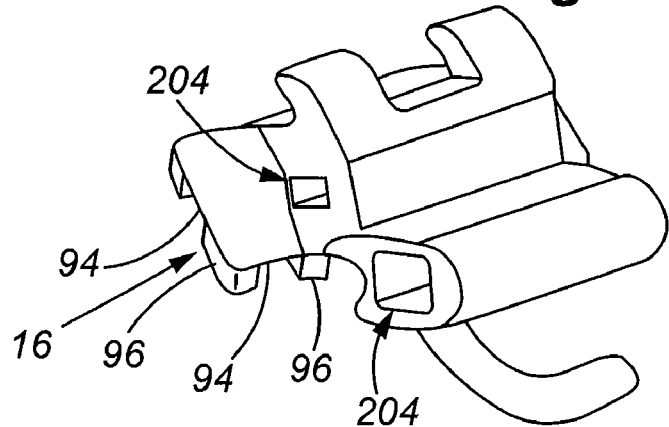

It is also important to bear in mind that there is a limitation on the depth of the most recessed base surface 92 relative to the more projected surface 90 (correspondingly, the extent of the walls 98 spanning between base surface levels), is limited in that as this depth increases, if the thickness of the body 8 of the orthodontic appliance extending away from its attached tooth does not correspondingly increase, then the orthodontic appliance can weaken. Accordingly, for at least most of the walls 98, the extent of the wall is between about 0.009 to 0.011 inches in depth, and more preferably, such walls span between the projected surface 92 and the recessed surface in a range of 0.010±0.0005 inches, this last range being particularly advantageous. However, it is within the scope of the present disclosure that there may be more than one level of recessed surface. In particular, the levels of recessed surfaces may roughly follow a curve for providing a uniform thickness of the body 8, and/or for providing at least a minimal orthodontic body thickness between each recessed surface and its corresponding appliance exterior surface facing away from the tooth to which the appliance is attached. Alternatively/optionally, the levels of recessed surfaces may roughly follow a curve of the base itself as shown in FIG. 28. Moreover, it is also within the scope of the definition of walls 98 that such walls may not be orthogonal to one or more of the surfaces 90 and 92. In particular, walls 98 may be at an incline of 45 degrees or greater relative to one or more of the surfaces 90 and 92.

Regardless of the nature of the characters 94 actually used, in a preferred embodiment, the base 16 does not have a grid between the characters 94. That is, in contrast to the bracket base shown in FIG. 13 of U.S. Pat. No. 5,595,484, the base 16 of the present disclosure does not have a grid or lattice within which the characters reside. Rather, the present disclosure describes providing characters 94 and a relatively irregular, non-grid like intermediate space 96 to cover the entire interior region 88. The characters 94 and intermediate space 96 thus function directly as the texturing that works in combination with the adhesive to more effectively bond the bracket to the tooth.

In a separate aspect of the present disclosure, the characters 94 may be angled at any orientation relative to the edges 86a, 86b, 86c, and 86d. More specifically, the characters may be oriented parallel with edges 86a and 86c, or perpendicular to edges 86a and 86c. Likewise, the characters may be oriented parallel with edges 86b and 86d, or perpendicular to edges 86b and 86d. Alternately, the characters 94 may be oriented at an angle relative to edges 86a, 86b, 86c, and 86d. As an example without limitation, FIG. 8 illustrates that the characters 94 are oriented at an angle θ of about 15 degrees relative to edges 86a and 86c, and at an angle of about 75 degrees relative to edges 86b and 86d.

Character length "L" and width "W" may vary considerably. Referring again to FIG. 8, in a preferred embodiment, in plan view, the length L of each characters 94 is about 0.034 to 0.040 inches, and more preferably, about 0.036 inches. The width W of each character 94 varies with the length and with the specific character type. For example, in the character string "RMO" ® shown in FIG. 8, an "M" is typically wider than an "R" or an "0".

For each character 94, the line width "lw" preferably ranges between about 0.008 to 0.010 inches, where line width lw is the width of the line forming each individual character 94. Typically, line width lw will vary with character length L. Therefore, shorter characters 94 will typically have thinner line widths lw. Obviously, logos, and other symbols as well as certain graphics will have lengths L, widths W, and line widths lw as required to form each individual type of shape.

For each orthodontic appliance of the present disclosure, the total base surface area of the appliance is defined herein as the area between the edges of the appliance base 16 (e.g., edges 86a, 86b, 86c, and 86d of FIG. 8) for the base surfaces that are substantially parallel or non-parallel to the tooth's surface when the orthodontic appliance is applied to the tooth, wherein the non-parallel surfaces are the walls 98, and 99, FIG. 21 as described hereinbelow. The total two dimensional surface area is defined herein as total surface area of the base that is substantially parallel to the tooth when the orthodontic appliance is applied to the tooth. Accordingly, the total two dimensional base surface is substantially the sum of the recessed surface 92 area, and the projected surface 92 area. Thus, if the base 16 is rectangular and two dimensional, the total two dimensional base surface area is just the length of the base 16 multiplied by the width of the base 16. However, since the base 16 is generally curved to approximate the curvature of a tooth to which it is to be attached, the total two dimensional base surface area is greater than the length of the base 16 multiplied by the width of the base 16. Whether the characters 94 are letters, numbers, logos, symbols, or graphics, preferably the recessed surface 92 comprises between about 50% to 60% of the total two dimensional base surface area of the base 16, and more preferably, about 55% of the total two dimensional base surface area of base 16. Correspondingly, preferably the projected surface 90 comprises between about 40% to 50% of the total two dimensional base surface area of the base 16, and more preferably, about 45% of the total two dimensional base surface area of the base 16.

Projected surface 90 (e.g., FIG. 9A) and recessed surface 92 are comprised of characters 94 and intermediate space 96, which is situated between and around characters 94. Characters 94 may occupy the projected surface 90 of the base 16, but preferably occupy the recessed surface 92 of the base 16. Alternatively, intermediate space 96 may occupy the recessed surface 92 of base 16, but preferably occupy the projected surface 90 of base 16. However, in a preferred embodiment, upon attachment of the bracket 10 to the surface of a patient's tooth, intermediate space 96 is the projected surface 90 that is closer to the tooth surface than the characters 94 that are situated along the recessed surface 92. Separation between the characters 94 and intermediate space 96 is formed by bracket character walls 98 that are generally perpendicular or steeply sloped surfaces disposed between the characters 94 and the intermediate space 96. As shown in FIG. 9A, the projected surface 90 contacts the tooth surface upon attachment of the bracket 10 in the direction of arrows A2 to the patient's tooth T. Thus, as shown in FIG. 9A, when the intermediate space 96 occupies the projected surface 90, the intermediate surface 96 is closest to the tooth surface, and the location of characters 94 is recessed relative to the location of intermediate space 96. In contrast, FIG. 9B presents the same cross-sectional view of base 16 as that shown in FIG. 9A, but with the characters 94 and intermediate space 96 inverted. That is, in this modified arrangement, the location of intermediate space 96 is recessed relative to the location of the characters 94. Therefore, the characters 94 contact the tooth surface upon attachment of the bracket 10 in the direction of arrows A2 to the patient's tooth T.

Figure 10:
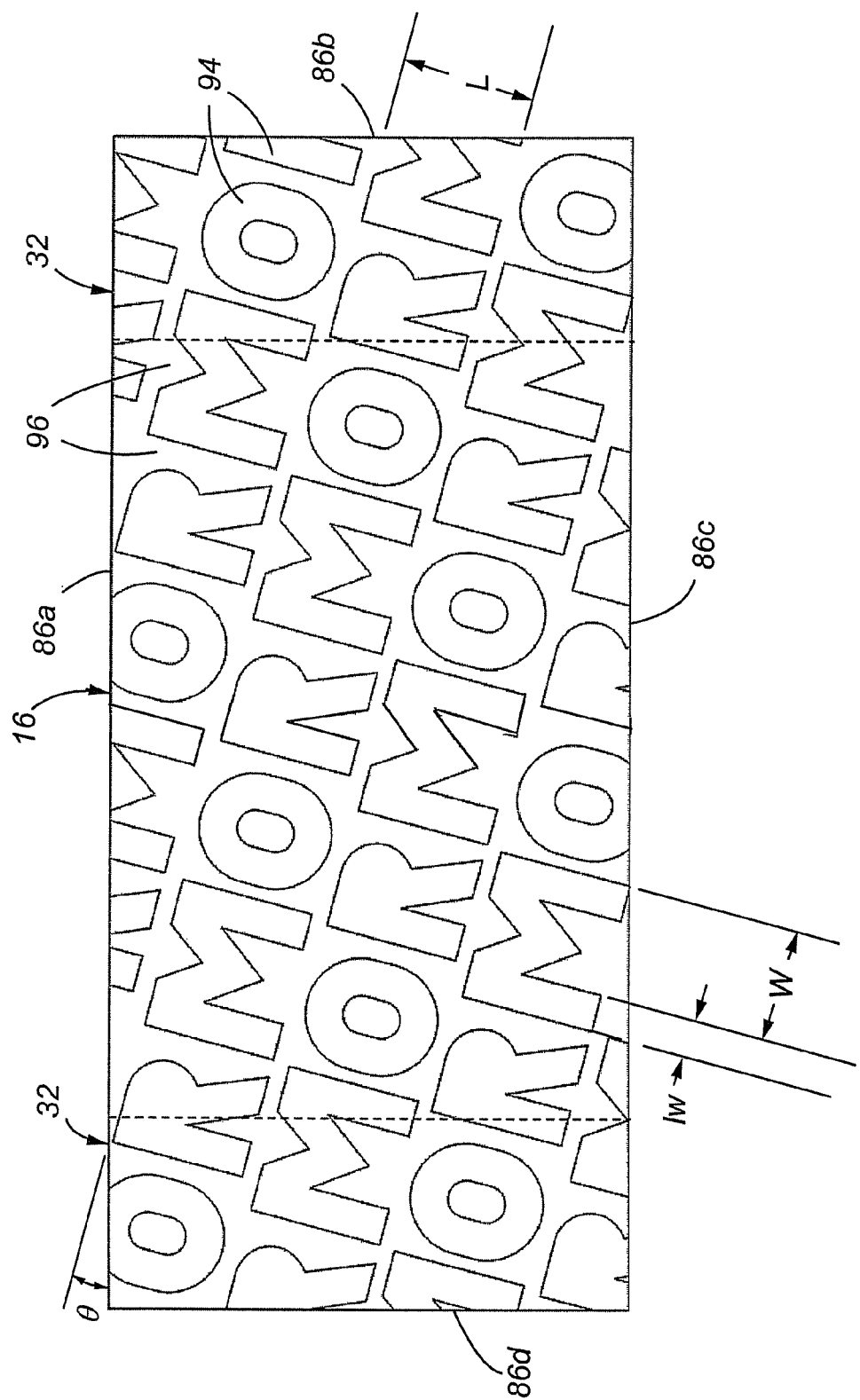
FIG. 10 is a rear or underneath view of the base 16 of an orthodontic appliance, e.g., the bracket shown in FIG. 4B with the flanges, and including a character base pattern.

Referring now to FIGS. 4B and 10, a bracket 10 with a continuous and uninterrupted base 16 and flanges 32 is shown. When flanges 32 are incorporated into the base 16 having characters 94, the characters 94 are preferably extended across the entire rear surface of the bracket 10. Preferably, the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 and the flanges 32, and more preferably, about 55% of the total two dimensional surface area of base 16 and the flanges 32. Correspondingly, preferably the projected surface 90 comprises between about 40% to 50% of the total two dimensional surface area of the base 16 and the flanges 32, and more preferably, about 45% of the total two dimensional surface area of the base 16 and the flanges 32. These preferred values have been found to provide better adhesion characteristics between the bracket and the tooth to which it is applied.

Figure 11A:
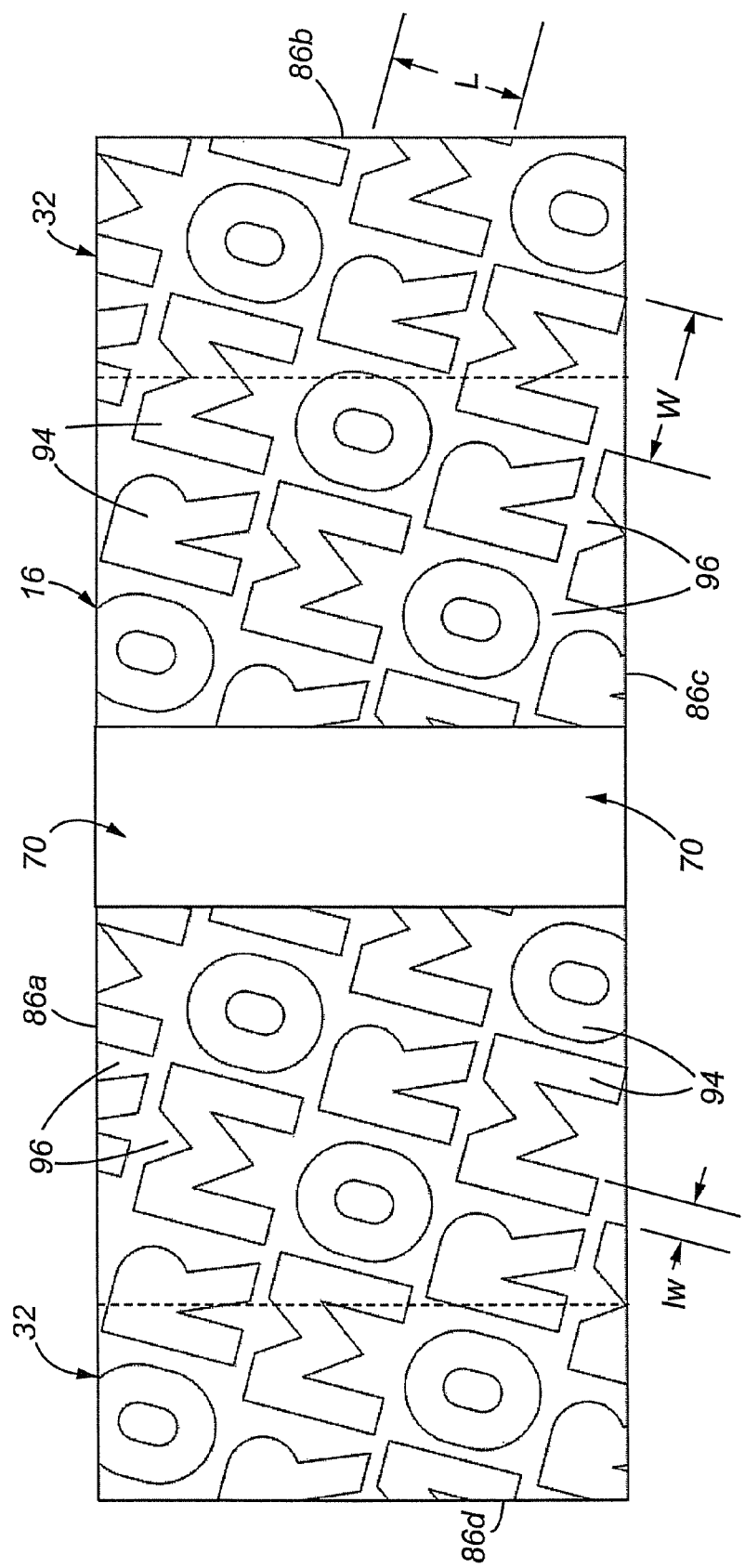
FIG. 11A shows the base of an orthodontic appliance, e.g., the bracket 10 shown in FIGS. 1B and 5B with the flanges, and including a character base pattern and an auxiliary slot without a character pattern in the auxiliary slot.
Figure 11B:
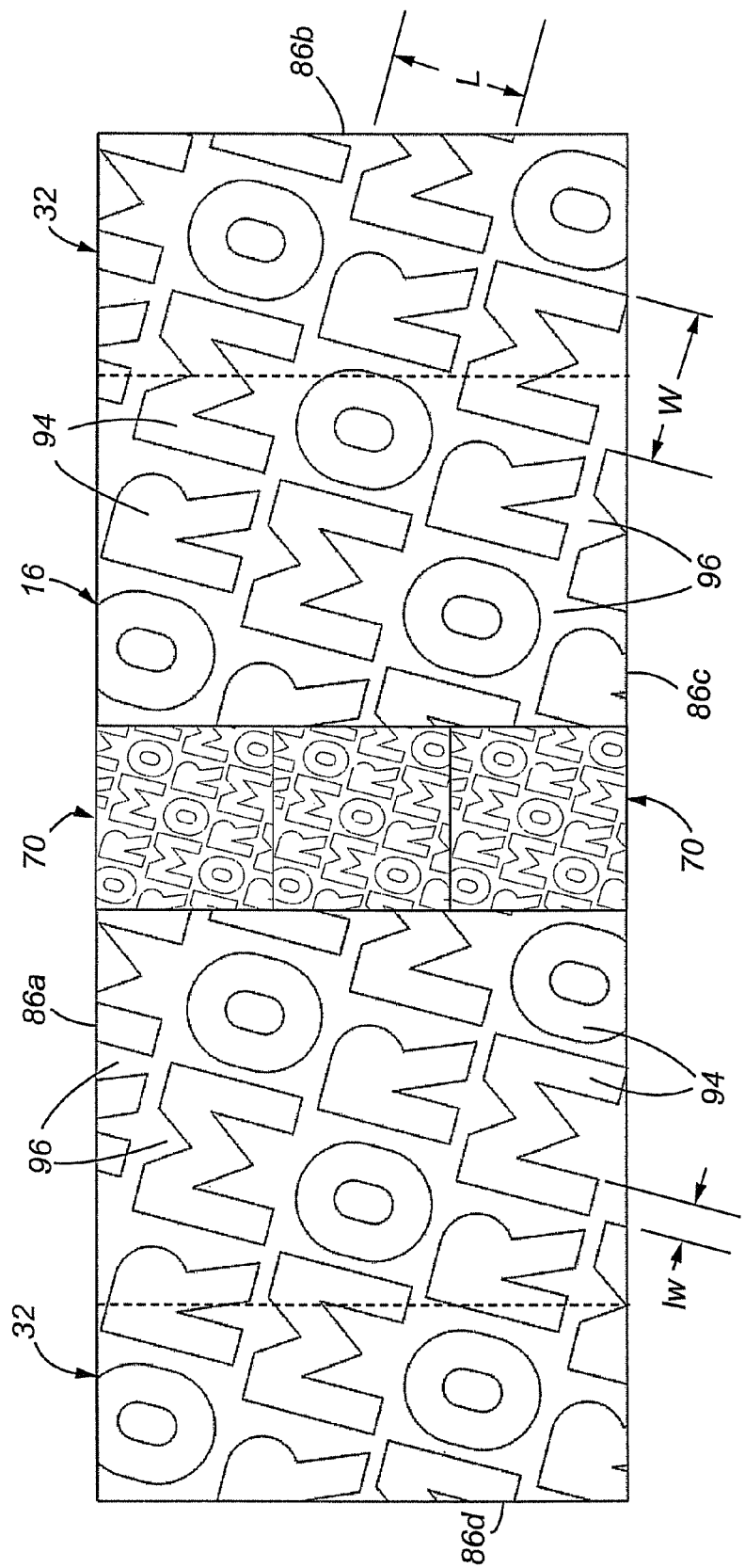
FIG. 11B shows the base of an orthodontic appliance, e.g., the bracket shown in FIGS. 1B and 5B with the flanges, wherein the base includes a character base pattern and an auxiliary slot with a character pattern in the auxiliary slot.
Figure 20:
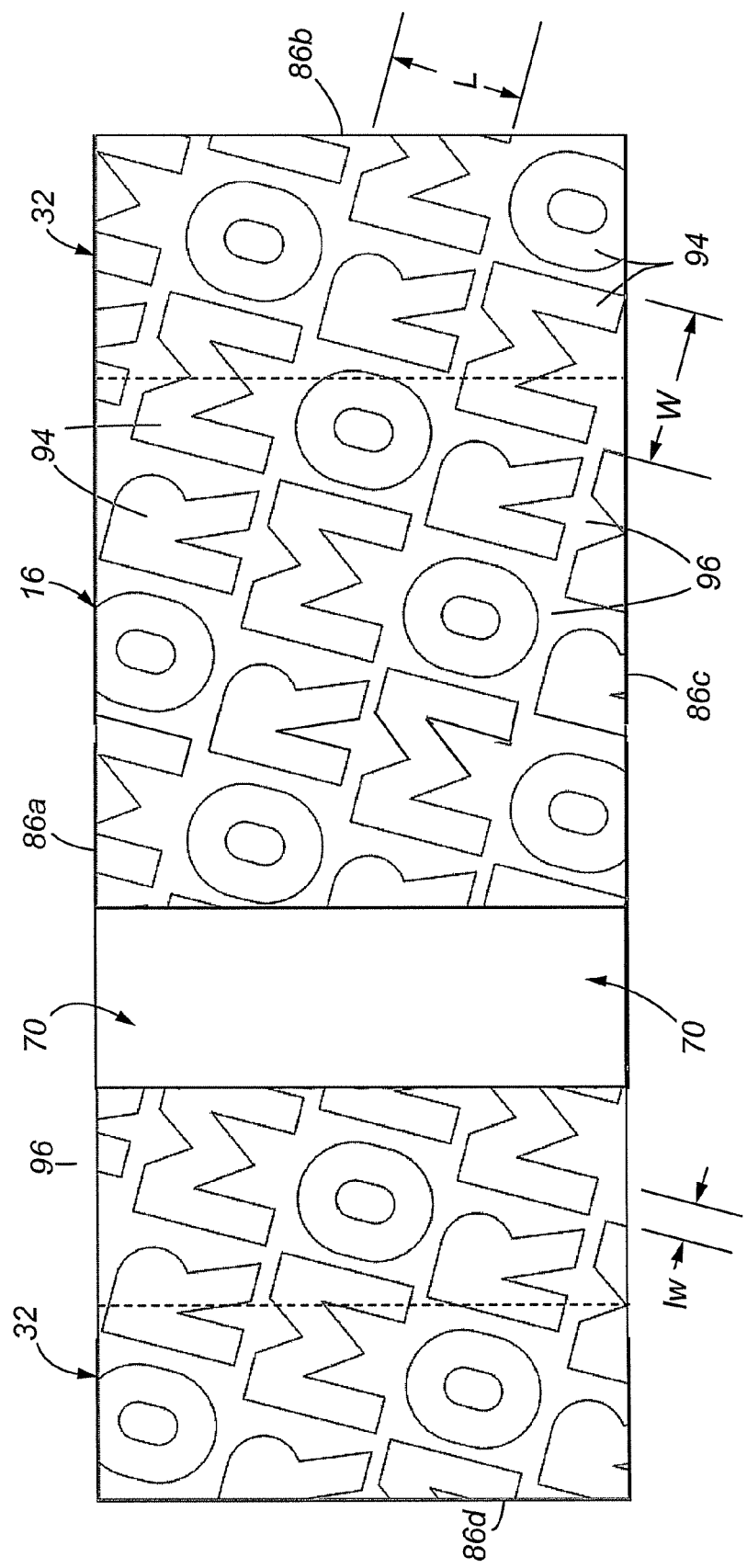
FIG. 20 shows the base of an orthodontic appliance having a character pattern for identifying the supplier of the appliance, wherein there is a single auxiliary slot that is offset from the center of the base 16.

Referring again to FIGS. 1B and 5B, a bracket 10 having a base 16 with a single auxiliary slot 70 is shown. However, such an auxiliary slot 70 need not be centrally located along the mesial-distal extent of the bracket. Instead, the auxiliary slot 70 more to the mesial side of the bracket, or more to the distal side of the bracket. Indeed, FIG. 20 shows such an offset auxiliary slot 70 provided in the base 16 of an orthodontic appliance. A rear plan view of the base of FIGS. 1B and 5B is shown in FIGS. 11A and 11B (although these latter figures may equally well apply to the base 16 of other types of orthodontic appliances, e.g., those having tubes), wherein the rear of the bracket 10 incorporates characters 94. For the bracket (or other orthodontic appliance) shown in FIG. 11A, when flanges 32 are incorporated into the base 16 having characters 94, the characters 94 are preferably extended across the entire rear surface of the bracket 10, with the exception of the area occupied by the auxiliary slot 70. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 (not including the area occupied by the auxiliary slot 70) and the flanges 32, and more preferably, about 55% of the total two dimensional surface area of base 16 (not including the area occupied by the auxiliary slot 70) and the flanges 32. Correspondingly, preferably the projected surface 90 comprises between about 40% to 50% of the total two dimensional surface area of the base 16 (not including the area occupied by the auxiliary slot 70) and the flanges 32, and more preferably, about 45% of the total two dimensional surface area of the base 16 (not including the area occupied by the auxiliary slot 70 and the flanges 32. These preferred values have been found to provide better adhesion characteristics between the bracket and the tooth to which it is applied. Accordingly, a determination may be as to whether the characters 94 are provided on the recessed surface 92, or on the projected surface 90 depending on which of these alternatives most closely yields the above preferred surface percentages for the recessed and projected surfaces.

Referring now to FIG. 11B, the orthodontic appliance base 16 includes a character pattern 94 within the area of the auxiliary slot 70. When characters 94 are integrated into the auxiliary slot 70, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slot 70 may have a rounded (not shown) or alternatively textured exterior surface that advantageously interacts with the tool to be inserted therein.

Figure 12A:
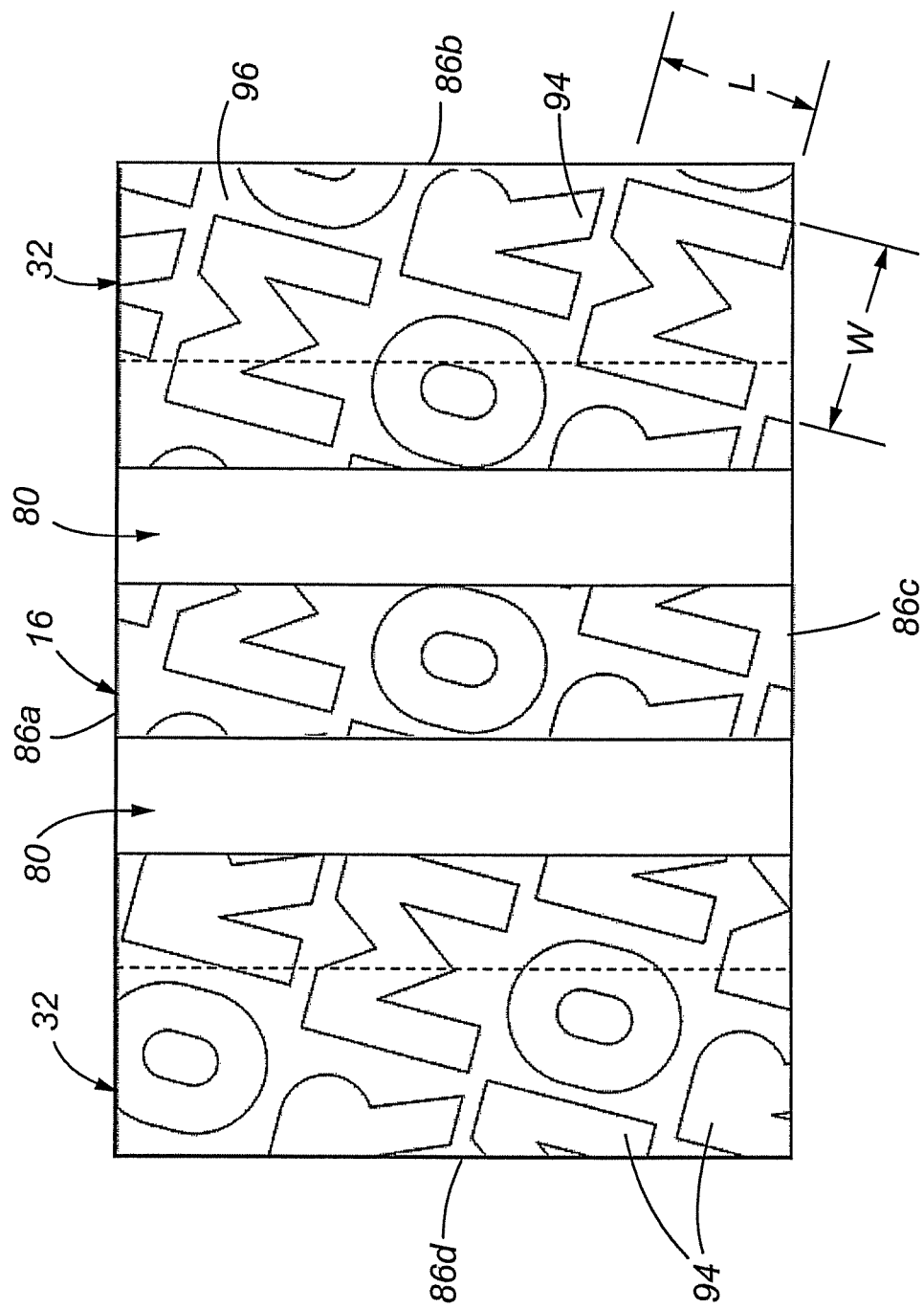
FIG. 12A shows the base of an orthodontic appliance, e.g., the bracket shown in FIG. 6B with flanges, wherein the base includes a character base pattern and twin auxiliary slots without a character pattern in the auxiliary slots.
Figure 12B:
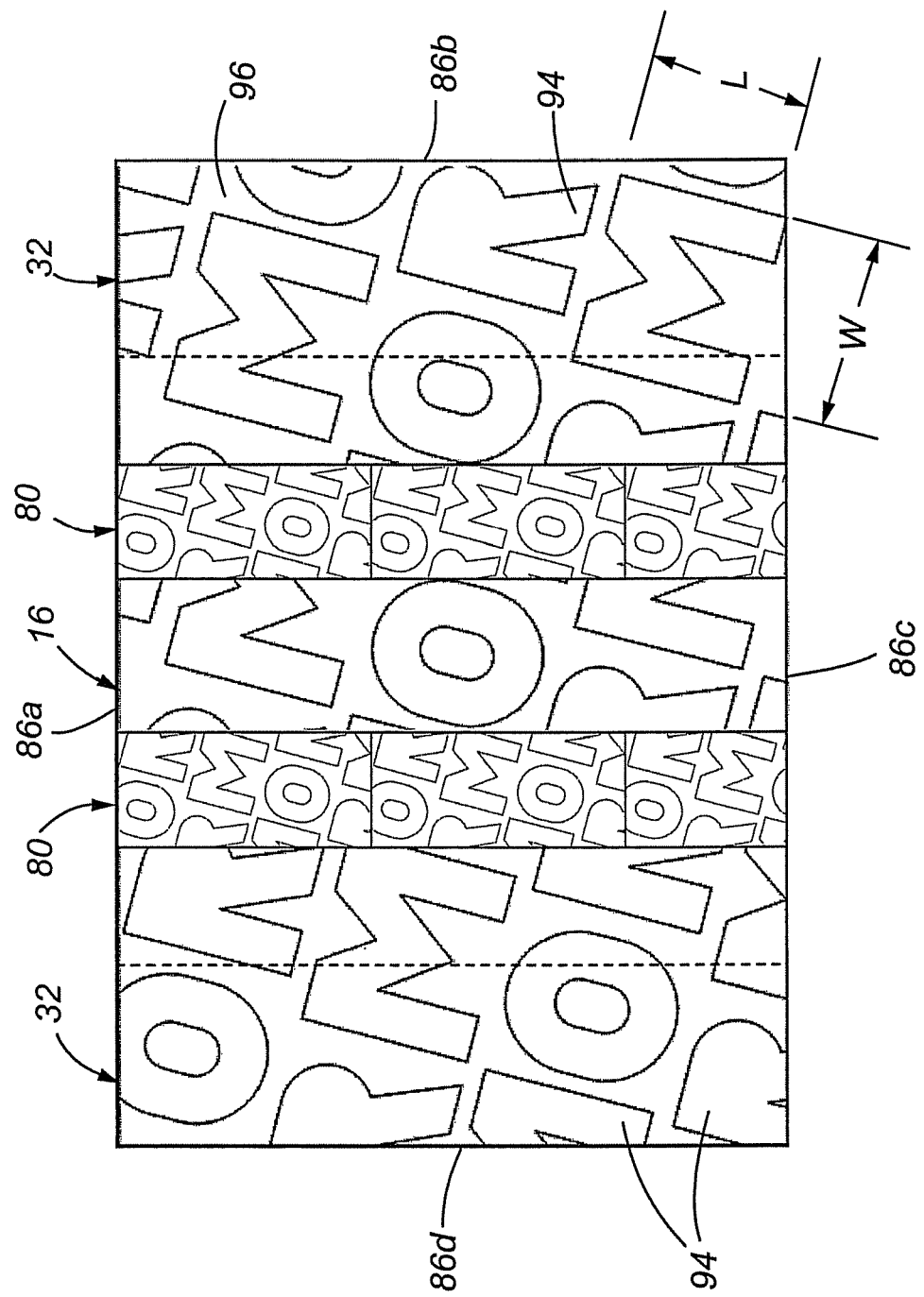
FIG. 12B shows the base of an orthodontic appliance, e.g., the bracket shown in FIG. 6B with flanges, wherein the base includes a character base pattern and twin auxiliary slots with a character pattern in the auxiliary slots.
Figure 13:
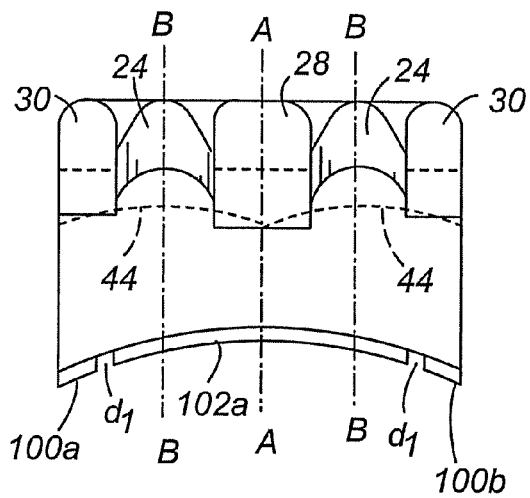
FIG. 13 is a plan view of the bracket of FIG. 4B without flanges, and including a discontinuous perimeter rail.

Referring again to FIG. 3B, a bracket 10 having a base 16 with twin auxiliary slots 80 is shown. A plan view of the rear of FIG. 3B is shown in FIGS. 12A and 12B (although these latter figures may equally well apply to the base 16 of other types of orthodontic appliances, e.g., those having tubes), wherein the rear of the bracket 10 incorporates characters 94. For the base 16 shown in FIG. 12A, when flanges 32 are incorporated into the base 16 having characters 94, the characters 94 are preferably extended across the entire rear surface of the orthodontic appliance, with the exception of the area occupied by the twin auxiliary slots 80. Consistent with the other embodiments described above, preferably the characters 94 form the recessed surface 92 as shown in FIG. 9A, and the intermediate space 96 forms the projected surface 90. Whether the characters 94 are letters, numbers, logos, symbols, or graphics, preferably the recessed surface 92 comprises between about 50% to 60% of the total two dimensional surface area of the base 16 (not including the area occupied by the twin auxiliary slots 80) and the flanges 32, and more preferably, about 55% of the total two dimensional surface area of base 16 (not including the area occupied by the twin auxiliary slots 80) and the flanges 32. Correspondingly, preferably the projected surface 90 comprises between about 40% to 50% of the total two dimensional surface area of the base 16 (not including the area occupied by the twin auxiliary slots 80) and the flanges 32, and more preferably, about 45% of the total two dimensional surface area of the base 16 (not including the area occupied by the twin auxiliary slots 80) and the flanges 32. These preferred values have been found to provide better adhesion characteristics between the bracket (more generally, orthodontic appliance) and the tooth to which the appliance is applied.

Referring now to FIG. 12B, the base 16 shown includes a character pattern 94 within the area of the auxiliary slots 80.

As with the single auxiliary slot 70 shown in FIG. 11B, when characters 94 are integrated into the auxiliary slots 80, the characters 94 may have different dimensions than that of the remaining base 16. Preferably, the character pattern 94 may be finer, thus limiting the probability of a tool to be inserted therein from hanging-up or catching on the characters 94. Alternatively, the character pattern 94 in the auxiliary slots 80 may have a rounded (not shown), or alternatively textured exterior, surface that advantageously interacts with the tool to be inserted therein. Note that such an auxiliary slots 80 need not be symmetrically located along the mesial-distal extent of the bracket. Instead, the auxiliary slots 80 more to the mesial side of the bracket, or more to the distal side of the bracket. The auxiliary slots 80 may be provided in locations along the base 16 according to the auxiliary tool to be fitted therein. Thus, one such auxiliary slot 80 may be near the mesial edge of the base 16, whereas the other auxiliary slot may near the center of mesial-distal extent of the base.

Referring again to FIG. 4B, in yet a separate aspect of the disclosure, the bracket 10 (more generally, an orthodontic appliance) may include a curved base 16. The base 16 may be contoured at a variety of angles depending upon the curvature of the patient's tooth surface.

Referring now to FIGS. 13-15A,B in yet a separate aspect of the disclosure, base 16 of an orthodontic appliance (e.g., bracket 10 or another appliance) preferably includes a perimeter rail, and more preferably, a discontinuous perimeter rail. The discontinuous perimeter rail preferably includes at least one corner segment, and more preferably, a plurality of corner segments, including a distal/gingival corner 100a, a gingival/mesial corner 100b, a mesial/occlusal corner 100c, and an occlusal/distal corner 100d. Corners 100a, 100b, 100c, and 100d are preferably between about 0.008 to 0.011 inches in width "cw", and more preferably, are about 0.085 inches wide. Each corner 100a, 100b, 100c, and 100d is separated from the other corners segments by a distance or a cavity. Preferably, the discontinuous perimeter rail also includes at least one straight segment, and more preferably, a plurality of straight segments. More preferably yet, two straight segments are provided, namely a gingival straight segment 102a and an occlusal straight segment 102c. The gingival straight segment 102a is separated from the distal/gingival corner 100a and the gingival/mesial corner 100b by a cavity or a distance "$d_1$" of about 0.008 to 0.011 inches, and more preferably, by a distance $d_1$ approximately equal to the width cw (FIG. 14) of the discontinuous perimeter rail, or about 0.0085 inches. Similarly, the occlusal straight segment 102c is separated from the mesial/occlusal corner 100c and the occlusal/distal corner 100d by a cavity or distance $d_1$ of about 0.008 to 0.011 inches, and more preferably, by a distance $d_1$ approximately equal to the width cw of the discontinuous perimeter rail, or about 0.0085 inches. Although base 16 of an orthodontic appliance will function without a perimeter rail, the discontinuous perimeter rail in combination with characters 94 increases the bonding strength of orthodontic appliance when it is attached to a tooth using an adhesive.

Referring again to FIG. 14, although it may be present, in a preferred embodiment, the discontinuous perimeter rail does not include a distal straight segment between the distal/gingival corner 100a and the occlusal/distal corner 100d. In addition, in a preferred embodiment, the discontinuous perimeter rail does not include a mesial straight segment between the gingival/mesial corner 100b and the mesial/occlusal corner 100c.

Figure 14:
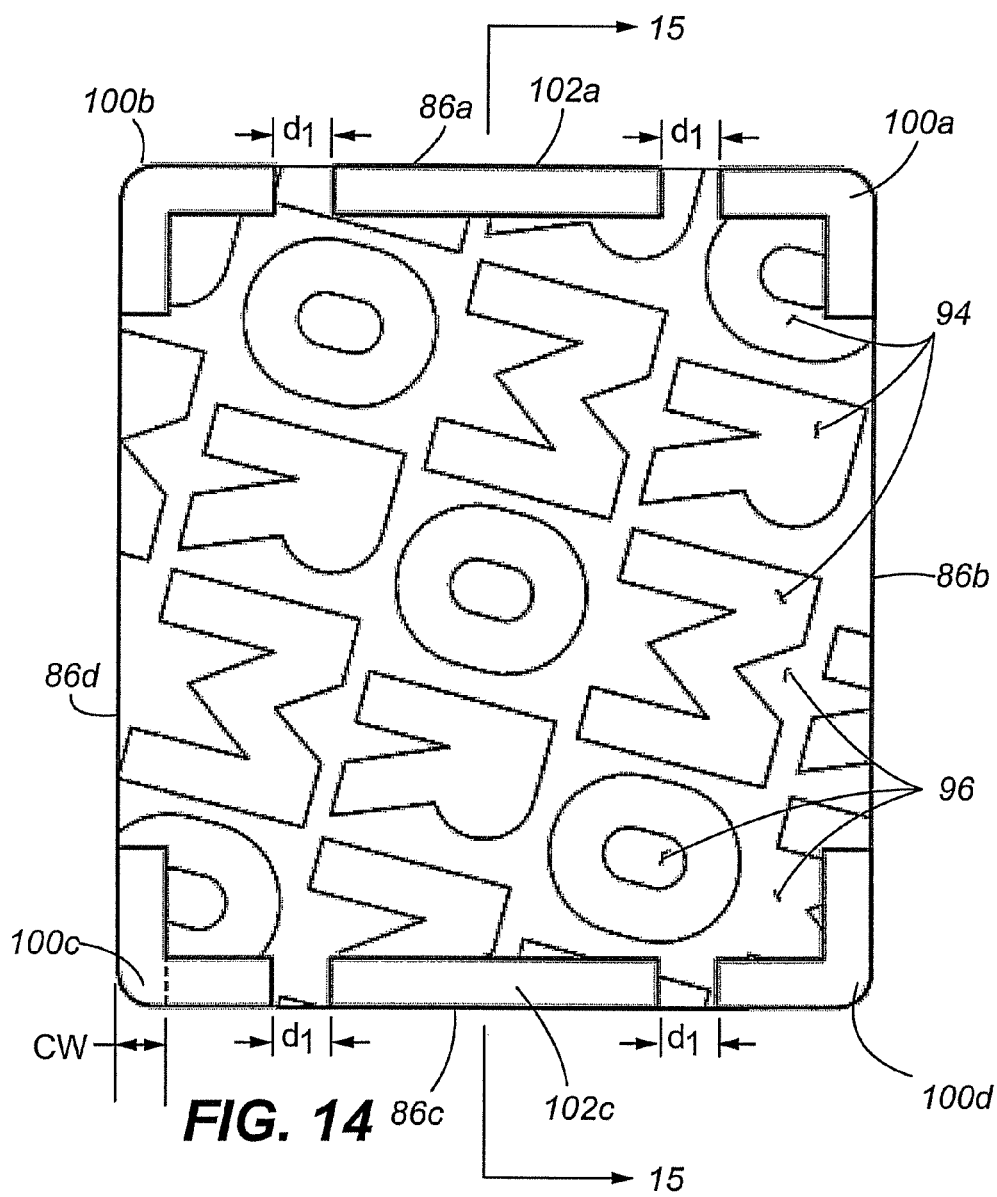
FIG. 14 is a rear or underneath view of the base of the bracket shown in FIG. 13.

Still referring to FIG. 14, in a preferred embodiment, the perimeter rail is preferably positioned within the base 16 area defined by edges 86a, 86b, 86c, and 86d. More specifically, corners 100a, 100b, 100c, and 100d, as well as straight segments 102a and 102c of the discontinuous perimeter rail are all disposed within the interior of the area defined by base edges 86a, 86b, 86c, and 86d. The total two dimensional surface area in rear elevation view, or the exterior surface of the base 16 is defined herein as the area in rear elevation view between edges 86a, 86b, 86c, and 86d for the base surfaces parallel to the tooth's surface. Where a discontinuous perimeter rail is used, the discontinuous perimeter rail portions 100a, 100b, 100c, 100d, 102a and 102c comprise between about 12% to 16% of the total two dimensional surface area of the base 16, and more preferably, about 14% of the total two dimensional surface area of base 16. Whether the characters 94 are letters, numbers, logos, symbols, or graphics, when a discontinuous perimeter rail is present, preferably the recessed surface 92 comprises between about 45% to 50% of the total two dimensional surface area of the base 16, and more preferably, about 48% of the total two dimensional surface area of base 16. Correspondingly, when a discontinuous perimeter rail is present, preferably the projected surface 90 comprises between about 35% to 40% of the total two dimensional surface area of the base 16, and more preferably, about 38% of the total two dimensional surface area of the base 16.

Figure 15A:
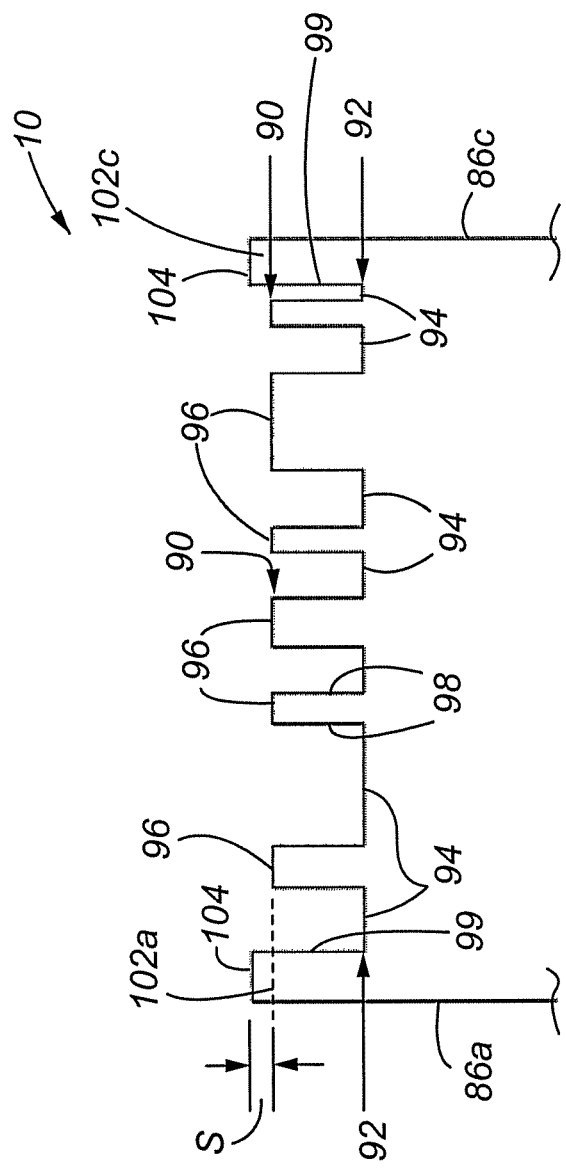
FIGS. 15A-B are cross-sections taken along sectioning plane 15-15 of FIG. 14, this plane represented by the line segments identified with the labels 15.
Figure 15B:
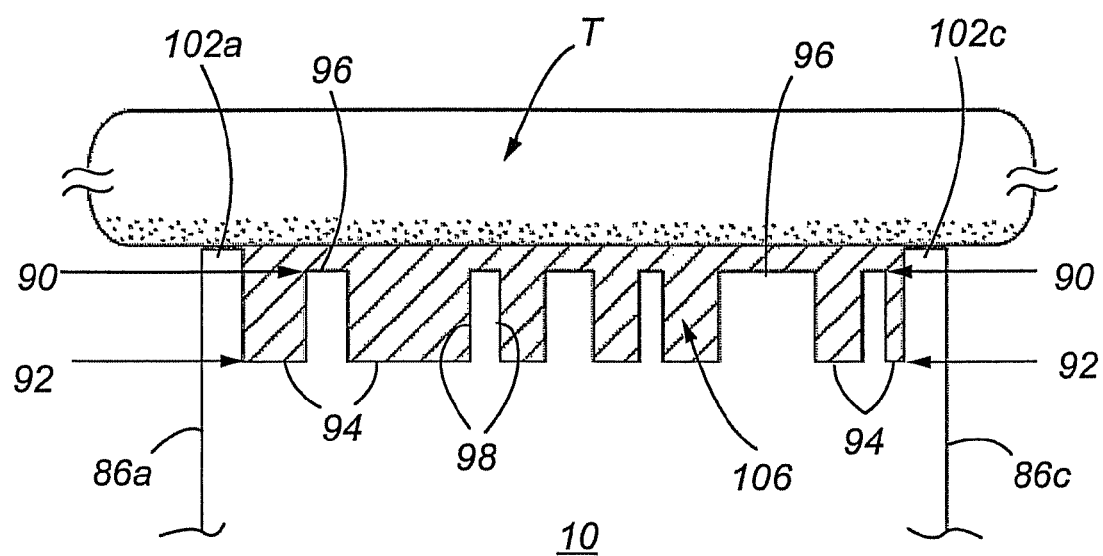

Referring now to FIG. 15A, a cross-sectional view along line 15-15 as shown in FIG. 14 is provided. The cross-sectional view of FIG. 15A shows the gingival straight segment 102a and the occlusal straight segment 102c along the gingival and occlusal edges of the orthodontic appliance whose base 16 is shown in FIG. 14. FIG. 15A also shows that the rail surface 104 is disposed beyond the projected surface 90. In the preferred embodiment depicted in FIG. 15A, the projected surface 90 is comprised of the intermediate space 96 between characters 94, while the recessed surface 92 is comprised of the characters 94. The rail surface 104 preferably projects a distance "s" of about 0.002 to 0.004 inches beyond the projected surface 90, and more preferably, the rail surface 104 projects about 0.003 inches beyond the projected surface 90. Thus, when the orthodontic appliance of FIG. 14 having a discontinuous rail is placed with its base 16 in contact with a patient's tooth, the rail surface 104 contacts the patient's tooth. The discontinuous rail thus forms a pocket for the collection of adhesive. Thus, upon application of the orthodontic appliance of FIG. 14 to a patient's tooth, the openings between the perimeter rail permit excess adhesive to escape under the applied pressure, thereby preventing the appliance from having an adhesive layer that is too thick and moving away from the tooth as a result of increased hydraulic pressure formed within the adhesive pocket when the appliance is first pressed against the tooth to which it is being applied. Thus, the discontinuous structure of the perimeter rail improves the bonding strength between the orthodontic appliance and the patient's tooth because it allows excess adhesive to escape during the application of the appliance to the tooth's surface. Furthermore, as shown in FIG. 15B, the difference in distance provided by the projection of the perimeter rail beyond the projected surface 90 allows a layer of adhesive 106 to bond between the projected surface 90 and the tooth's surface. Thus, a layer of adhesive is formed within the entire interior area 88 of the base that is not otherwise occupied by the discontinuous perimeter rail segments 100a-d, and 102a and 102c. This further improves bonding between the orthodontic appliance and the tooth's surface.

Referring to FIGS. 14 and 15A, as one of skill in the art will understand, the walls 98 (FIG. 15A) together with the rail walls 99 provide substantially more base surface area to which an adhesive can bond. In fact, the embodiment of FIG.

14 results in approximately a base total surface area increase of more than 140%. This can be seen as follows. Since all walls 98 and 99 are at least the height of walls 98, assume for the moment that the height of all walls is the same as walls 98. An approximation to the increase in base total surface area by the walls can be obtained by comparing:

(a) the sum of the line segments of the extent of the walls 98 and 99 (FIG. 15A), plus, the line segments residing on the projected surface 90 and on the recessed surface 92 of both cross section in FIG. 15A with (b) the straight line extent of the base 16 along cross section 15-15 of FIG. 14.

Accordingly, since the wall height is approximately 0.12 of the straight line extent across the base 16 of FIG. 14 at cross section identified by the sectioning plane 15-15, and since there are 12 walls in the cross section shown in FIG. 15A, an approximation to the ratio of: (1) the base surface area immediately surrounding the cross section 15-15 to (2) a non-embedded (e.g., two dimensional) base surface area surrounding the cross section 15-15 to the same extent is approximately (0.12×12) to 1.0 which is 1.44:1.0. Moreover, this ratio holds up over a fine sampling of cross sections of FIG. 14. In particular, for a substantially regularly spaced sampling of 25 cross sections parallel to the cross section of 15-15 of FIG. 14, this same ratio of 1.44:1.0 is obtained. Accordingly, since there may be relatively little curvature in the gingival-occlusal direction of the orthodontic appliance, it is believed that FIG. 14 shows a base 16 with an increase of total surface area of approximately 44% over a corresponding base surface area that does not have characters formed therein; i.e., 144% of the corresponding base surface area that does not have characters formed therein, or equivalently, at least 29% of the total surface area of the base 16 is derived from the surface area of the walls 98 and 99. Moreover, it is believed this approximate increase is somewhat conservative since the extra height of the perimeter rail walls over the projected areas of the base are not included in the above approximation. Furthermore, the increase in total surface area of the base 16 may be made greater by decreasing the width of the font used, and increasing the number of characters (e.g., by providing a greater number of occurrences of the separation character.

Figure 16:
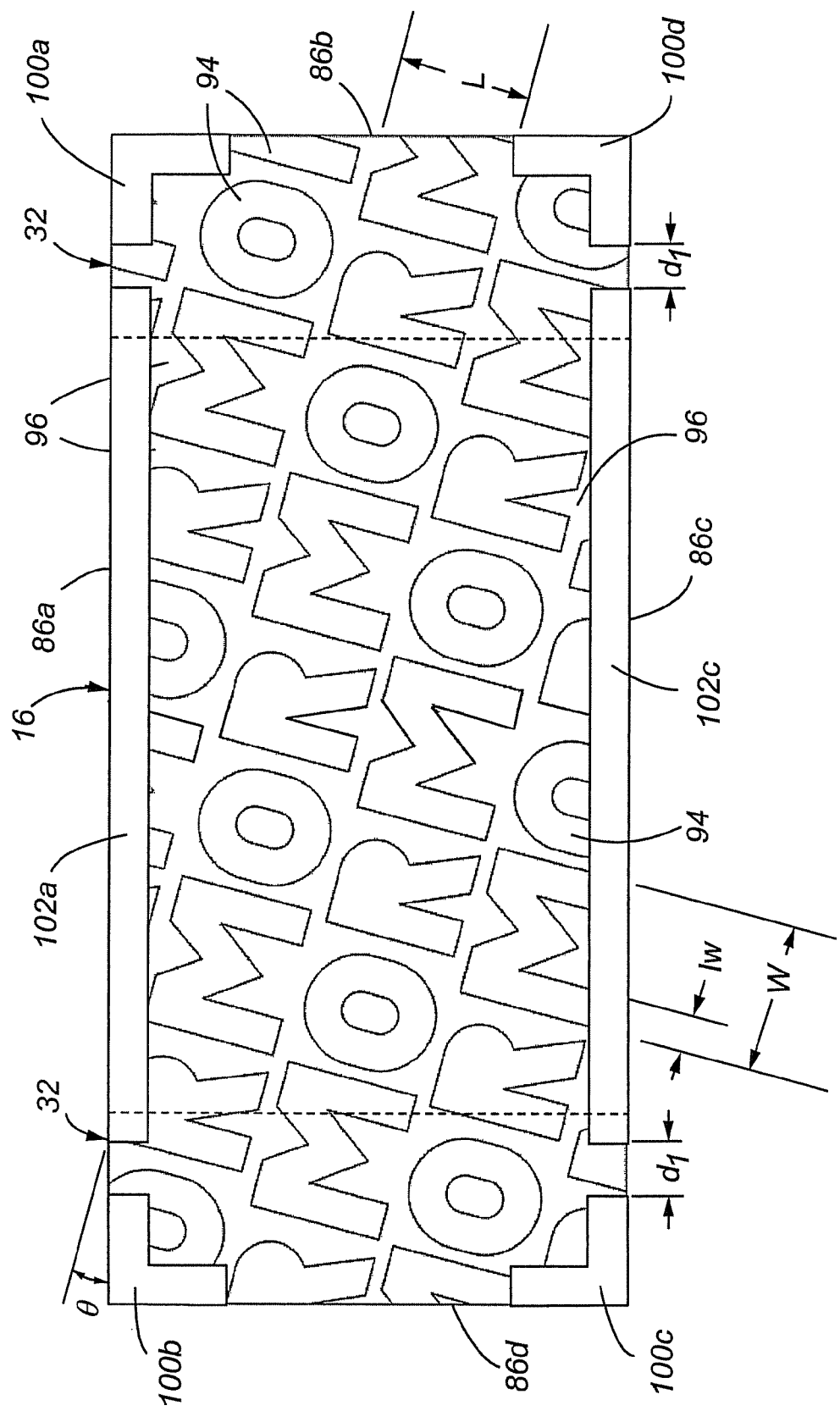
FIG. 16 is a rear view of the base of an orthodontic appliance, e.g., the bracket shown in FIG. 4B with flanges, and including a character base pattern and a discontinuous perimeter rail.

Referring now to FIG. 16, for those orthodontic appliances that include flanges 32 adjacent the base 16, the perimeter rail is preferably located along the outermost edges of the flanges 32. Thus, the discontinuous perimeter rail portions 100a, 100b, 100c, and 100d will occupy the corners formed at the outer limits of the flanges 32. In addition, the gingival straight segment 102a and the occlusal straight segment 102c will occupy portions of the gingival edge 86a and the occlusal edge 86c, respectively. The gingival straight segment 102a and the occlusal straight segment 102c can occupy area along both the base 16 and the flanges 32, depending upon the chosen perimeter rail configuration. In addition, for those orthodontic appliances that include a single auxiliary slot 70 or twin auxiliary slots 80, the perimeter rail is preferably not present along the alignment of the auxiliary slot 70 or slots 80.

In yet a separate aspect of the disclosure, a method of making an orthodontic appliance (e.g., the bracket 10) and its base 16 is disclosed wherein the method is specifically suited for providing a base 16, and optionally flanges 32, having a pattern of characters 94 formed or embedded within the base. In a preferred embodiment, a one-piece molded metal injected orthodontic appliance (e.g. bracket 10) is manufactured from a mold 108. As known to those skilled in the art, the mold 108 (FIG. 17) is produced by electrical discharge machining using shaped electrodes to form the mold 108 itself. More specifically, the shaped electrodes are formed to correspond to the desired shape of at least a portion of one of the exterior surfaces of the orthodontic appliance, such as the exterior surface that forms base 16. The shaped electrodes are then charged and placed in contact with a metal body that will form a portion of mold 108 for production of the actual orthodontic appliances. More specifically, the charged electrode "burns" the desired orthodontic appliance shape into the metal body, thus forming a portion of mold 108. The mold 108 is typically formed from a top and a bottom portion that is then assembled to form a hollow space that defines the contours of the orthodontic appliances to be formed in the mold. The mold 108 is then used to manufacture the orthodontic appliances by injecting the mold 108 with the suitable orthodontic material, such as molten stainless steel, via an injection channel that passes through mold 108 to the interior hollow region defining the appliance form. The molten stainless steel is allowed to cool and harden, and then the mold 108 is separated and the molded orthodontic appliance is subsequently ejected from the mold 108.

In order to adequately bond an orthodontic appliance (having a plurality of characters 94 formed in its base 16) to a tooth surface using an adhesive, the surfaces of the base 16 that are parallel to the tooth's surface are preferably relatively rough. However, if the surfaces of mold 108 corresponding to the base 16 of the orthodontic appliance are too rough, the appliance cannot be ejected from the mold 108 during the appliance's manufacturing process. Thus, in this separate aspect of the disclosure, the mold 108 is preferably manufactured and processed to have appropriate surficial roughness textures along its corresponding base surfaces so that the molded appliances easily release from the mold 108.

Figure 17:
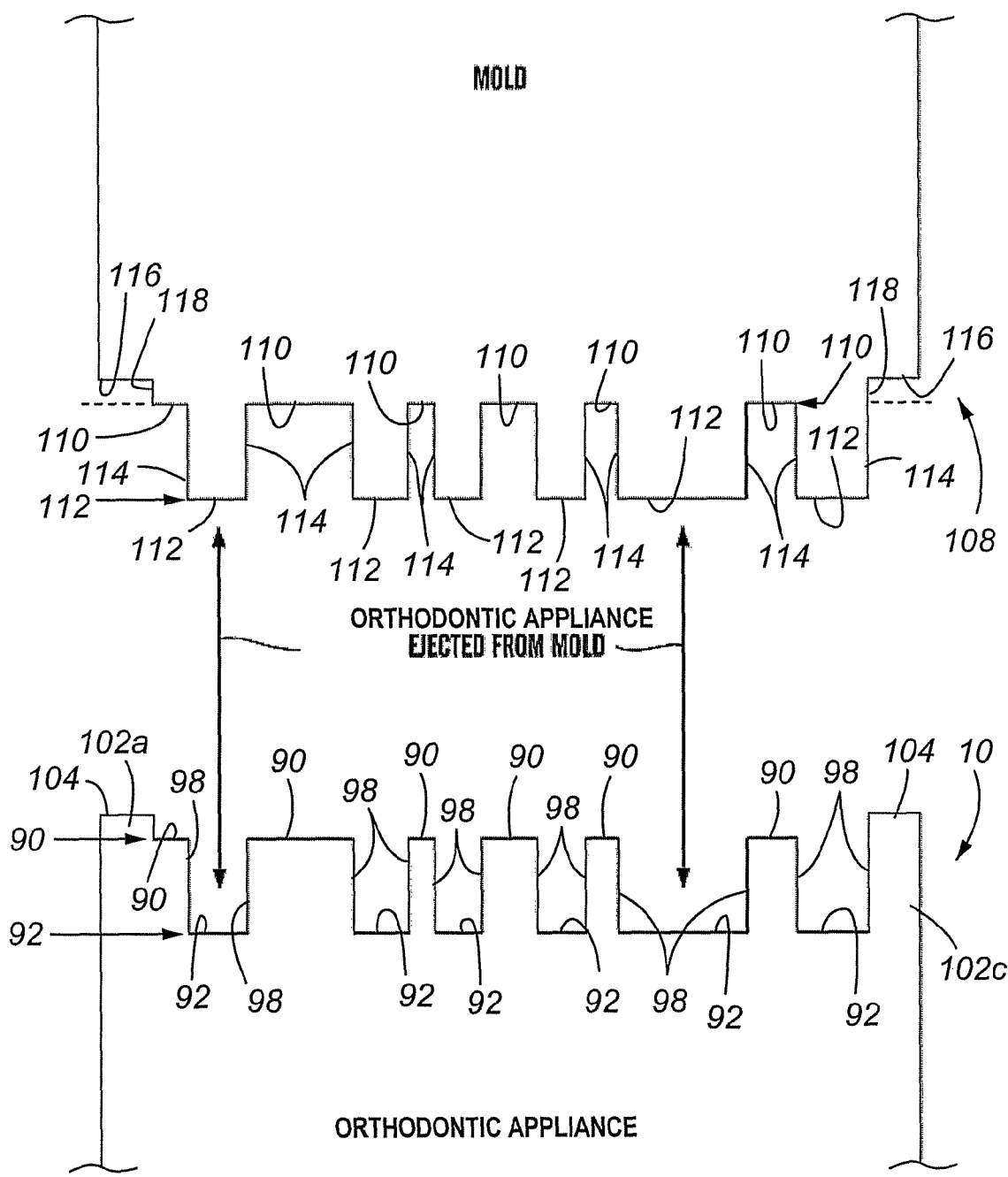
FIG. 17 is a cross-sectional view of the base of an orthodontic appliance having embedded informational characters therein, and a mold used to form the orthodontic appliance.

Referring now to FIG. 17, a mold 108 is shown having a base that includes mold recessed surface 110 and mold projected surface 112, which respectively correspond to the projected surface 90 and the recessed surface 92 of an orthodontic appliance to be manufactured. Preferably, mold recessed surface 110 and mold projected surface 112 have a surface finish of approximately a maximum of 110.8 micro-inches. In contrast, preferably the mold character walls 114 of mold 108 that form the generally sloped or perpendicular surfaces between characters 94 and intermediate spaces 96 of bracket 10 are polished. More specifically, the mold character walls 114 of mold 108 are preferably hand polished to a relatively smooth and polished finish, preferably using a ruby stone, although other means may be employed. Upon manufacture of an orthodontic appliance from mold 108, the hand polished character walls 114 of the mold 108 allow the appliance to be ejected from the mold 108 because the character walls 98 of the appliance are formed to have a smooth and polished finish that corresponds to the polished mold character walls 114 from which they were formed. Thus, a newly formed orthodontic appliance (e.g., the bracket 10) may be ejected from its mold 108 without sticking to the mold 108 and thereby preventing ejection from occurring, or bending or otherwise causing detrimental structural damage to the newly formed appliance during the ejection process. An ejector pin (not shown) may be used to aid the ejection process, wherein the ejection pin forcibly separates the newly formed orthodontic appliance from the mold 108 by pushing base 16 away from mold 108.

Where a perimeter rail is used, the mold 108 preferably includes a deeper recessed surface 116 corresponding to the perimeter rail surface 104. The deeper recessed surface 116 is surficially textured to provide texturing to the perimeter rail surface, which in turn improves bonding between the molded orthodontic appliance and the surface of the tooth. More particularly, the deeper recessed surface 116 of the mold 108 preferably has a surface finish of approximately a maximum of 110.8 micro-inches. In contrast, preferably the mold perimeter rail walls 118 of mold 108 are polished to a smooth finish to prevent a molded orthodontic appliance from sticking to the mold 108 during the ejection process, thereby preventing ejection or otherwise causing detrimental structural damage to the newly formed appliance during the ejection process.

Figure 18:
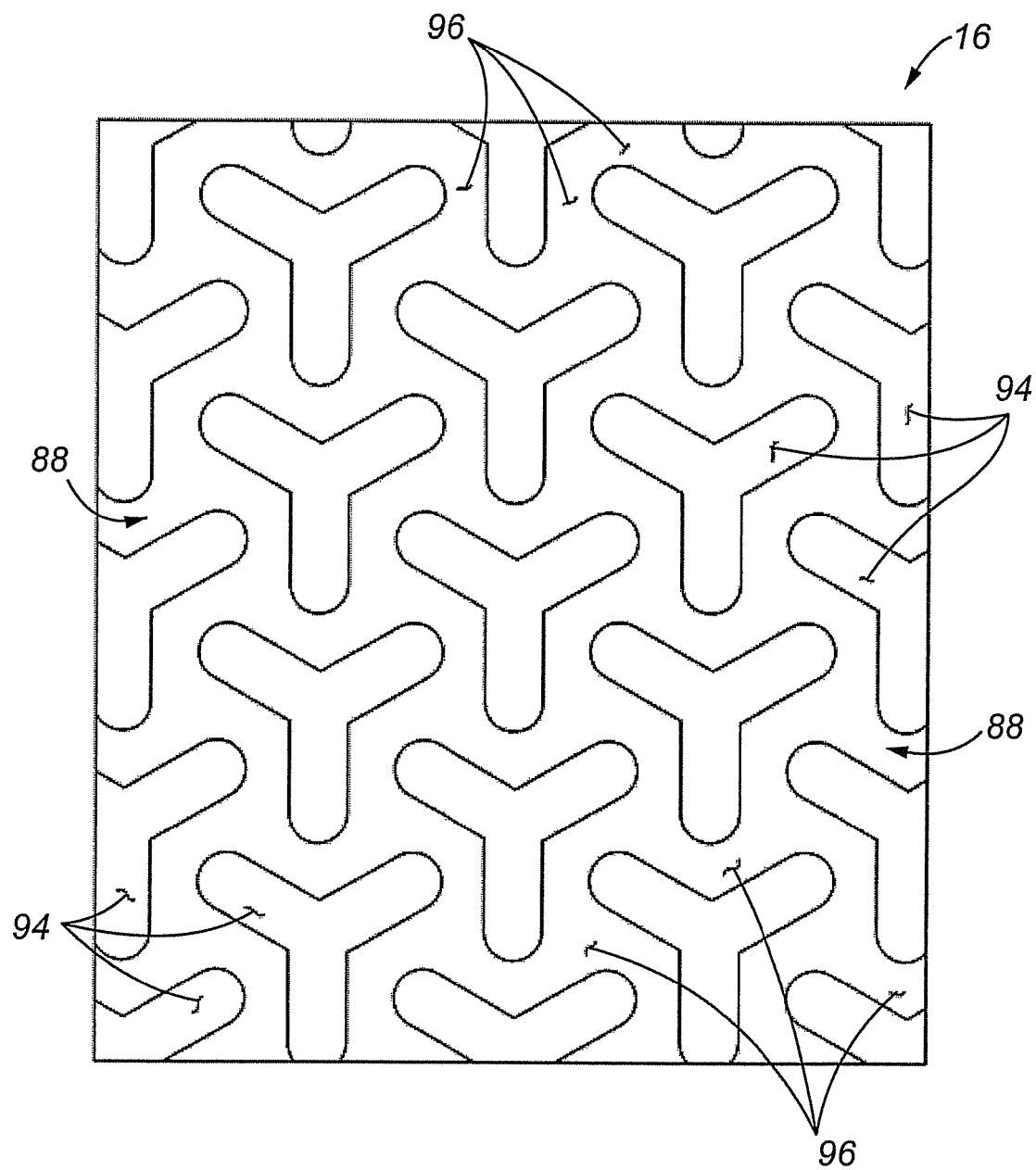
FIG. 18 is a separate embodiment of a pattern embedded into the base 16 of an orthodontic appliance.

Referring now to FIG. 18, an alternate aspect of the disclosure is shown. FIG. 18 presents a pattern of characters 94, wherein the characters are a three-pronged shape resembling the letter "Y". As in the previously described embodiments, intermediate space 96 surrounds the characters 94 within the interior region 88 of the base 16. Accordingly, the present disclosure contemplates the use of patterns of characters 94 wherein the character is a seemingly arbitrary shape, and one in which the base 16 possesses a projected surface 90 and a recessed surface 92. Brackets 10 that included patterns of characters 94 of shapes may further include discontinuous perimeter rail structures as described above.

Figure 19:
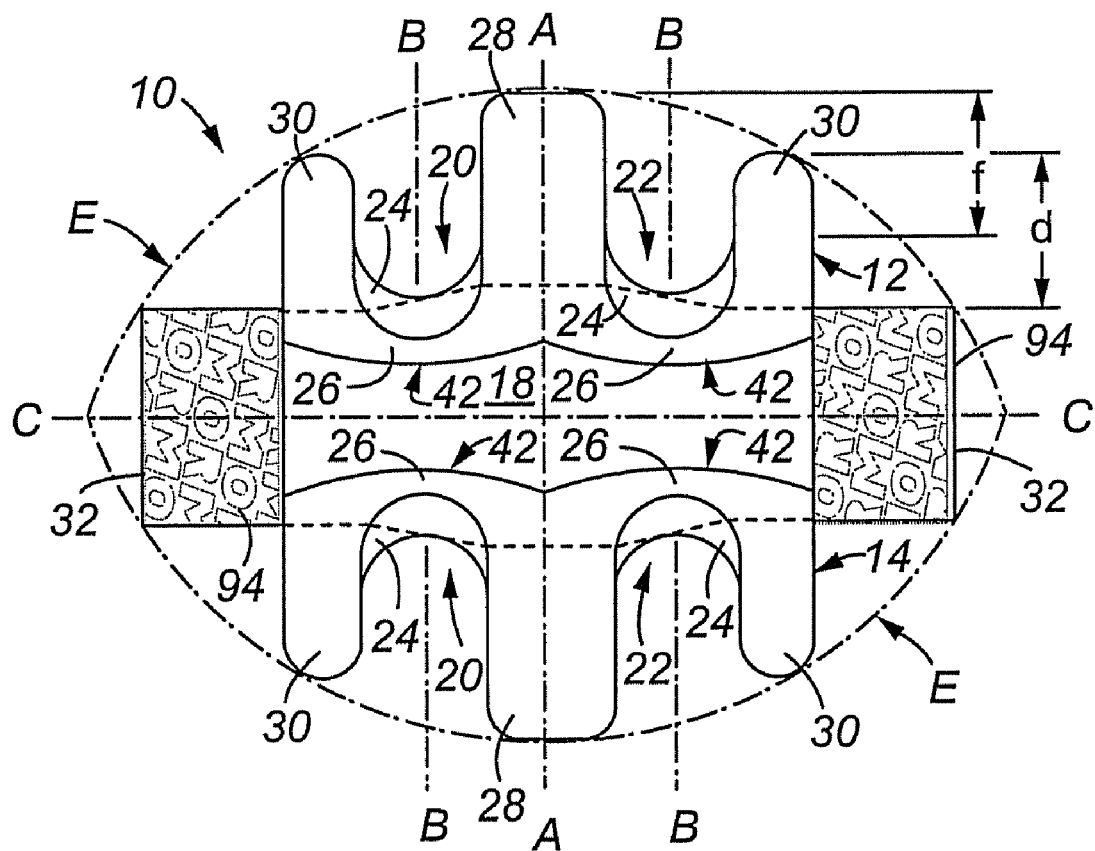
FIG. 19 is a labial view of a bracket having a labial positioned character pattern on its flange portions.

Referring now to FIG. 19, in a separate aspect of the disclosure, a pattern of characters 94 can be integrated into a side or labial position on an orthodontic appliance (e.g., the bracket 10 in FIG. 19). For example, as shown in FIG. 19, the flanges 32 can include a pattern of characters 94 such that the characters 94 are visible from a front view of the bracket 10 (more generally, orthodontic appliance). The pattern 94 could be a trademark of a manufacturer, a message, and/or the pattern 94 may be an ornamental or fanciful design.

In summary, the present disclosure is at least in part directed to a device and method for providing a pattern of characters on the base 16 of an orthodontic bracket. Such characters are preferably formed by creating a recessed pattern of the characters in the base, with the area between the characters raised, such that the area between the characters is closer to the tooth surface when the orthodontic appliance is applied to the surface of a patient's tooth using an adhesive. Alternatively, the characters may be raised and projecting relative to the area between the characters, such that the characters are closer to the tooth surface when the orthodontic appliance is attached to the surface of a patient's tooth.

In a separate aspect of the disclosure, a discontinuous perimeter rail may be used around the character pattern of the base 16. Preferably, the discontinuous perimeter rail includes four separate corner sections and two additional separate straight sections along the gingival and occlusal edges of the base 16. When used, the discontinuous perimeter rail projects beyond the patterned surface of the base, such that the discontinuous perimeter rail is closest to the tooth surface when the orthodontic appliance is attached to a patient's tooth. The discontinuous perimeter rail increases the bonding strength of the orthodontic appliance to the tooth's surface.

The pattern of characters and intermediate space formed on the base 16 of an orthodontic appliance provides a texturing pattern (e.g., an ordered array of projecting features) for bonding the orthodontic appliance to a patient's tooth using an adhesive, while at the same time providing a means of presenting information about the orthodontic appliance on its base surface by advantageously utilizing characters that represent pertinent information, such as the name of the appliance manufacturer, the intended location for the appliance placement, and/or a graphics symbol or logo.

In addition to providing information content on the orthodontic appliance base 16, the embedding of such information substantially increases the base total surface area to which the adhesive can adhere, thus resulting in a more effective bond between a patient's tooth and the orthodontic appliance. However, in some embodiments depending (e.g., on the viscosity of the adhesive), for the adhesive to effectively enter the recesses of the recessed surface 92, such recesses should have at least a minimal extent in two orthogonal directions. As described above, when the recessed portions are characters 94, a line width "lw" for such characters preferably ranges between about 0.008 to 0.010 inches, where line width lw (FIG. 16) is the width of the line forming each individual character 94. This constraint can be extended, wherein if a circle of diameter in the range of at least 0.008 inches were to be provided in all recessed portions and moved about therein the maximal extent possible, then the recessed area covered by the circle should be about at least 85% of the total recessed surface area. That is, only about 15% or less of the recessed surface area should be so confined by one or more walls 98 that this area could not be covered by the circle moving over the maximal extent of the recessed area possible. Note, this more general constraint is clearly shown at least in FIG. 16.

FIGS. 22 through 27 show various orthodontic appliances with bases 16 having encoded information embedded or formed in the bases, wherein the characters 94 are on the projected surface(s) 90 (e.g., as shown in FIGS. 9A and 9B), and the intermediary space 96 between the characters is provided on the recessed surface(s) 92 (e.g., as shown in FIGS. 9A and 9B). Note that the orthodontic appliances shown in these figures include both archwire slots, tubes, and hybrid combinations thereof. The tubes are identified by the label 204.

Figure 40A:
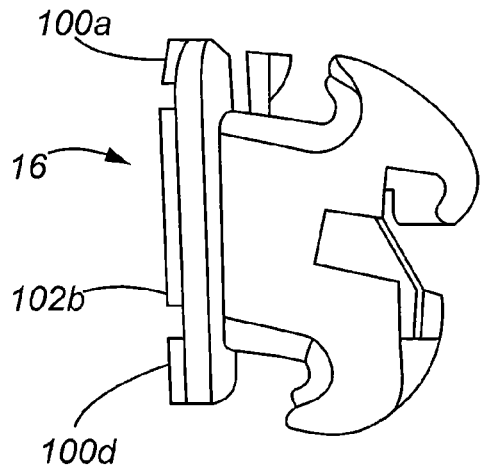
FIGS. 40A and 40B are different views of the same orthodontic appliance.
Figure 40B:
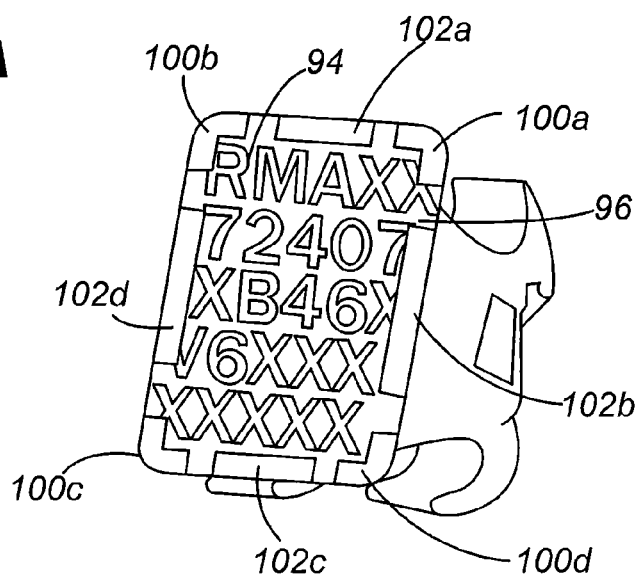
Figure 41:
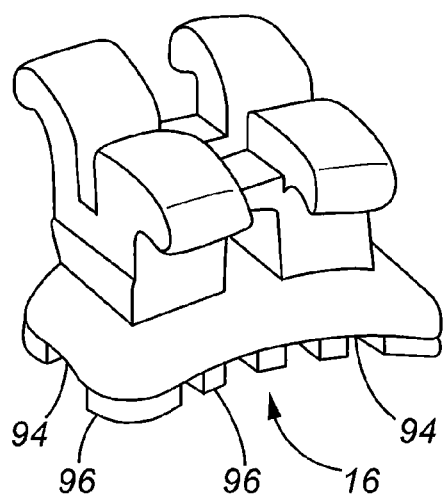
Figure 42:
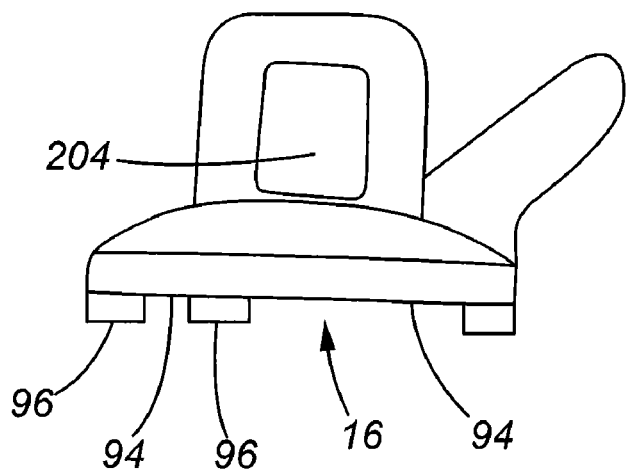
Figure 43:
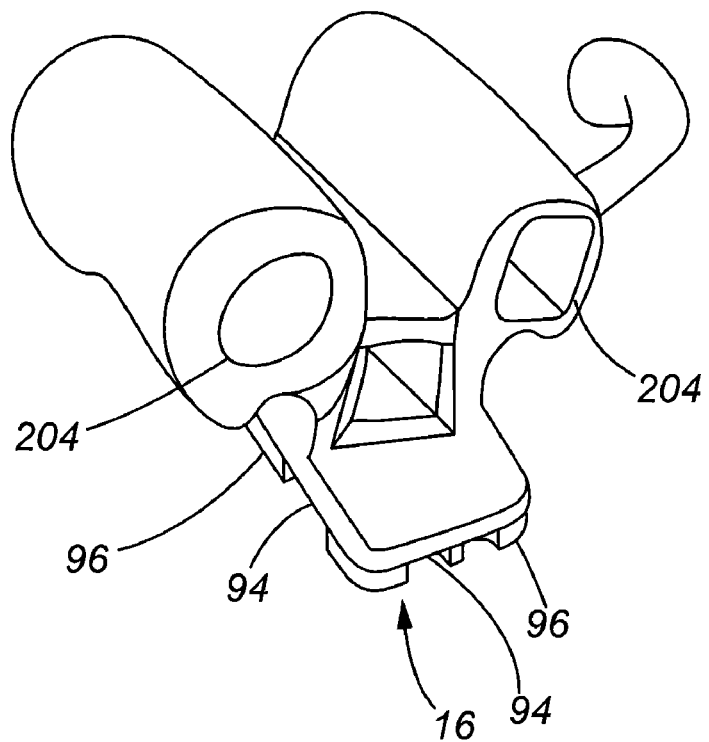
Figure 44:
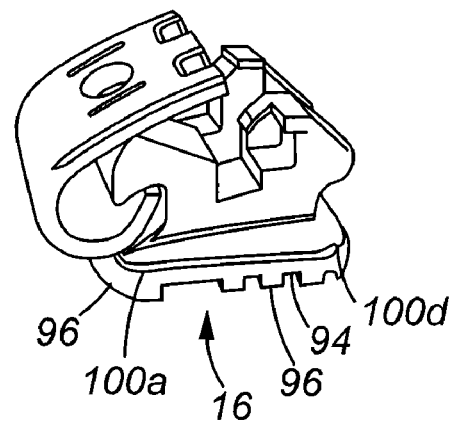
Figure 45:
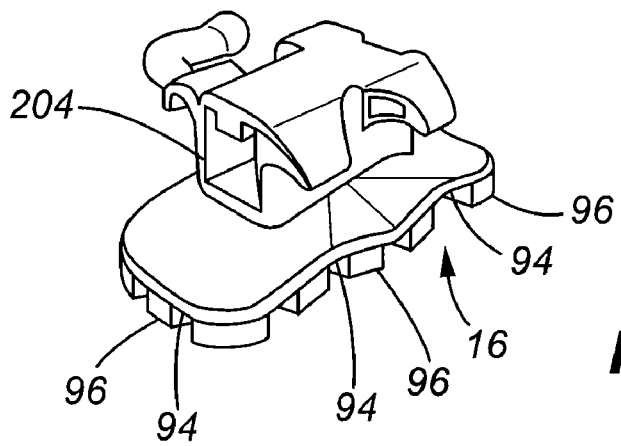
Figure 46:
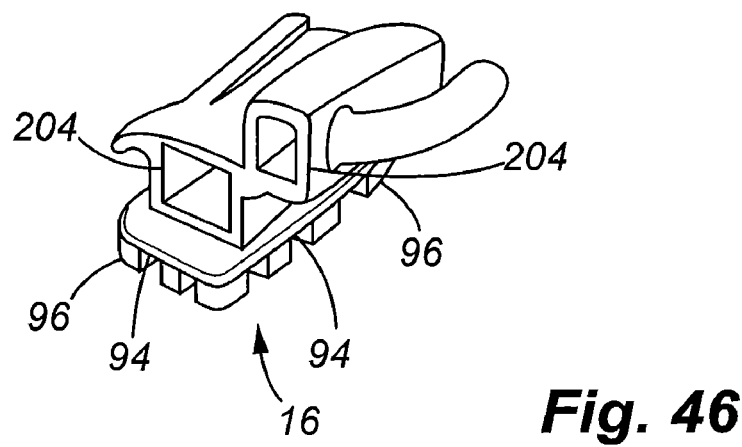
Figure 47:
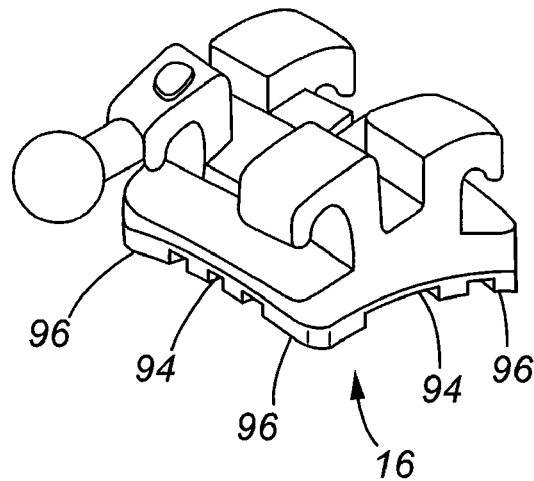
Figure 48:
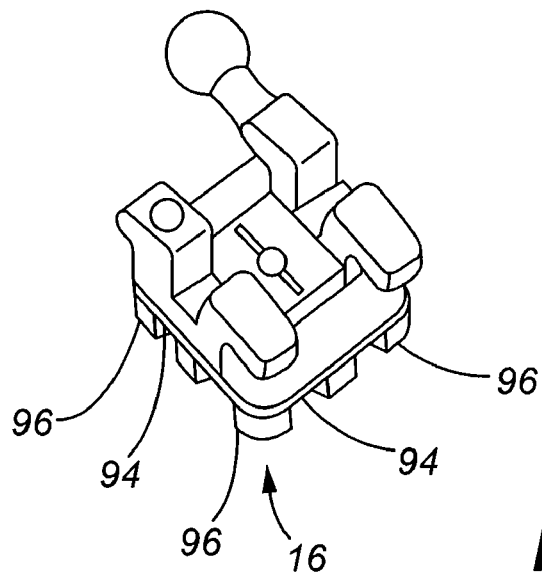
Figure 49:
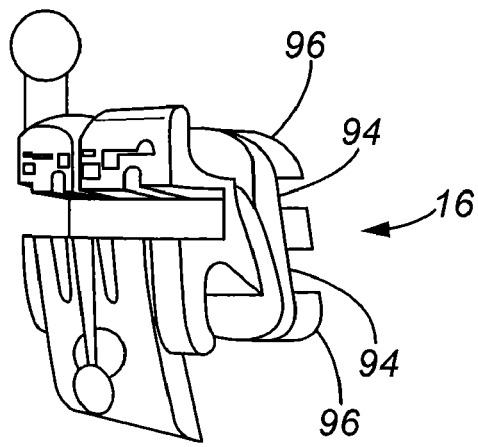
Figure 54:
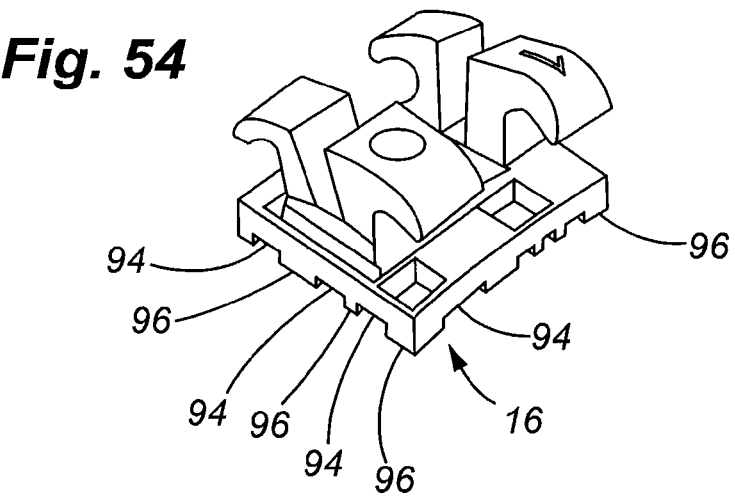
Figure 55:
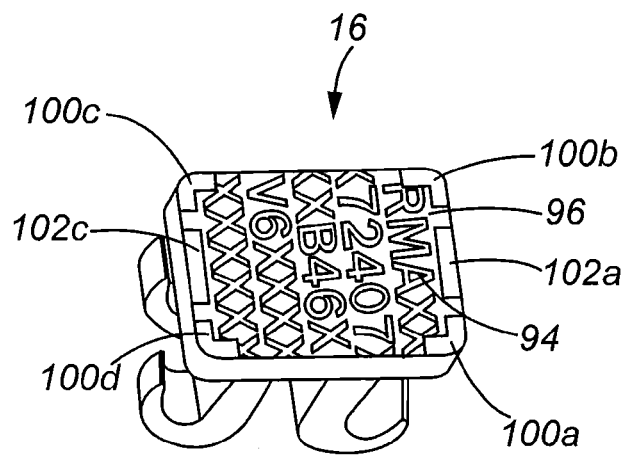
Figure 56:
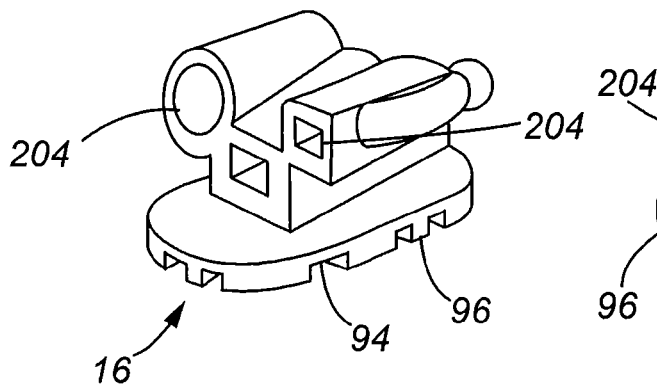
Figure 57:
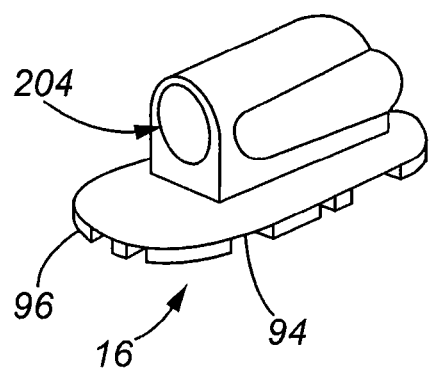
Figure 58:
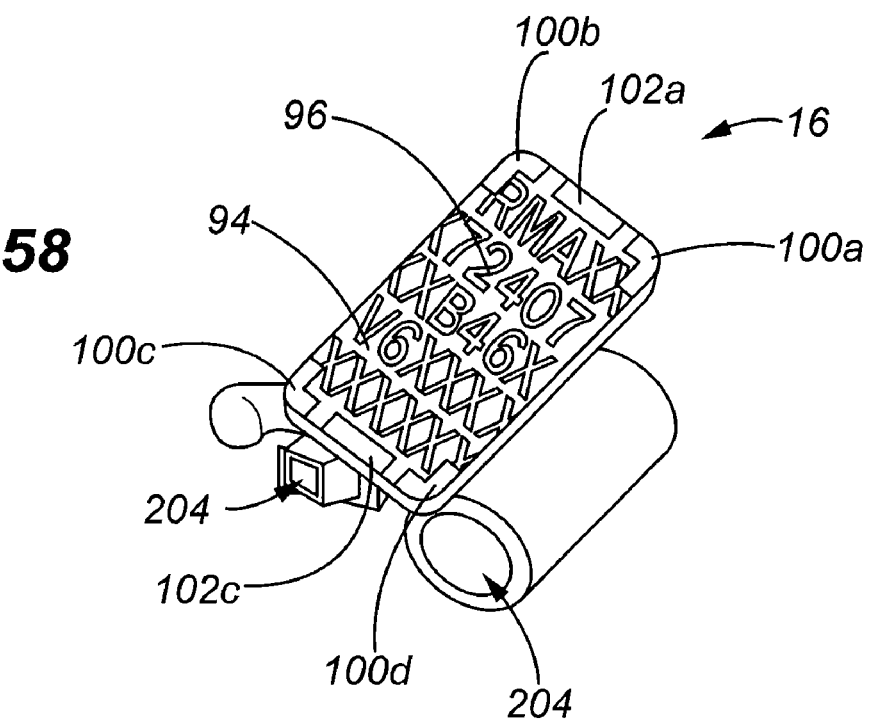
Figure 59:
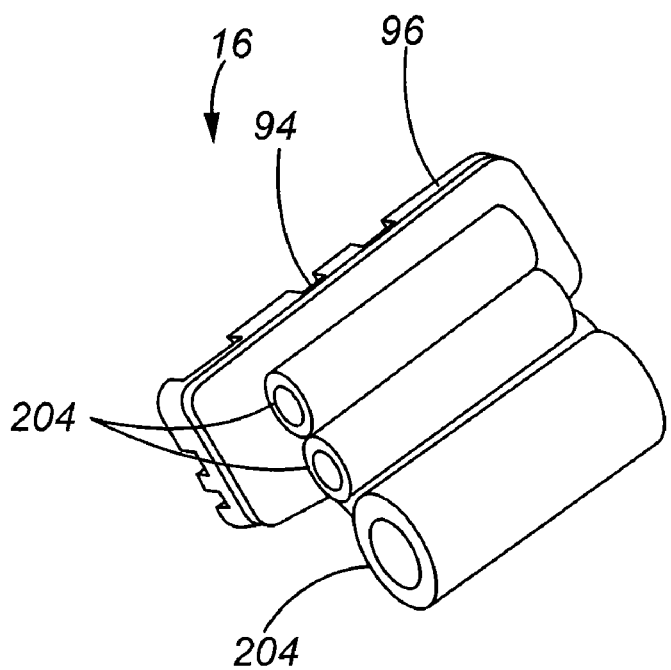
Figure 60:
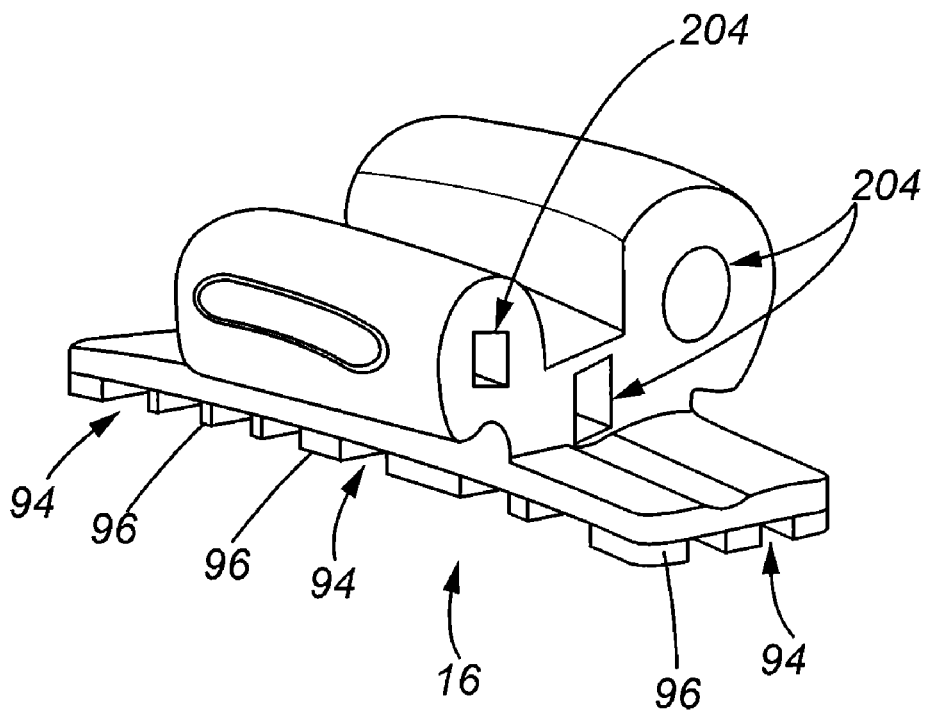
Figure 61:
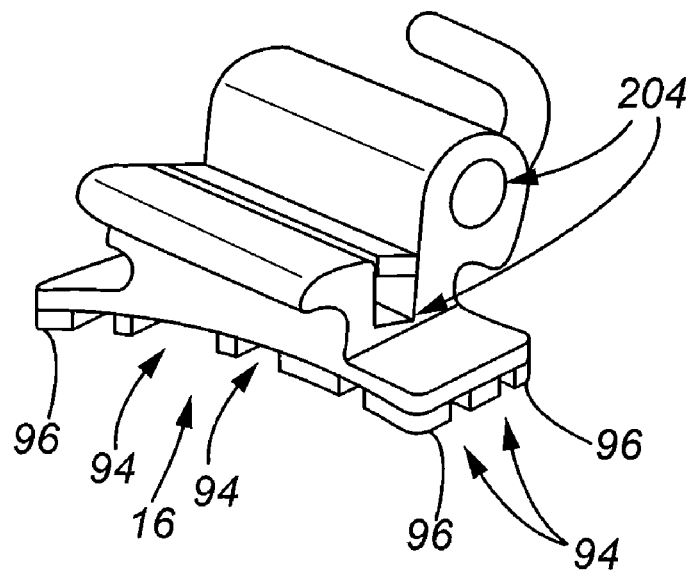
Figure 62:
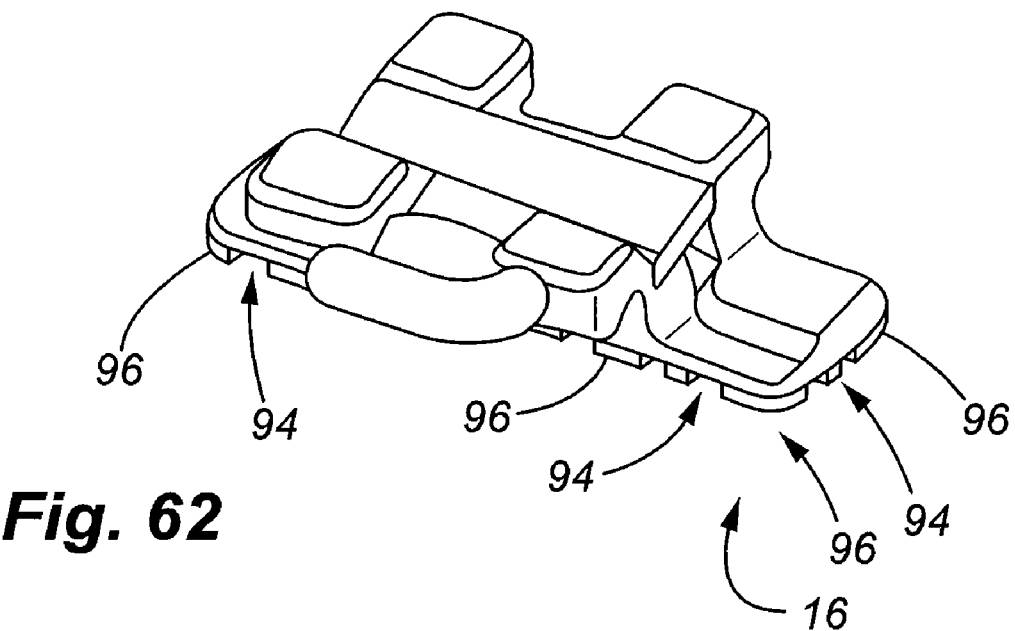
Figure 63:
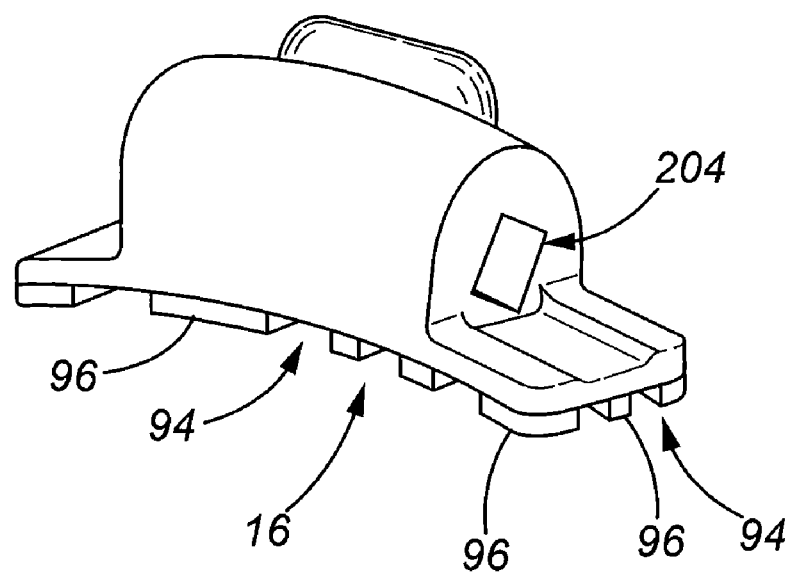

FIGS. 28 through 63 show various orthodontic appliances with bases 16 having encoded information embedded or formed therein, wherein the characters 94 are on the recessed surface(s) 90 (e.g., as shown in FIGS. 9A and 9B), and the intermediary space 96 between the characters is provided on the projected surface(s) 92 (e.g., as shown in FIGS. 9A and 9B). Note that for a given figure number, whenever there are figures A and B for the figure number, such figures A and B are different views of the same orthodontic appliance; e.g., FIGS. 40A and 40B are different views of the same orthodontic appliance. As with the FIGS. 22 through 27, that the orthodontic appliances shown in FIGS. 28 through 59 include both archwire slots, tubes, and hybrid combinations thereof, wherein the tubes are identified by the label 204. Moreover, it is worth mentioning that FIGS. 40A and 40B show an orthodontic appliance (a bracket), wherein the discontinuous perimeter rails of the base 16 further include rails 102b and 102d, respectively on the mesial and distal sides of the orthodontic appliance shown. Although, in general, such an embodiment may not be preferred, such a configuration for the perimeter rails is within the scope of the present disclosure.

The disclosure herein has been describes preferred embodiments of the invention claimed hereinbelow; however, other changes and modifications to the claimed invention may be made which are still contemplated within the spirit and scope of the present disclosure.

The foregoing disclosure has been provided for purposes of illustration and description. This disclosure is not intended to limit the invention claimed hereinbelow, and various embodiments thereof. Variations, embodiments and modifications will be apparent to those skilled in the art and are intended to be within the scope of the following claims.

What is claimed is:

1. An orthodontic appliance, comprising:
a body having at least one archwire attaching portion for attaching an archwire thereto, wherein the at least one archwire attaching portion has at least a bottom and opposing sides;
a base having a side for facing a surface of a tooth when the orthodontic appliance is affixed to the tooth via an adhesive, the side having a plurality of surfaces for facing the tooth, including an outer surface for contacting the tooth, and a plurality of recessed surfaces offset from the tooth when the appliance is affixed to the tooth;
an embedded encoding of information in the side of the base wherein there are walls defining each symbol of the encoding, wherein substantially all of the walls span an extent between at least two of the recessed surfaces of the side base, and a total surface area of the side of the base, including an area of the walls, for bonding of the appliance to the tooth with the adhesive is greater than what the total surface area would be without the encoding of information in the side of the base;
wherein the area of the walls is at least 29% of the total surface area of the side of the base for contacting the adhesive and affixing the base to the tooth; and
a discontinuous perimeter rail attached substantially entirely as a perimeter of the side of the base and projecting away from the body, wherein the discontinuous perimeter rail includes the outer surface, so that when the discontinuous perimeter rail contacts the tooth for attaching the orthodontic appliance thereto, substantially all of the total surface area of the side of the base within the discontinuous perimeter rail is offset from the tooth so that a thickness of the adhesive between substantially an entirety of the total surface area of the side of the base within the discontinuous perimeter rail and the tooth can be controlled by excessive adhesive escaping from substantially all of the total surface area of the side of the base within the discontinuous perimeter rail via discontinuities in the discontinuous perimeter rail.

2. The orthodontic appliance of claim 1, wherein the encoding of information includes an identification of a supplier of the orthodontic appliance.

3. The orthodontic appliance of claim 1, wherein the encoding of information includes an identification of at least one of:
(a) a manufacturer of the orthodontic appliance;
(b) a location of the orthodontic appliance;
(c) a date of manufacturer of the orthodontic appliance;
(d) an identification of the materials used for manufacturing the orthodontic appliance;
(e) an identification of the orthodontic appliance; and
(f) an identification of the version of the documentation supplied with the orthodontic appliance.

4. The orthodontic appliance of claim 3, wherein the encoding of information includes an identification of at least two of (a) a manufacturer of the orthodontic appliance; (b) a location of the orthodontic appliance: (c) a date of manufacturer of the orthodontic appliance; (d) an identification of the materials used for manufacturing the orthodontic appliance; (e) an identification of the orthodontic appliance; and (f) an identification of the version of the documentation supplied with the orthodontic appliance.

5. The orthodontic appliance of claim 3, wherein the encoding of information includes an identification of at least three of (a) a manufacturer of the orthodontic appliance; (b) a location of the orthodontic appliance: (c) a date of manufacturer of the orthodontic appliance; (d) an identification of the materials used for manufacturing the orthodontic appliance; (e) an identification of the orthodontic appliance; and (f) an identification of the version of the documentation supplied with the orthodontic appliance.

6. The orthodontic appliance of claim 1, wherein the encoding of information includes an occurrence of at least one character that does not convey information related to the orthodontic appliance.

7. The orthodontic appliance of claim 1, wherein the encoding of information includes a logo.

8. The orthodontic appliance of claim 1, wherein the encoding of information includes a pattern that can be optically scanned for obtaining information on the orthodontic appliance.

9. The orthodontic appliance of claim 1, wherein the at least one archwire encoding of information includes a patent number.

10. The orthodontic appliance of claim 1, wherein the at least one archwire attaching portion includes a tube.

11. The orthodontic appliance of claim 1, wherein the attaching portion includes a slot for the archwire.

12. The orthodontic appliance of claim 1, wherein for each wall of at least most of the walls, the wall is between about 0.009 to 0.011 inches in extent between the respective base surface levels between which the walls span.

13. The orthodontic appliance of claim 1, wherein the escape of the excessive adhesive reduces an increase in hydraulic pressure within the adhesive for moving the appliance away from the tooth.

14. The orthodontic appliance of claim 1, wherein the underneath side of the base includes a channel extending between opposing edges of the perimeter of the underneath side of the base, the channel configured for engaging with a dental tool for facilitating one of placement and removal of the appliance from the tooth.

15. An orthodontic appliance, wherein the appliance has information embedded into an underneath side of a base of the appliance, comprising:
a plurality of characters formed in the underneath side of the base in a manner such that the plurality characters serve to increase a total surface area of the underneath side of the base so that an adhesive can adhere thereto for bonding of the orthodontic appliance with a patient's tooth;
a perimeter rail provided substantially as a perimeter of the underneath side of the base and projecting outwardly further than substantially all of the underneath side of the base not part of the perimeter rail, wherein when the perimeter rail contacts the tooth for attaching the orthodontic appliance thereto, substantially all of the total surface area within the perimeter rail is offset from the tooth so that a thickness of the adhesive between the underneath side of the base and the tooth can be controlled by excessive adhesive escaping, via discontinuities in the perimeter rail, from between substantially all of the total surface area of the underneath side of the base within the perimeter rail that is offset from the tooth;
wherein the walls for defining the plurality of characters increase the total surface area of the underneath side of the base to over 140% of a surface area of a side base identical to the underneath side of the base but without the walls;
wherein for each point of at least most of the points of the underneath side of the base enclosed by the walls, there are not two walls within 0.008 inches of the point.

16. The orthodontic appliance of claim 15, wherein for a two dimensional surface area corresponding to the underneath side of the base, 50% to 60% of the two dimensional surface area corresponds to a portion of the underneath side of the base that is enclosed by the walls of the side base, and 50% to 40% of the two dimensional surface area corresponds to a portion of the underneath side of the base that is not enclosed by the walls, wherein when the orthodontic appliance is attached to the tooth, for the 50% to 60% of the two dimensional base surface area is further from the tooth than the 50% to 40% of the two dimensional surface area.

17. The orthodontic appliance of claim 16, wherein the 50% to 60% of the two dimensional surface area is about 55%.

18. The orthodontic appliance of claim 14, wherein the channel is configured for engaging with a dental tool in a manner that restricts rotational movement therebetween.

* * * * *